United States Patent [19]

Mizuchi et al.

[11] Patent Number: 5,264,435
[45] Date of Patent: Nov. 23, 1993

[54] PYRIMIDINES AND THEIR PHARMACEUTICAL ACCEPTABLE SALTS, AND THEIR USE AS MEDICINES

[75] Inventors: Akira Mizuchi; Kazutoshi Horikomi; Tadayuki Sasaki, all of Mobara; Akira Awaya, Yokohama; Ikuo Tomino, Ohtake; Noriaki Kihara, Iwakuni; Takumi Kitahara, Ohtake, all of Japan

[73] Assignee: Mitsui Petrochemical Industries, Ltd., Tokyo, Japan

[21] Appl. No.: 888,726

[22] Filed: May 26, 1992

Related U.S. Application Data

[62] Division of Ser. No. 459,376, Dec. 29, 1989, Pat. No. 5,147,876.

[30] Foreign Application Priority Data

Dec. 29, 1988 [JP] Japan .................................. 63-333670
Feb. 23, 1989 [JP] Japan .................................. 1-41728
Feb. 23, 1989 [JP] Japan .................................. 1-41729

[51] Int. Cl.$^5$ ................ A61K 31/505; A61K 31/495; C07D 487/00
[52] U.S. Cl. .................................. 514/254; 514/258; 544/280
[58] Field of Search ............... 544/280; 514/254, 258

[56] References Cited

U.S. PATENT DOCUMENTS

| | | | |
|---|---|---|---|
| 3,714,165 | 1/1973 | Beaulour et al. | 514/275 |
| 3,775,412 | 11/1973 | Kim et al. | 544/280 |
| 3,984,414 | 10/1976 | Esanu | 544/322 |
| 4,073,895 | 2/1978 | Esanu | 544/322 |
| 4,226,995 | 10/1980 | Demosthene et al. | 544/334 |
| 4,266,058 | 5/1981 | Demosthene et al. | 544/330 |
| 4,267,181 | 5/1981 | Esanu | 544/330 |
| 4,297,495 | 10/1981 | Esanu | 544/330 |
| 4,344,947 | 8/1982 | Huve | 424/251 |
| 4,416,885 | 11/1983 | Huve | 544/330 |
| 4,742,165 | 5/1988 | Yohoyama et al. | 544/280 |
| 4,959,368 | 9/1990 | Awaya et al. | 544/280 |

FOREIGN PATENT DOCUMENTS

| | | |
|---|---|---|
| 0192783 | 3/1986 | European Pat. Off. . |
| 0257102 | 3/1988 | European Pat. Off. . |
| 269393 | 5/1989 | European Pat. Off. . |
| 2539414 | 7/1984 | France . |
| 46-23394 | 7/1971 | Japan . |
| 51-22044 | 7/1976 | Japan . |
| 52-100477 | 8/1977 | Japan . |
| 54-157575 | 12/1979 | Japan . |
| 55-393 | 1/1980 | Japan . |
| 55-122768 | 9/1980 | Japan . |
| 55-145670 | 11/1980 | Japan . |
| 55-145671 | 11/1980 | Japan . |
| 55-151571 | 11/1980 | Japan . |
| 56-10177 | 2/1981 | Japan . |
| 56-26880 | 3/1981 | Japan . |
| 56-90013 | 7/1981 | Japan . |
| 61-65873 | 4/1986 | Japan . |
| 1-50193 | 5/1989 | Japan . |

OTHER PUBLICATIONS

Patent Abstracts of Japan, vol. 11, No. 282 (C-446) (2729), 11 Sep. 1987, JP-A-62 81 375 (Teikoku Chem. Ind. Corp. Ltd.), 14 Apr. 1987.
The Jouranl of Chemica Society, 1965, 755-761.
La nouvelle Presse Medicale, vol. 16, 1189-1280.

*Primary Examiner*—Cecilia Tsang
*Attorney, Agent, or Firm*—Sherman and Shalloway

[57] ABSTRACT 2,6-di-, 2,4,6-, 2,5,6-tri- or 2,4,5,6-tetra-substituted pyrimidines, and 2,6-di-substituted pyridines. These compounds are useful for treatment of neurological deseases.

5 Claims, No Drawings

PYRIMIDINES AND THEIR PHARMACEUTICAL ACCEPTABLE SALTS, AND THEIR USE AS MEDICINES

This is a division of application Ser. No. 07/459,376, filed Dec. 29, 1989, now U.S. Pat. No. 5,147,876.

This invention relates to novel pyrimidines or their pharmaceutically acceptable salts, and novel therapeutic agents for neurological diseases of the peripheral and central nervous systems of animals containing the above compounds as active ingredients. Japanese Patent Publication No. 23,394/1971 discloses that aminopyrimidines represented by the following formula

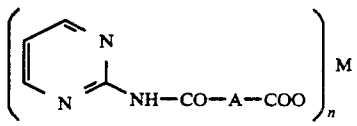

wherein A represents an alkylene group having up to 16 carbon atoms, or a lower alkylene group substituted by an amino group or a $C_{2-5}$ acylamino group, M represents H, Na, K, $NH_4$, Mg, Ca or an organic basic ammonium salt, and n is a value equal to the atomic valency of M, have interesting therapeutic activity, particularly as an anti-melanchoric agent and psychoanaleptic agent in the field of psychosis.

Japanese Patent Publication No. 22044/1976 discloses that dichloro-lower aliphatic carboxylic acid salts of 2-isopropylaminopyrimidine, such as 2-isopropylaminopyrimidine dichloroacetate, are useful as a therapeutic agent for a neurological disease.

Japanese Laid-Open Patent Publication No. 100477/1977 (Patent Publication No. 28548/1984) discloses that 2-isopropylaminopyrimidine phosphate is useful as a therapeutic agent for a neurological disease.

Japanese Laid-Open Patent No. 157575/1979 discloses a process-for producing 2-chloropyrimidine in a high yield. A working example in this patent publication describes the preparation of 2-chloropyrimidine in a yield of 69%.

Japanese Laid-Open Patent Publication No. 393/1980 discloses a process for producing 2-isopropylaminopyrimidine in a high yield. A working example of this patent publication describes the preparation of 2-isopropylaminopyrimidine in a yield of 60%.

Japanese Laid-Open Patent Publication No. 122768/1980 discloses that a hydroxy derivative of 2-isopropylaminopyrimidine represented by the following formula

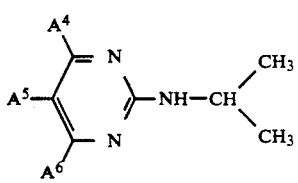

wherein $A^4$, $A^5$ and $A^6$ each represent H or OH, and at least one of them represents OH, is useful in the field of nerve regeneration and for treatment of myodystrophy.

Japanese Laid-Open Patent Publication No. 145670/1980 discloses that 2-isopropylaminohalogenopyrimidines represented by the following formula

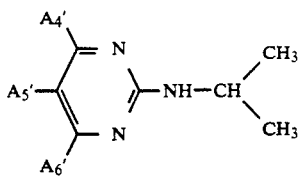

wherein $A_4'$, $A_5'$ and $A_6'$ each represent H or a halogen atom, and at least one of them is a halogen atom, are useful for treatment of various neurological diseases and myodystrophy.

Japanese Laid-Open Patent Publication No. 145,671/1980 discloses a process for producing a hydroxy derivative of 2-isopropylaminopyrimidine.

Japanese Laid-Open Patent Publication No. 151,571/1980 discloses that 2-isopropylamino-5-halogenopyrimidines are interesting in the treatment of neurological diseases.

Japanese Laid-Open Patent Publication No. 10177/1981 discloses a process for producing 2-isopropylaminopyrimidine substantially in a quantitative yield by aminolyzing 2-methylsulfonylpyrimidine with isopropylamine.

Japanese Laid-Open Patent Publication No. 26880/1981 discloses a process for producing 2-isopropylaminopyrimidine which comprises reacting bis-(isopropylguanidine) sulfate with 1,1,3,3-tetraethoxypropane.

Japanese Laid-Open Patent Publication No. 90,013/1981 describes a therapeutic agent for myodystropy, myopathy, muscle rigidity and/or dysfunction of neuro-musclar transmission comprising substituted derivative of pyrimidine or its therapeutically acceptable salt or its metabolite as an active ingredient. However, it merely discloses various salts such as an orthophosphate, of 2-isopropylaminopyrimidine as an active compound.

Japanese Laid-Open Patent Publication No. 65873/1986 discloses that 2-piperazinopyrimidines of the following formula

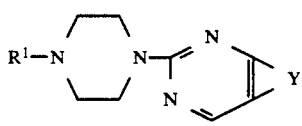

wherein $R^1$ is H or aralkyl, and Y is a divalent organic group defined in the claim of this patent publication, are useful as a herbicide for paddies and upland farms.

The present inventors previously provided a novel therapeutic agent for treatment of neurological diseases comprising a specific 2-piperazinopyrimidine derivative or its pharmaceutically acceptable salt (International Laid-Open No. WO87/04928).

It is an object of this invention to provide novel pyrimidines and their pharmaceutically acceptable salts.

Another object of this invention is to provide therapeutic agents for neurological diseases and spinal breakdown comprising the above novel compounds.

Another object of this invention is to provide a novel therapeutic agent for neurological diseases having the effect of regenerating and repairing nerve cells.

Another object of this invention is to provide a novel therapeutic agent for neurological diseases which can be applied to disorders of peripheral nerves, cerebrospinal injury, etc.

Another object of this invention is to provide a novel therapeutic agent for neurological diseases which can be applied to diseases of central nerves which are different from psycosis and in which abnormality in the operating system or the metabolic system of chemical transmitters is regarded as being primarily involved.

Another object of this invention is to provide a novel therapeutic agent for cerebral diseases which has the effect of improving and restoring learning and memory.

Another object of this invention is to provide a novel therapeutic agent for neurological diseases or cerebral diseases, which comprises a comprehensively excellent and useful compound having pharmacological actions suitable for treatment of neurological diseases or cerebral diseases with little side effects such as liver trouble.

Further objects of this invention along with its advantages will become apparent from the following description.

According to this invention, there is first provided a pyrimidine represented by the following formula (1), or its pharmaceutically acceptable salt $$\text{(1)}$$

wherein $R^1$ represents a hydrogen atom or a lower alkyl group; X represents a group of the formula $$-N\diagup\diagdown O,$$

a group of the formula $$-N\diagup\diagdown N-R^2$$

in which $R^2$ represents a hydrogen atom, a lower alkyl group, a phenyl group, a benzyl group or an alpha-(p-chlorophenyl)benzyl group,
a group of the formula in which $R^3$ corresponds to one or at least two identical or different substituents replacing one or at least two hydrogen atoms of identical or different methylene groups, and represents a lower alkyl group, a hydroxyl group, a phenyl group optionally substituted by nitro, a benzyl group, a benzoyloxy group, a benzoylamino group, a lower alkylamino group, a di-lower alkylamino group, the $HO(C_6H_5)_2C-$ group, a piperidino group, a hydroxy(lower alkyl) group, the $C_6H_5SO_2O-$ group, a benzoyl group optionally substituted by halogen, a lower alkylsulfonylamide group or a lower alkoxycarbonyl group, and n is a number of 4, 5, 6 or 7, a group of the formula $$-N\diagup\diagdown\substack{R^4\\R^5}$$

in which $R^4$ represents a hydrogen atom, a lower alkyl group or a benzyl group, and $R^5$ represents a lower alkyl group, a lower acyl group, a 2-furoyl group, a benzyl group, a 4-piperidyl group optionally substituted by benzoyl, a phenethyl group, the group or a benzoyl group optionally substituted by halogen or nitro, a group of the formula a group of the formula a group of the formula or a group of the formula Y represents a group of the formula

—CH$_2$R$^9$ wherein R$^9$ represents a hydrogen atom, a lower alkyl group, a lower alkoxy group, a lower alkylthio group, or a di-lower alkylamino group, a group of the formula

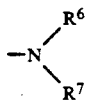

wherein R$^6$ represents a hydrogen atom, a lower alkyl group, a phenyl group, a benzyl group, a lower alkoxy group or a 2-(N,N-dimethylamino)ethyl group, and R$^7$ represents a lower alkyl group, a lower acyl group, a cyclohexylcarbonyl group, a 2-furoyl group, a lower alkoxycarbonyl group, a cinnamoyl group, a benzyl group, a benzylcarbonyl group, a tosyl group, a phenoxyacetyl group, a di-lower alkylcarbamoyl group, a 2-thienyl group, a group of the formula

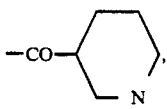

a group of the formula

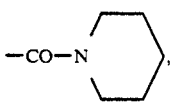

a group of the formula

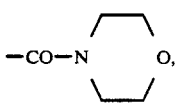

a group of the formula

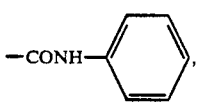

a group of the formula

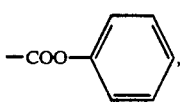

a 4-lower alkylpiperazyl group, or a benzoyl group optionally substituted by halogen, nitro, lower alkyl, lower alkoxy, amino, benzoylamino or phenyl, provided that when R$^6$ is a hydrogen atom, R$^7$ is a benzoyl group, a group of the formula

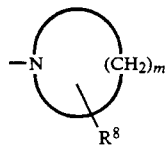

wherein R$^8$ corresponds to a substituent replacing the hydrogen atom of the methylene group, and represents a hydrogen atom, a lower alkyl group, a phenyl group or a benzyl group, and m is a number of 4, 5, 6 or 7, a group of the formula

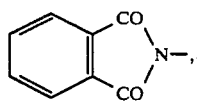

a group of the formula

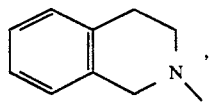

or a group of the formula

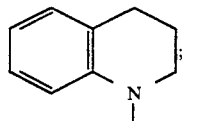

and Z represents a hydrogen atom, a halogen atom, a lower alkyl group or a lower alkoxycarbonyl group; provided that Y represents —CH$_2$R$^9$ only when Z is a lower alkoxycarbonyl group; that R$^4$ represents a hydrogen atom only when R$^5$ represents a lower alkyl group, a lower acyl group, a 2-furoyl group, a benzyl group, a phenethyl group or a benzoyl group optionally substituted by halogen or nitro, Y represents CH$_2$R$^9$ and Z represents a lower alkoxy carbonyl group; that Y can be

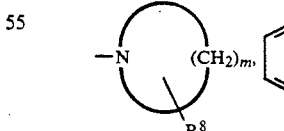 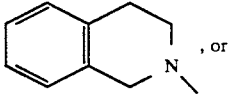, or

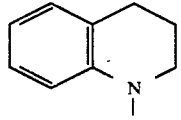

only when X is

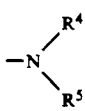

and $R^4$ is a lower alkyl group.

In formula (1), $R^1$ is a hydrogen atom or a lower alkyl group. The lower alkyl group may be linear or branched, and preferably has 1 to 4 carbon atoms. Examples include methyl, ethyl, n-propyl, isopropyl n-butyl, sec-butyl, isobutyl and t-butyl groups.

In formula (I), X represents a group of the formula

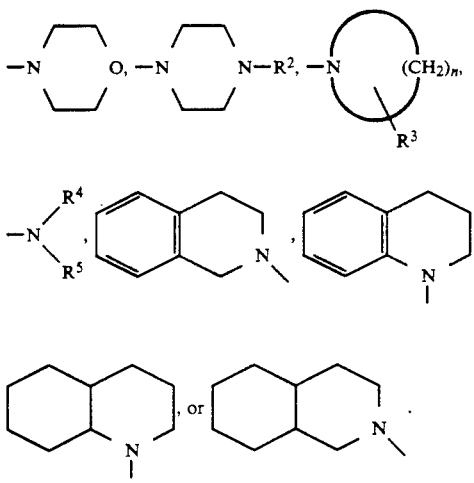

In the above formulae, $R^2$ represents a hydrogen atom, a lower alkyl group, phenyl group, benzyl group or an alpha-(p-chlorophenyl)benzyl group. Examples of the lower alkyl group may be the same as those exemplified for $R^1$.

$R^3$ corresponds to a substituent replacing the hydrogen atom of the methylene group, and represents a lower alkyl group, a hydroxyl group, a phenyl group optionally substituted by nitro, a benzyl group, a benzoyloxy group, a benzoylamino group, a lower alkyl-amino group, a di-lower alkylamino group, the $HO(C_6H_5)_2C$-group, a piperidino group, a hydroxy(-lower alkyl) group, the $C_6H_5SO_2O-$ group, a benzoyl group optionally substituted by halogen, a lower alkyl-sulfonylamide group, or a lower alkoxycarbonyl group. n is a number of 4, 5, 6 or 7. Examples of the lower alkyl groups may be the same as those exemplified above with regard to $R^1$.

$R^4$ represents a hydrogen atom, a lower alkyl group or a benzyl group, and $R^5$ represents a lower alkyl group, a lower acyl group, a 2-furoyl group, a benzyl group, a 4-piperidyl group optionally substituted by benzoyl, a phenethyl group or the group

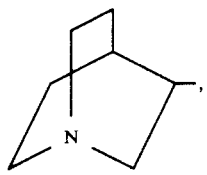

or a benzoyl group optionally substituted by halogen or nitro.

Examples of the lower alkyl groups for $R^4$ and $R^5$ may be the same as those $R^5$.

The alkyl moiety of the lower acyl group for $R^5$ may be linear or branched.

Acyl groups having 2 to 6 carbon atoms are preferred, and examples include acetyl, propionyl, butyryl, isobutyryl, valeryl, isovaleryl and hexanoyl groups.

In formula (I), Y represents a group of the formula

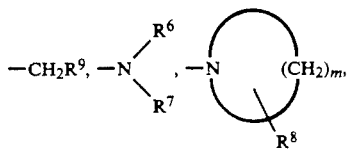

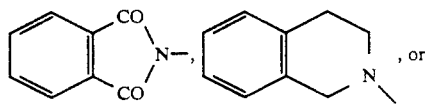

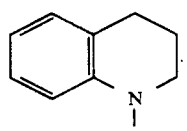

$R^9$ represents a hydrogen atom, a lower alkyl group, a lower alkoxy group, a lower alkylthio group, or a di-lower alkylamino group. $R^6$ represents a hydrogen atom, a lower alkyl group, a phenyl group, a benzyl group, a lower alkoxy group or a 2-(N,N-dimethylamino)ethyl group. $R^7$ represents a lower alkyl group, a lower acyl group, a cyclohexylcarbonyl group, a 2-furoyl group, a lower alkoxycarbonyl group, a cinnamoyl group, a benzyl group, a benzylcarbonyl group, a tosyl group, a phenoxyacetyl group, a di-lower alkylcarbamoyl group, a 2-thienyl group, a group of the formula

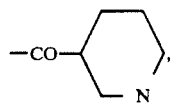

a group of the formula

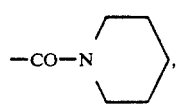

a group of the formula

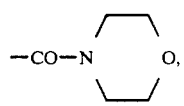

a group of the formula

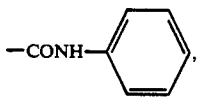

a group of the formula

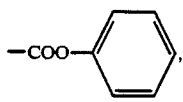

a 4-lower alkylpiperazyl group, or a benzoyl group which may be substituted by halogen, lower alkoxy, nitro, amino, benzoylamino or phenyl.

Examples of the lower alkyl groups for $R^9$, $R^6$ and $R^7$ may be the same as those exemplified with respect to $R^1$.

Examples of the lower acyl group for $R^7$ may be the same as those exemplified above for $R^5$.

Examples of the halogen and lower alkoxy group as substituent for the benzoyl group $R^7$ are fluorine, chlorine, bromine and iodine, and alkoxy groups having 1 to 4 carbon atoms such as methoxy, ethoxy, propoxy, isopropoxy, butoxy, isobutoxy and sec-butoxy. When $R^6$ is a hydrogen atom, $R^7$ is a benzoyl group.

Furthermore, in formula (1), Z represents a hydrogen atom, a halogen atom, a lower alkoxycarbonyl group or a lower alkyl group.

Examples of the halogen atom are fluorine, chlorine, bromine and iodine. Examples of the lower alkyl group may be the same as those exemplified with respect to $R^1$.

According to this invention, there is further provided a compound represented by the following formula (2), or its pharmaceutically acceptable salt,

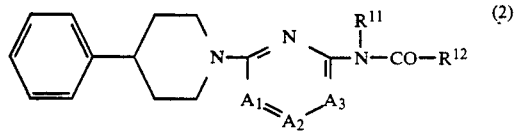

wherein $A_1$ represents =CH— or —N=; $A_2$ is =CH—, —N=, or

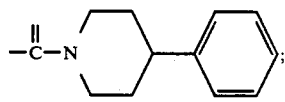

$A_3$ represents =CH— or —N=; $R^{11}$ represents a lower alkyl group; $R^{12}$ represents a phenyl group optionally substituted by halogen, lower alkyl or lower alkoxy, a 2-furyl group, or a 2-thienyl group; provided that
when $A_1$ is —N=, $A_2$ is

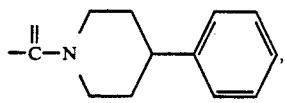

when $A_1$ and $A_2$ are =CH—, $A_3$ is =CH—, and when $A_2$ is —N=, $A_1$ and $A_3$ are =CH—.

In formula (2), $R^{11}$ is a lower alkyl group. $R^{12}$ represents a phenyl group optionally substituted by halogen, lower alkyl or lower alkoxy, a 2-furyl group or a 2-thienyl group.

Examples of the lower alkyl groups for $R^{11}$ and $R^{12}$ may be the same as those exemplified above with regard to $R^1$.

$A_1$ is =CH— or =N—, and $A_2$ is =CH—, —N=, or

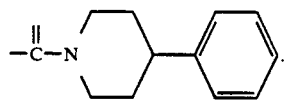

$A_3$ is =CH— or —N=. When $A_1$ is —N=, $A_2$ is

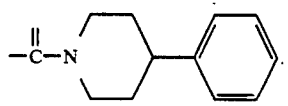

When $A_1$ and $A_2$ are =CH—, $A_3$ is =CH—. When $A_2$ is —N=, $A_1$ and $A_2$ are =CH—.

According to still another aspect, there is also provided a novel compound of the following formula (3) having the same pharmacological efficacy.

A pyrimidine of formula (3), or its pharmaceutically acceptable salt,

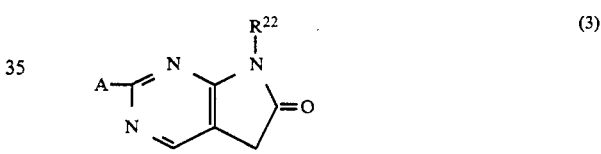

wherein A represents a group of the formula

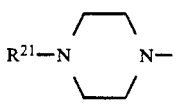

or a group of the formula

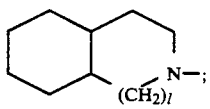

$R^{21}$ represents a group of the formula (a)

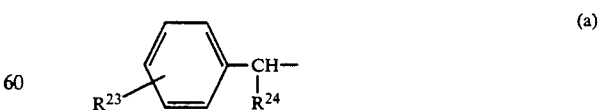

wherein $R^{23}$ represents a hydrogen atom, a lower alkyl group, a lower alkoxy group or a phenyl group and $R^{24}$ represents a hydrogen atom, a lower alkyl group, a cyclohexyl group, a phenyl group, a 4-halogenophenyl group, a p-diphenyl group, a 2-pyridyl group or a 2-thiophenyl group, provided that $R^{23}$ and $R^{24}$ are not hydrogen atoms at the same time;

or a group of the formula (b)

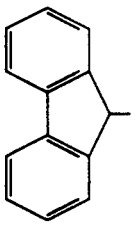

which is a 9-fluorenyl group or a triphenylmethyl group; $R^{22}$ represents a lower alkyl group; and l is a number of 0 or 1.

In formula (3), A represents a group of the formula

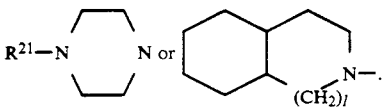

$R^{21}$ represents a group of the following formula (a)

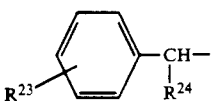

(a)

or a group of the following formula (b)

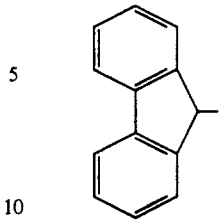

which is a 9-fluorenyl or triphenylmethyl group.

$R^{23}$ in formula (a) is a hydrogen atom, a lower alkyl group, a lower alkoxy group or a phenyl group, and $R^{24}$ represents a hydrogen atom, a lower alkyl group, a cyclohexyl group, a phenyl group, a 4-halogenophenyl group, a p-diphenyl group, a 2-pyridyl group, or a 2-thiophenyl group. $R^{23}$ and $R^{24}$ are not hydrogen atoms at the same time.

The lower alkyl groups for $R^{23}$ and $R^{24}$, independently from each other, may be linear or branched and preferably contain 1 to 4 carbon atoms. Examples are methyl, ethyl, n-propyl, isopropyl, n-butyl, sec-butyl and isobutyl groups.

The lower alkoxy group for $R^{23}$ may be linear or branched, and those having 1 to 4 carbon atoms are preferred. Examples include methoxy, ethoxy, n-propoxy, isopropoxy, n-butoxy, sec-butoxy, isobutoxy and t-butoxy groups. Examples of the 4-halogenophenyl group for $R^{24}$ are 4-fluorophenyl, 4-chlorophenyl or 4-bromophenyl.

In formula (3), $R^{22}$ is a lower alkyl group examples of which may be same as those given for $R^{23}$. l is a number of 0 or 1.

Examples of formulae (1), (2) and (3) provided by this invention are given below.

(100) 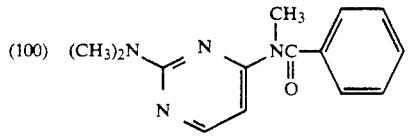

(104) p-Toluenesulfonate of (100)

(108) 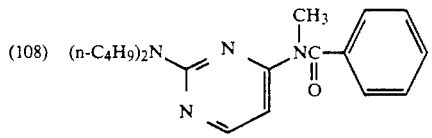

(112) p-Toluenesulfonate of (108)

(116) 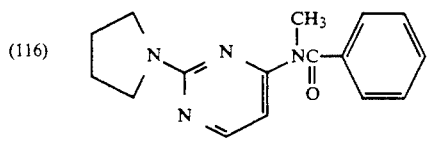

(120) p-Toluenesulfonate of (116)

(124) 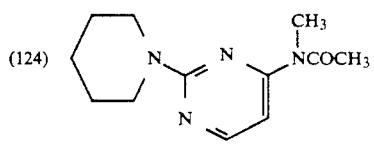

-continued
(128) p-Toluenesulfonate of (124)
(132) 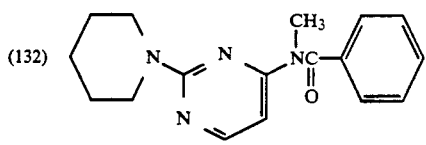
(136) p-Toluenesulfonate of (132)
(137) 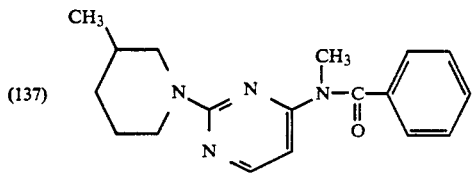
(138) p-Toluenesulfonate of (137)
(140) 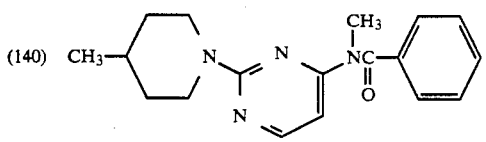
(144) p-Toluenesulfonate of (140)
(149) 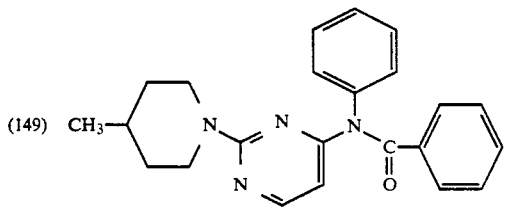
(150) p-Toluenesulfonate of (149)
(148) 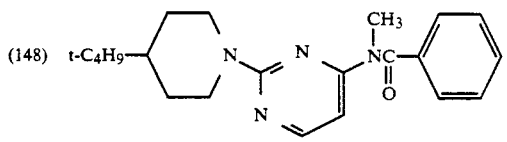
(152) p-Toluenesulfonate of (148)
(145) 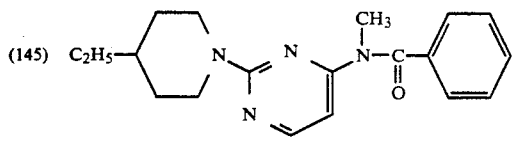
(146) p-Toluenesulfonate of (145)
(147) 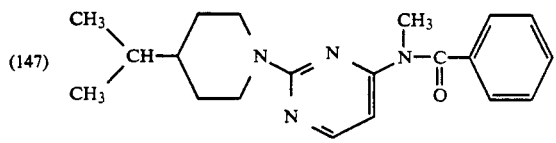
(147-1) p-Toluenesulfonate of (147)

-continued
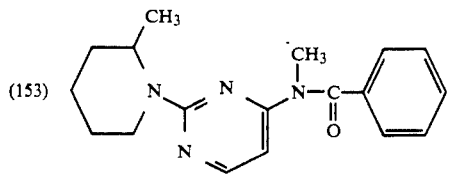
(154) p-Toluenesulfonate of (153)
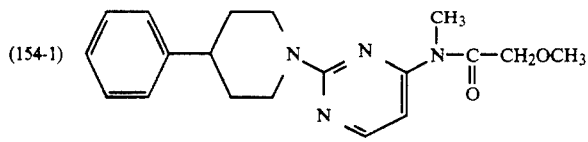
(154-2) p-Toluenesulfonate of (154-1)
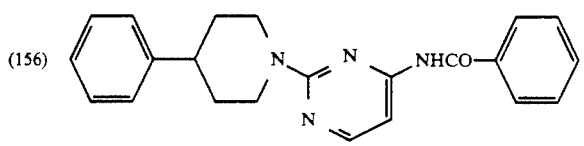
(160) p-Toluenesulfonate of (156)
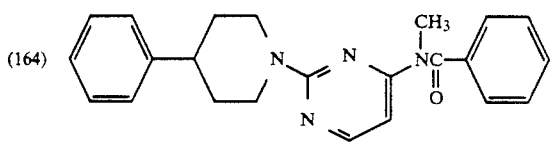
(165) Sulfate of (164)
(166) Phosphate of (164)
(167) Maleate of (164)
(169) Naphthalenesulfonate of (164)
(171) Citrate of (164)
(171-1) Tartarate of (164)
(171-1-1) Fumarate of (164)
(168) p-Toluenesulfonate of (164)
(170) Hydrochloride of (164)
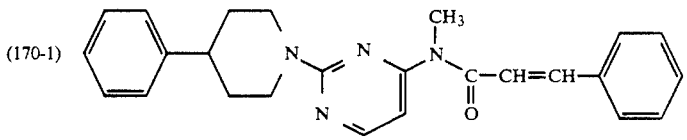
(170-2) p-Toluenesulfonate of (170-1)
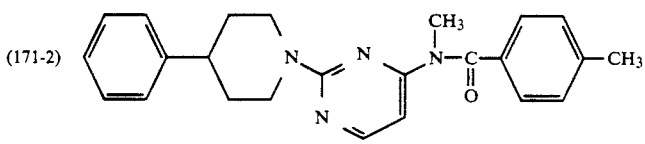
(171-3) p-Toluenesulfonate of (171-2)
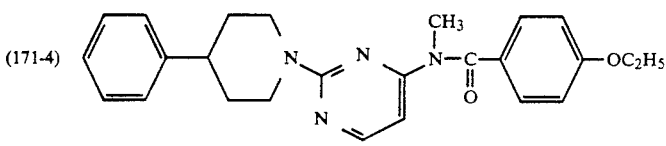
(171-5) p-Toluenesulfonate of (171-4)

-continued
(171-6) 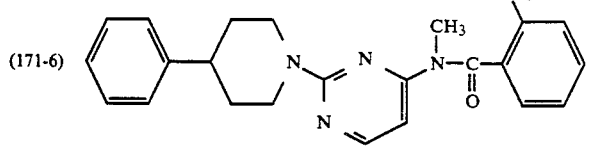
(171-7) p-Toluenesulfonate of (171-6)
(171-8) 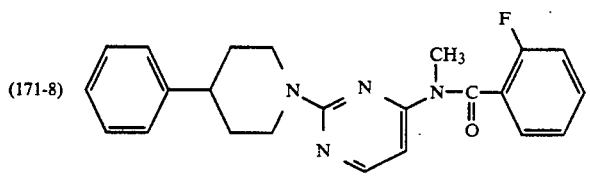
(171-9) p-Toluenesulfonate of (171-8)
(171-10) 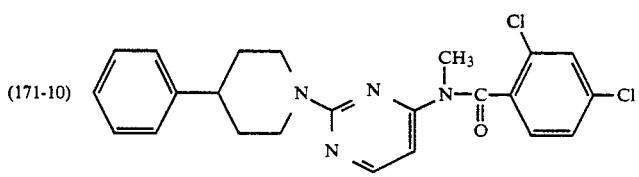
(171-11) p-Toluenesulfonate of (171-10)
(171-12) 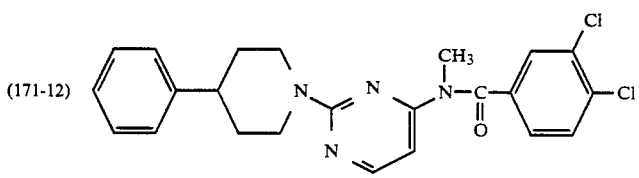
(171-13) p-Toluenesulfonate of (171-12)
(172) 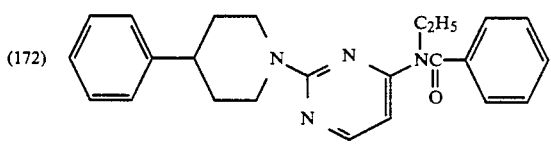
(176) p-Toluenesulfonate of (172)
(180) 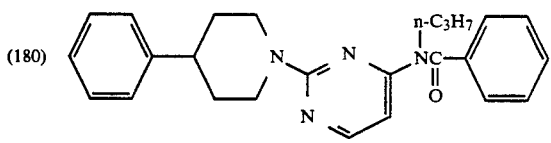
(184) p-Toluenesulfonate of (180)
(188) 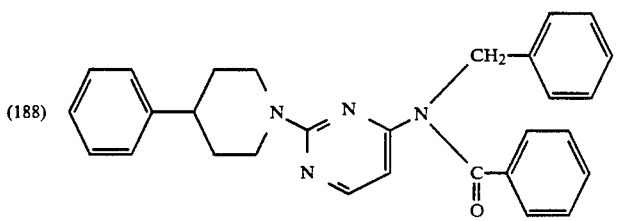
(192) p-Toluenesulfonate of (188)

(196) 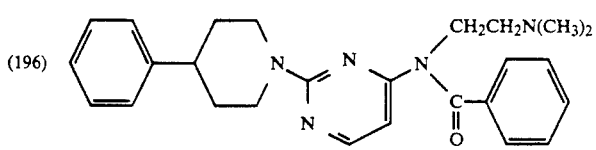
(200) p-Toluenesulfonate of (196)
(204) 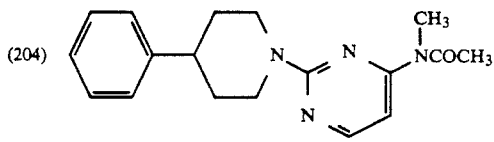
(208) p-Toluenesulfonate of (204)
(212) 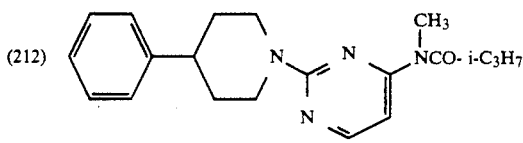
(216) p-Toluenesulfonate of (212)
(220) 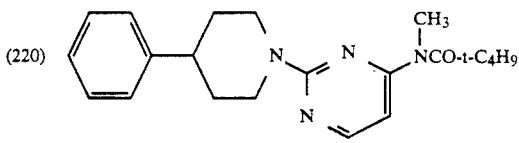
(224) p-Toluenesulfonate of (220)
(228) 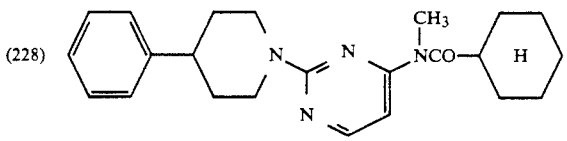
(232) p-Toluenesulfonate of (228)
(236) 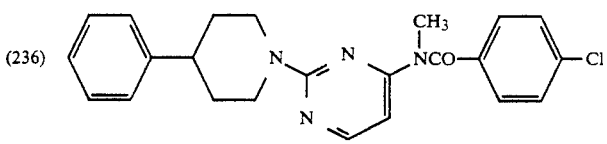
(240) p-Toluenesulfonate of (236)
(241) 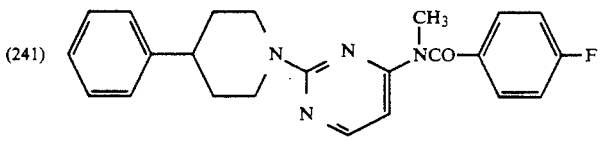
(242) p-Toluenesulfonate of (241)
(244) 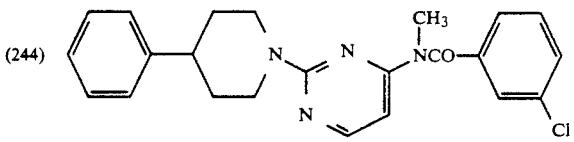
(248) p-Toluenesulfonate of (244)

(252) 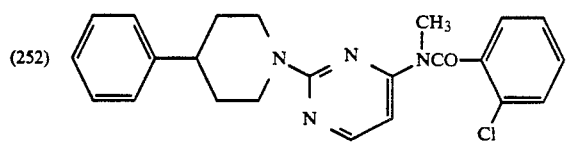
(256) p-Toluenesulfonate of (252)
(260) 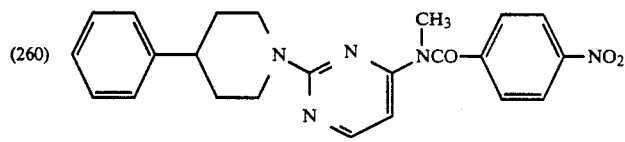
(264) p-Toluenesulfonate of (260)
(268) 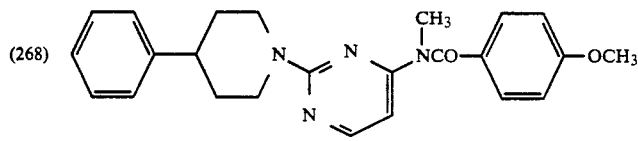
(272) p-Toluenesulfonate of (268)
(276) 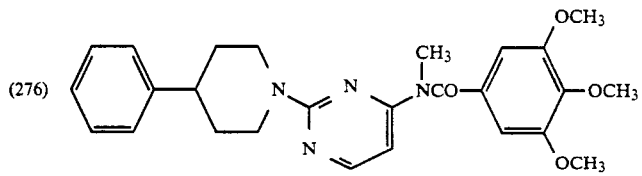
(280) p-Toluenesulfonate of (276)
(284) 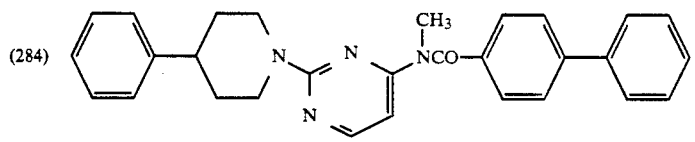
(288) p-Toluenesulfonate of (284)
(292) 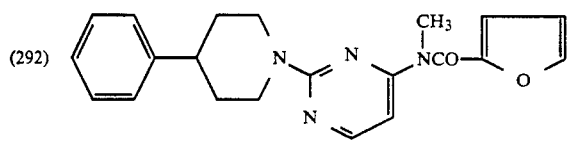
(296) p-Toluenesulfonate of (292)
(297) 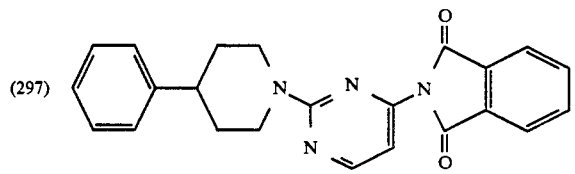
(298) p-Toluenesulfonate of (297)
(300) 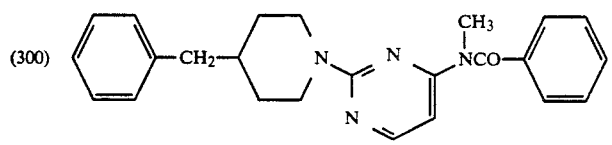
(304) p-Toluenesulfonate of (300)

(305) 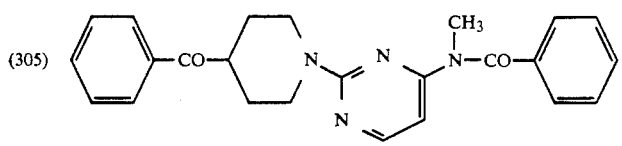
(306) p-Toluenesulfonate of (305)
(307) 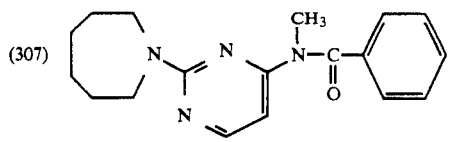
(307-1) Hydrochloride of (307)
(308) 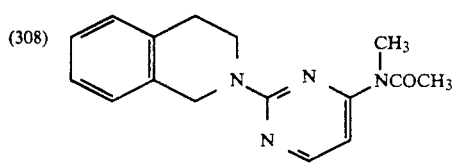
(312) p-Toluenesulfonate of (308)
(316) 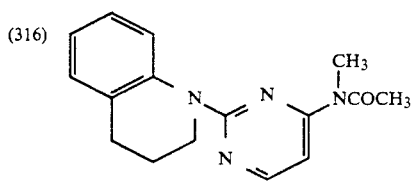
(320) p-Toluenesulfonate of (316)
(324) 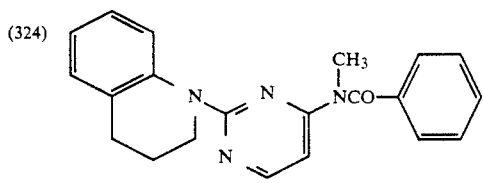
(328) p-Toluenesulfonate of (324)
(332) 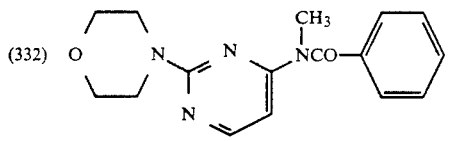
(336) p-Toluenesulfonate of (332)
(340) 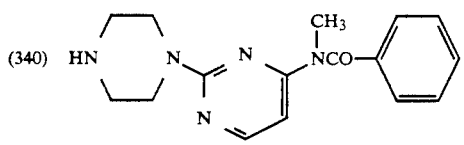
(344) p-Toluenesulfonate of (340)
(348) 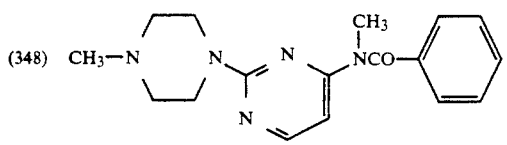
(352) p-Toluenesulfonate of (348)

(356) 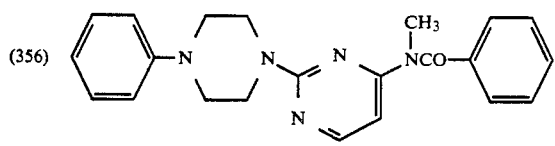
(360) p-Toluenesulfonate of (356)
(364) 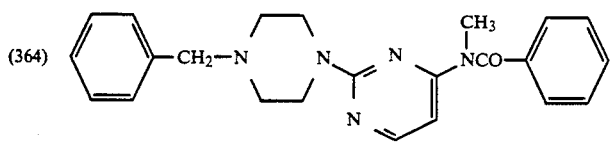
(368) p-Toluenesulfonate of (364)
(372) 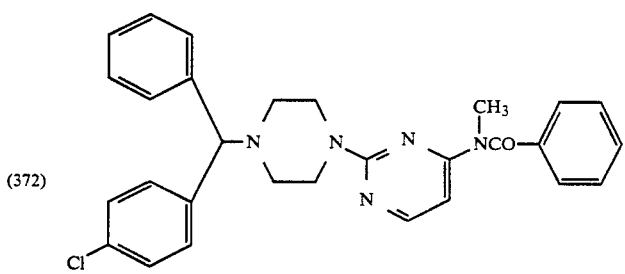
(376) p-Toluenesulfonate of (372)
(380) 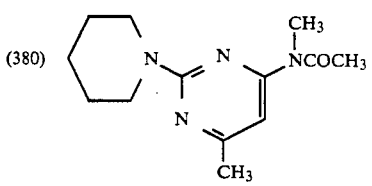
(384) p-Toluenesulfonate of (380)
(388) 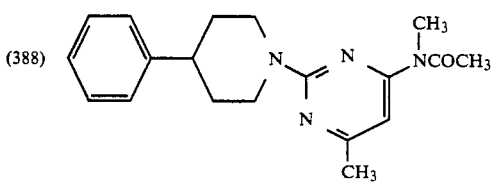
(392) p-Toluenesulfonate of (388)
(396) 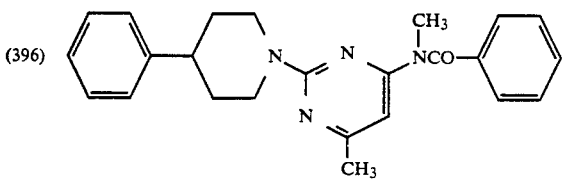
(400) p-Toluenesulfonate of (396)
(404) 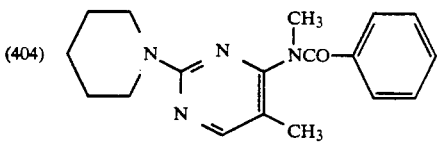
(408) p-Toluenesulfonate of (404)

(412) 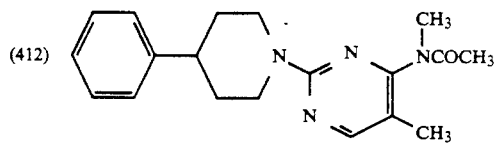
(416) p-Toluenesulfonate of (412)
(420) 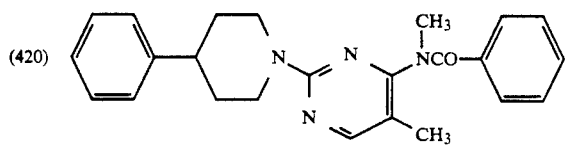
(424) p-Toluenesulfonate of (420)
(428) 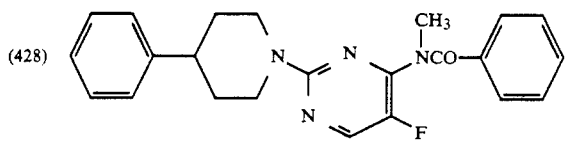
(432) p-Toluenesulfonate of (428)
(600) 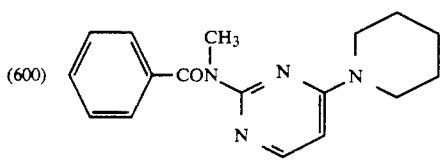
(604) p-Toluenesulfonate of (600)
(608) 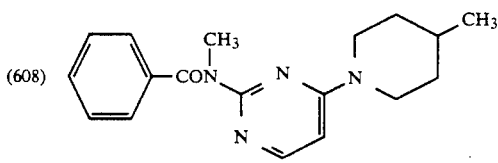
(612) p-Toluenesulfonate of (608)
(616) 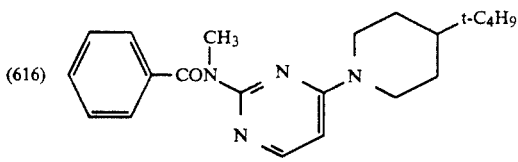
(620) p-Toluenesulfonate of (616)
(624) 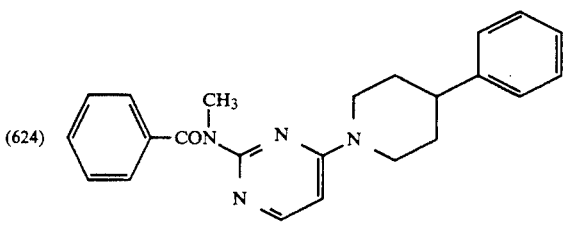
(628) p-Toluenesulfonate of (624)

(632) 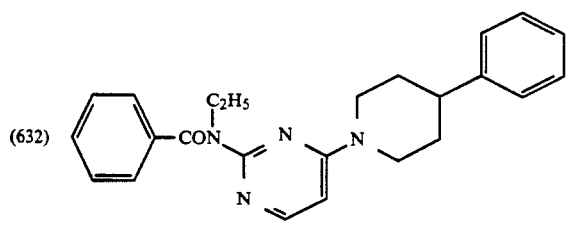
(636) p-Toluenesulfonate of (632)
(640) 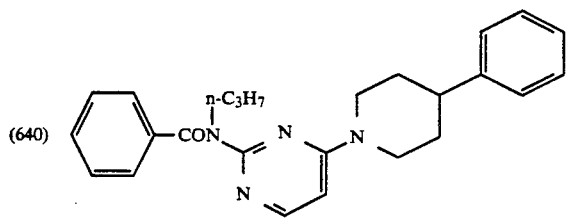
(644) p-Toluenesulfonate of (640)
(648) 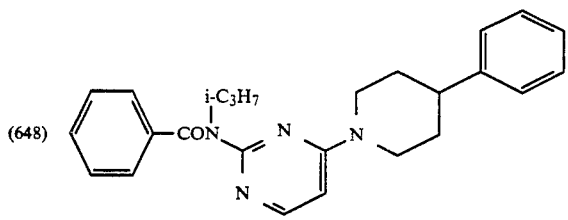
(652) p-Toluenesulfonate of (648)
(656) 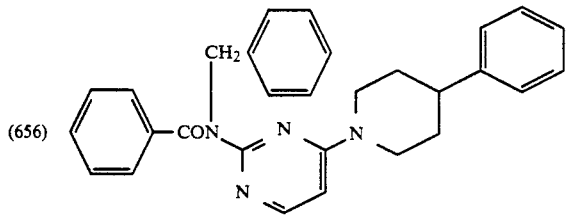
(660) p-Toluenesulfonate of (656)
(661) 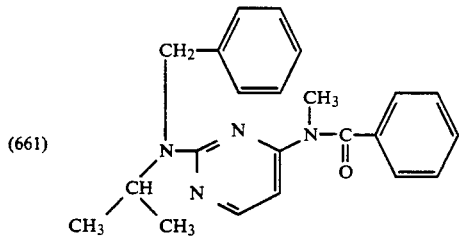
(662) Hydrochloride of (661)
(664) 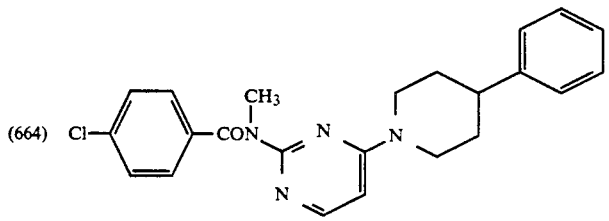
(668) p-Toluenesulfonate of (664)

(672) 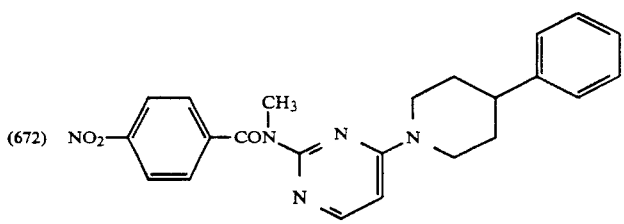
(676) p-Toluenesulfonate of (672)
(680) 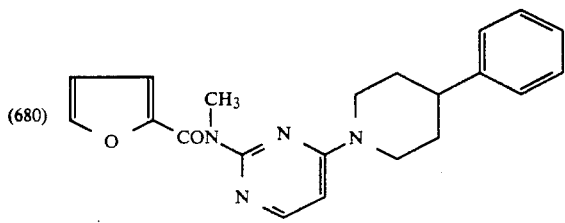
(684) p-Toluenesulfonate of (680)
(688) 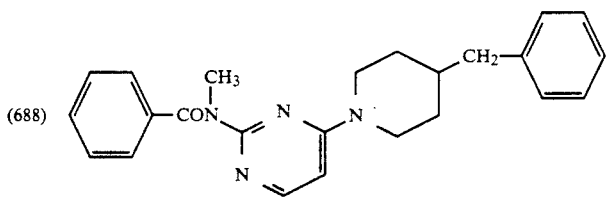
(692) p-Toluenesulfonate of (688)
(696) 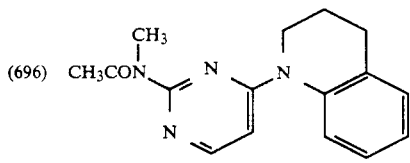
(700) p-Toluenesulfonate of (696)
(800) 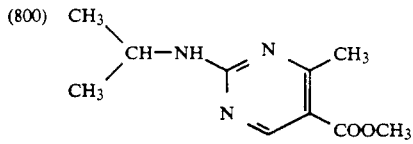
(804) Maleate of (800)
(808) 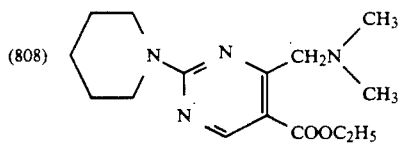
(812) Maleate of (808)
(816) 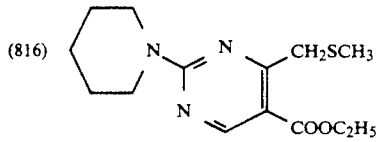

(820) 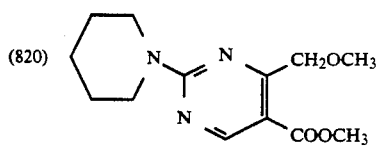
(824) 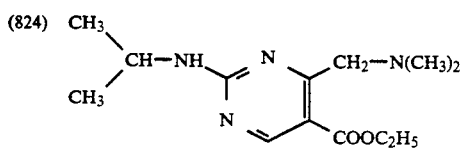
(828) Maleate of (824)
(2000) 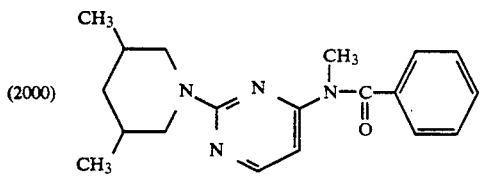
(2004) p-Toluenesulfonate of (2000)
(2008) 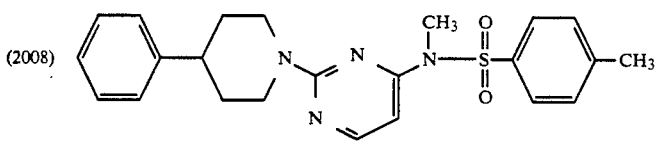
(2012) p-Toluenesulfonate of (2008)
(2016) 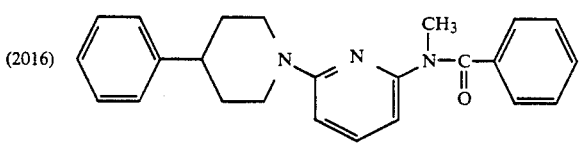
(2020) p-Toluenesulfonate of (2016)
(2022) 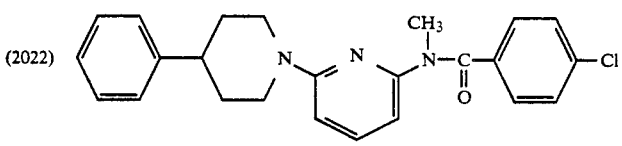
(2022-1) p-Toluenesulfonate of (2022)
(2023) 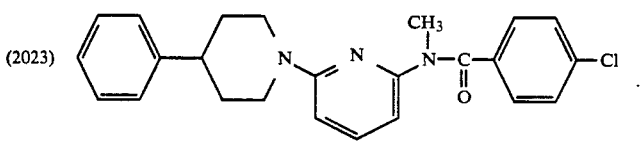
(2023-1) p-Toluenesulfonate of (2023)
(2024) 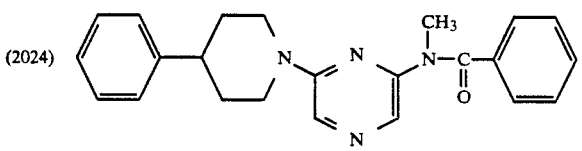
(2028) p-Toluenesulfonate of (2024)

(2032) 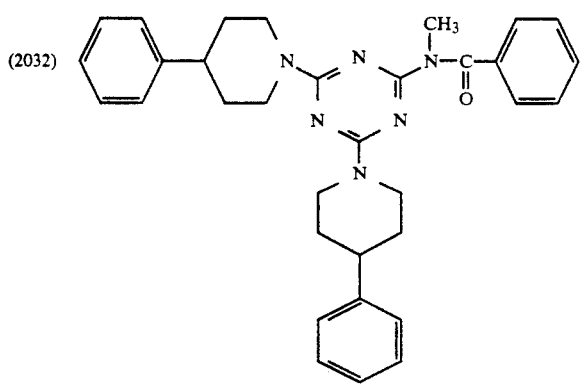
(2036) Di-p-toluenesulfonate of (2032)
(2040) 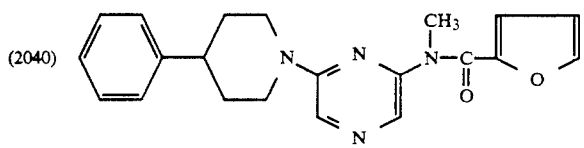
(2044) p-Toluenesulfonate of (2040)
(2048) 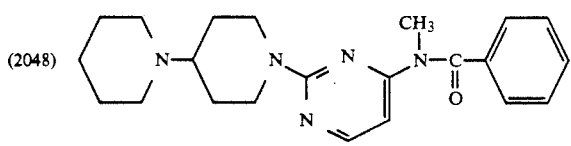
(2052) Dihydrochloride of (2048)
(2056) 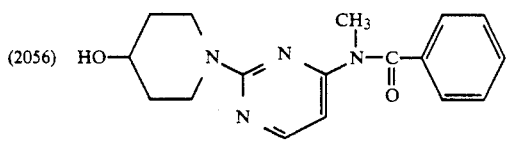
(2060) Hydrochloride of (2056)
(2064) 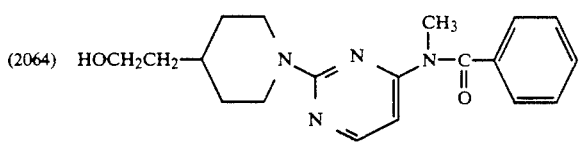
(2070) Hydrochloride of (2064)
(2074) 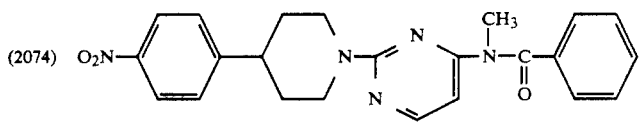
(2076) Hydrochloride of (2074)
(2080) 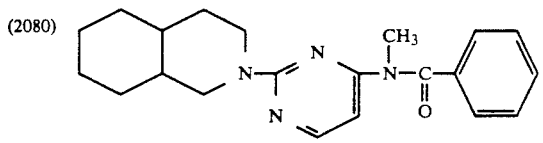
(2084) Hydrochloride of (2080)

-continued
(2088) 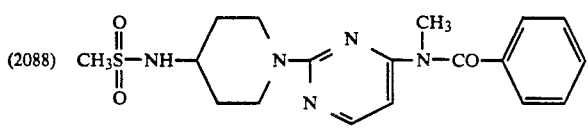
(2092) Hydrochloride of (2088)
(2096) 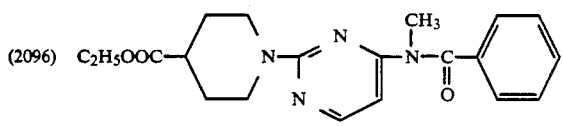
(2100) Hydrochloride of (2096)
(2104) 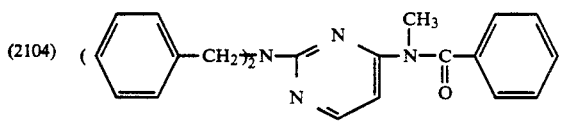
(2108) Hydrochloride of (2104)
(2112) 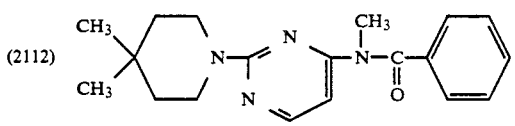
(2116) p-Toluenesulfonate of (2112)
(2120) 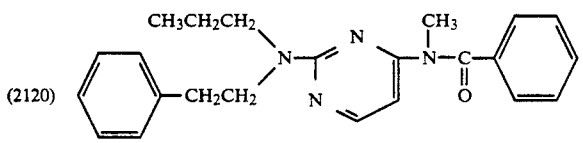
(2124) p-Toluenesulfonate of (2120)
(2128) 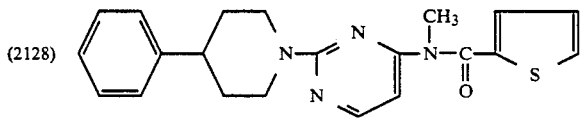
(2132) p-Toluenesulfonate of (2128)
(2136) 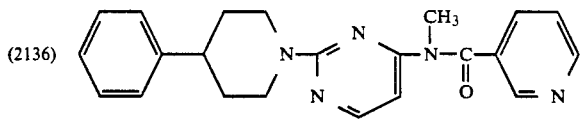
(2140) Di-p-toluenesulfonate of (2136)
(2144) 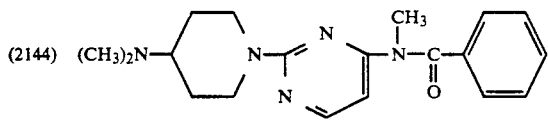
(2148) Dihydrochloride of (2144)
(2152) 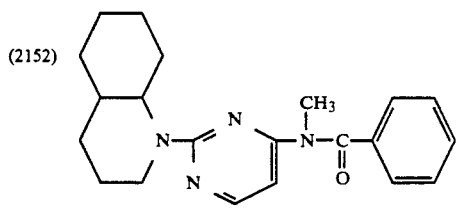

-continued
(2156) Hydrocholride of (2152)
(2160) 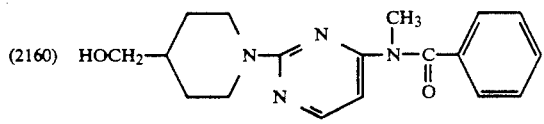
(2164) Dihydrochloride of (2160)
(2170) 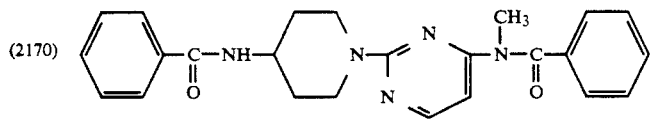
(2174) p-Toluenesulfonate of (2170)
(2178) 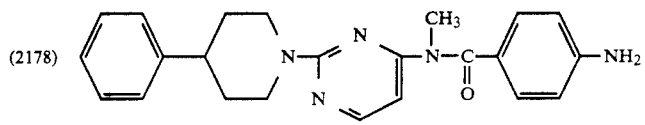
(2182) p-Toluenesulfonate of (2178)
(2184) 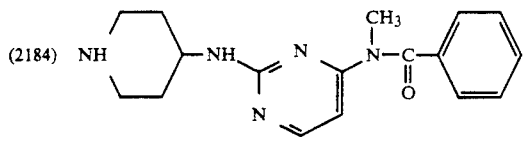
(2188) p-Toluenesulfonate of (2184)
(2192) 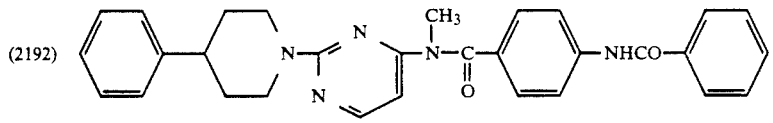
(2194) p-Toluenesulfonate of (2192)
(2198) 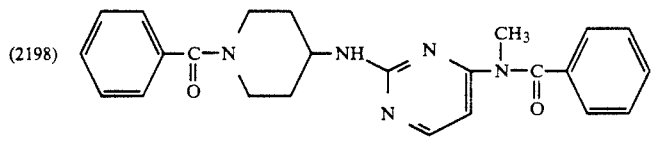
(2202) p-Toluenesulfonate of (2198)
(2206) 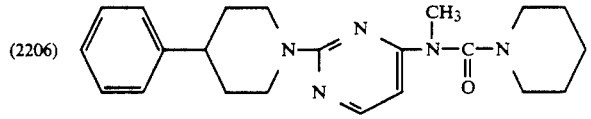
(2210) p-Toluenesulfonate of (2206)
(2214) 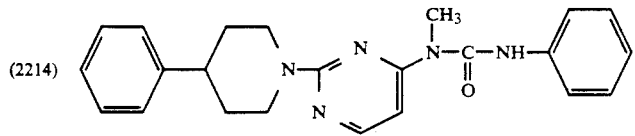
(2218) p-Toluenesulfonate of (2214)

(2222) 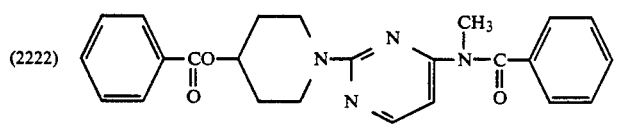
(2226) Hydrochloride of (2222)
(2230) 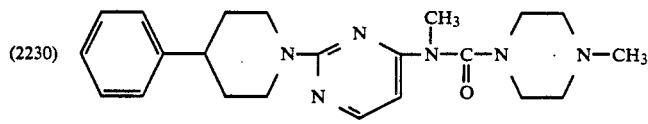
(2234) Di-p-toluenesulfonate of (2230)
(2238) 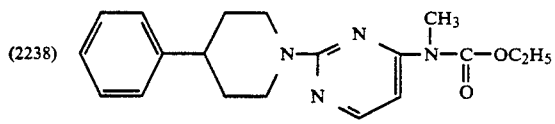
(2242) p-Toluenesulfonate of (2238)
(2246) 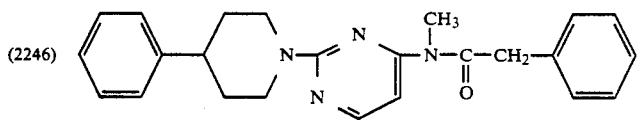
(2250) p-Toluenesulfonate of (2246)
(2254) 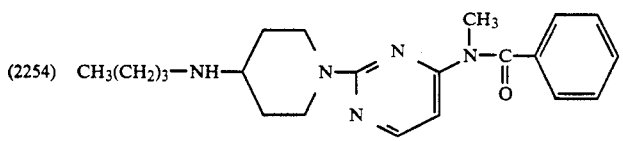
(2260) p-Toluenesulfonate of (2254)
(2264) 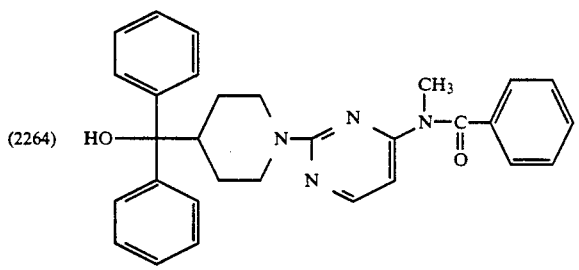
(2270) p-Toluenesulfonate of (2264)
(2274) 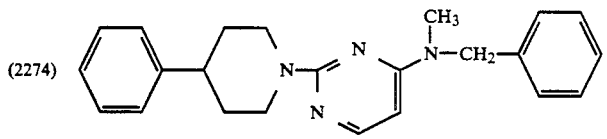
(2278) p-Toluenesulfonate of (2274)
(2282) 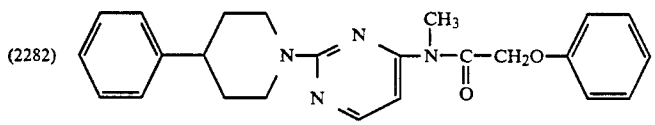
(2286) p-Toluenesulfonate of (2282)

(2290) 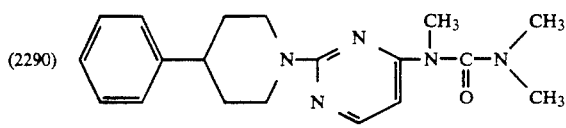
(2294) p-Toluenesulfonate of (2290)
(2298) 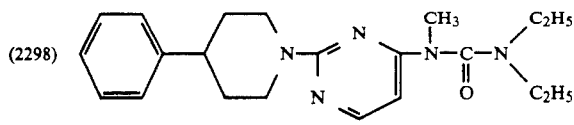
(2302) p-Toluenesulfonate of (2298)
(2306) 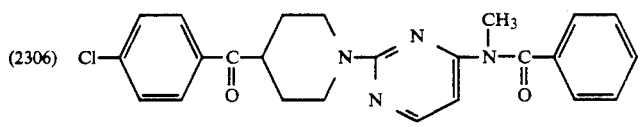
(2310) p-Toluenesulfonate of (2306)
(2314) 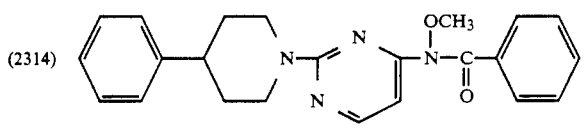
(2318) p-Toluenesulfonate of (2314)
(2322) 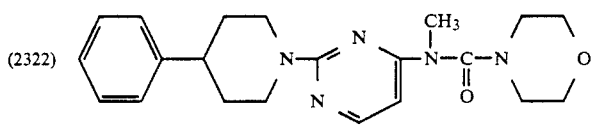
(2326) p-Toluenesulfonate of (2322)
(2330) 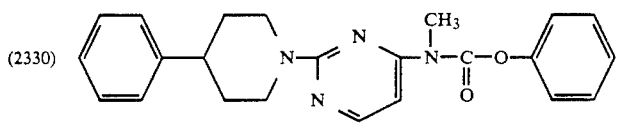
(2334) p-Toluenesulfonate of (2330)
(2338) 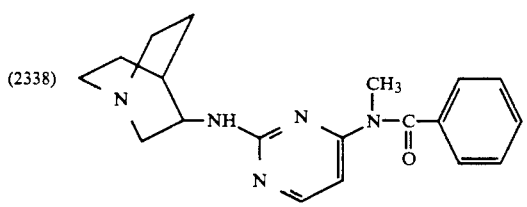
(2342) Dihydrochloride of (2338)
(2346) 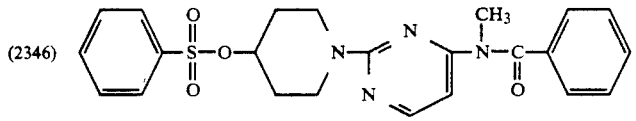
(2350) Hydrochloride of (2346)
(3100) 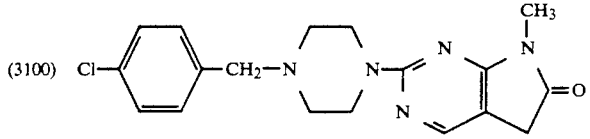

-continued
(3104) Hydrochloride of (3100)
(3108) 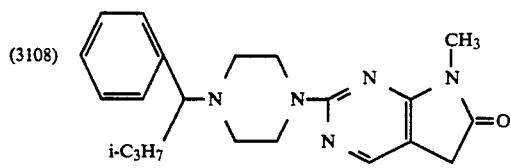
(3112) p-Toluenesulfonate of (3108)
(3116) 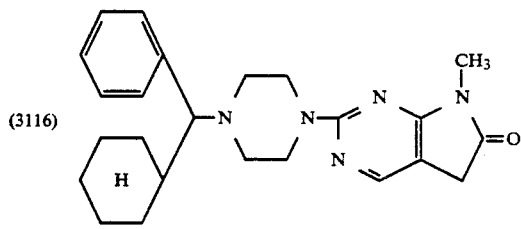
(3124) 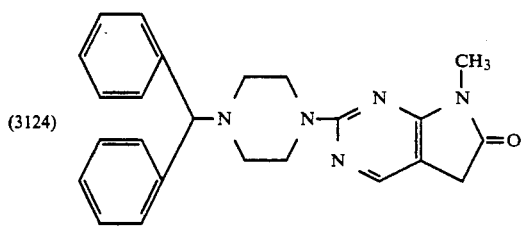
(3128) Hydrochloride of (3124)
(3132) 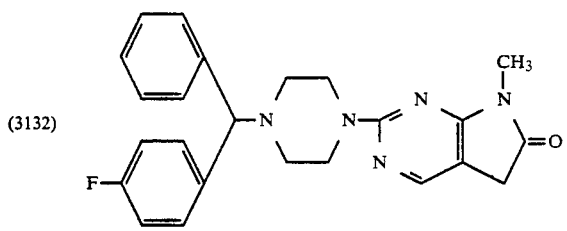
(3136) Hydrochloride of (3132)
(3140) 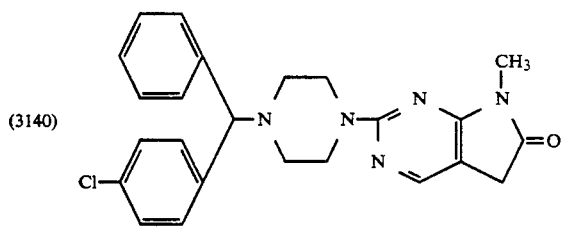
(3144) Hydrochloride of (3140)
(3148) 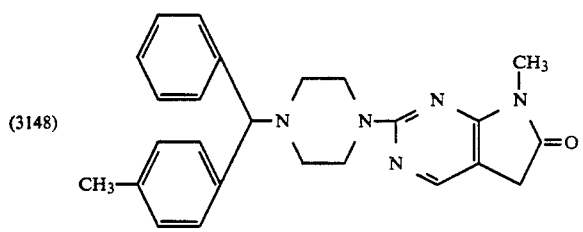
(3152) p-Toluenesulfonate of (3148)

-continued
(3156) 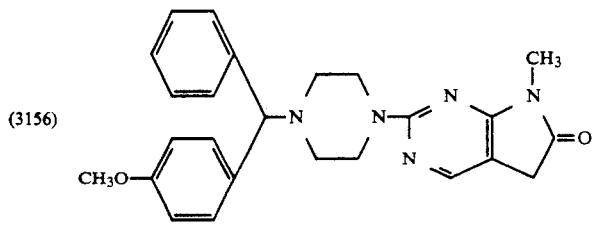
(3172) 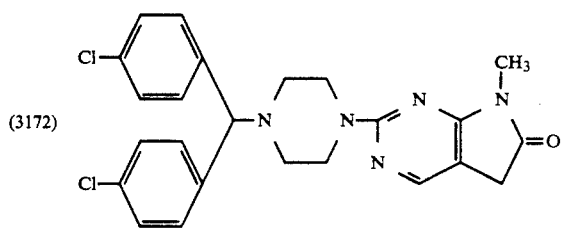
(3176) p-Toluenesulfonate of (3172)
(3180) 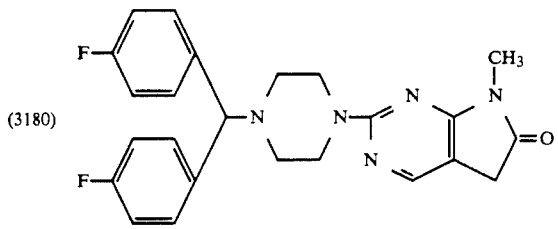
(3184) p-Toluenesulfonate of (3180)
(3188) 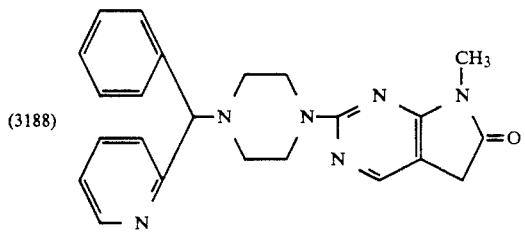
(3192) p-Toluenesulfonate of (3188)
(3196) 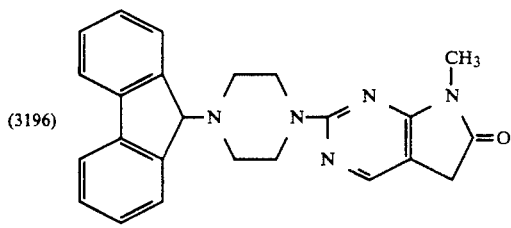
(3200) Hydrochloride of (3196)
(3300) 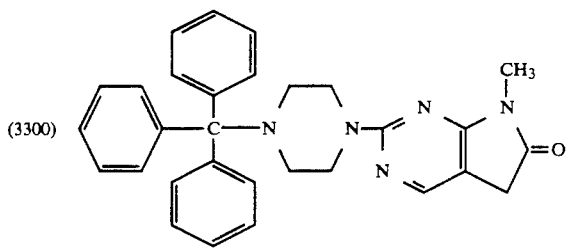

(3400) 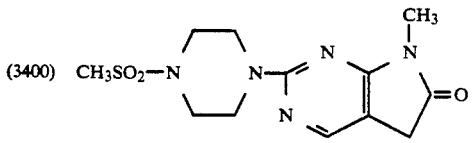

(3404) p-Toluenesulfonate of (3400)

(3408) 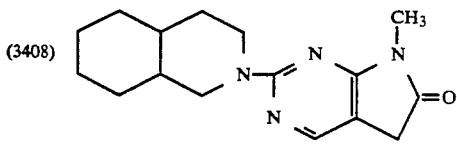

(3412) Hydrochloride of (3408)

(3416) 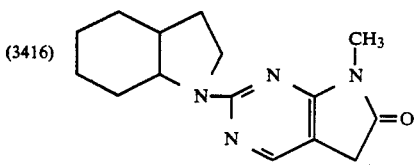

(3420) Hydrochloride of (3416)

The compounds of formulae (1), (2) and (3) may be produced by known methods, particularly the methods described in Japanese Laid-Open Patent Publication Nos. 140568/1986 and 87627/1986, or by treating the intermediates obtained by these methods in accordance with known methods (for example, the elimination of the protecting group by reduction). Examples 1 to 9 given hereinafter describe the production of these compounds in detail.

For example, compounds of formula (I) in which Y is $-NR^6R^7$ and $R^6$ is other than hydrogen may be produced by the following reaction scheme 1.

Reaction scheme 1

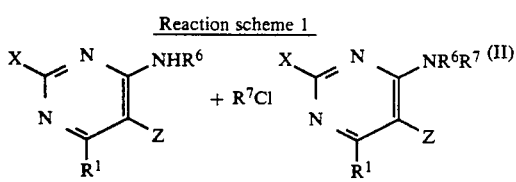

Compounds of general formula (1) in which X is $-NR^4R^5$ may be produced by the following reaction scheme 2.

Reaction scheme 2

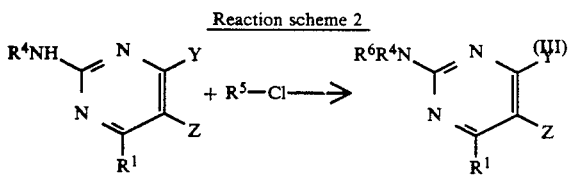

The starting compounds of formulae (II) and (III) in the reaction schemes 1 and 2 may be produced by the method described at J. Chem. Soc., 1965, pages 755-761, from

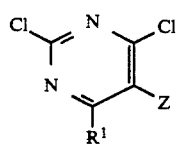

as a starting material. The reactions in the reaction schemes 1 and 2 are conveniently carried out at a temperature of 20° to 150° C. in a solvent such as toluene, dioxane, pyridine or water in the presence of, as required, a basic compound. The basic compound may conveniently be, for example, an organic base (such as triethylamine, pyridine and 4-dimethylaminopyridine), and an inorganic base (such as sodium carbonate and potassium carbonate).

Compounds of general formula (1) in which Y is $CH_2R^9$, $R^9$ is hydrogen or a lower alkyl group and Z is a lower alkoxycarbonyl group may be produced in accordance with the following reaction scheme 3.

Reaction scheme 3

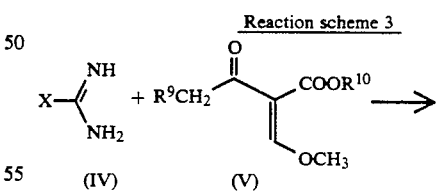

(I) (Y = $CH_2R^9$, Z = $COOR^{10}$)

Specifically, by reacting compounds (IV) with (V) at a temperature of 20° to 100° C. in a reaction medium such as water, methanol, ethanol, THF and DMF, compounds of formula (I) In which Y=$R^{10}$, and Z=$COOR^{13}$ are obtained.

Compounds of general formula (I) in which Y is $CH_2R^9$, $R^9$ is other than hydrogen and lower alkyl group and Z is a lower alkoxycarbonyl group may be produced in accordance with the reaction scheme 4.

Reaction scheme 4

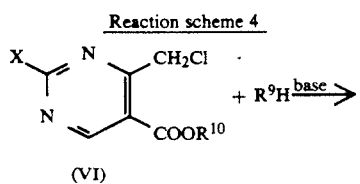

(I) (Y = CH$_2$R$^9$, Z = COOR$^{10}$)

Compound (VI) may be prepared in the same way as in Production Method No. 7] of Japanese Laid-Open Patent Publication No. 65873/1986 except that X is used instead of benzylpiperazine. Compounds of formula (I) in which Y is CH$_2$R$^9$ and Z is COOR$^{10}$ are obtained by reacting compound (VI) with R$^9$H in the presence of an organic base and as pyridine or triethylamine, or an inorganic base such as potassium carbonate, sodium carbonate, potassium hydroxide, sodium hydroxide, potassium hydride or sodium hydride in the presence of an inert solvent such as toluene or tetrahydrofuran or in the absence of solvent.

The compounds of general formula (2) can be synthesized by the same methods as in the synthesis of the compound of general formula (1).

The compounds of general formula (3) can be produced by the methods shown in the following schemes 5 and 6.

Reaction scheme 5

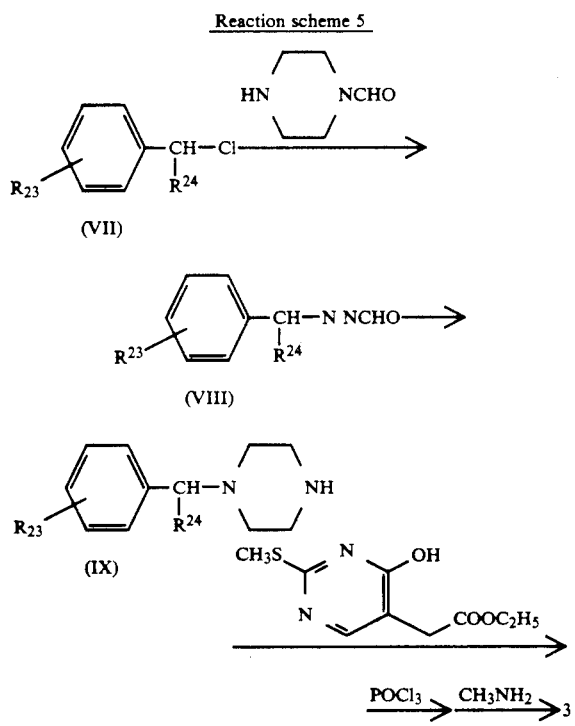

The starting material (VII) may be produced by the method described in J. A. C. S., 71, 2731 (1949). The reaction of the compound (VII) with N-formylpiperazine in a solvent such as acetonitrile or dimethylformamide or in the absence of solvent, optionally in the presence of a basic compound, at a temperature of 20° to 150° C., preferably 20° to 100° C., to form the compound (VIII). An inorganic base such as sodium carbonate or potassium carbonate, or an organic base such as triethylamine or pyridine may be used as the basic compound. Compound (III) is then hydrolyzed in the presence of an acid or an alkali to yield compound (IV). The hydrolysis is carried out in a solvent such as water, methanol or ethanol at a temperature of 0° to 150° C., preferably 20° to 100° C.

Reaction scheme 6

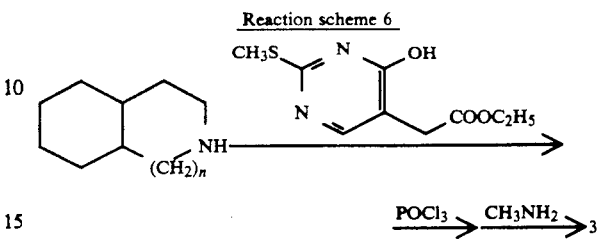

Compounds of formula (3) are produced from compound (IV) or (X) in accordance with scheme 5 by known methods, particularly the methods described in Japanese Laid-Open Patent Publications Nos. 140568/1986 and 87627/1986 or by treating the intermediates obtained by these methods in accordance with known methods (for example, the reductive elimination of the protective group). Examples 7 to 9 given below illustrate the production of the compounds of formula (3) in detail.

Investigations of the present inventors show that the compounds of formulae (1), (2) and (3) are useful as therapeutic agents for treatment of neurological diseases.

The compounds of formulae (1), (2) and (3) are normally used in the form of a pharmaceutical composition, and are administered by various routes (e.g., oral, subcutaneous, intramuscular, intravenous, intrahinal, skin permeation and through the rectum).

The present invention also embraces a pharmaceutical preparation comprising a compound of general formula (1), 2) or (3) or its pharmaceutically acceptable salt. The pharmaceutically acceptable salt includes, for example, acid addition salts and quaternary ammonium (or amine) salts.

Examples of the pharmaceutically acceptable salts of the compounds (1), (2) and (3) include salts formed from acids capable of forming pharmaceutically acceptable non-toxic acid-addition salts containing anions, such as hydrochlorides, hydrobromides, sulfates, bisulfites, phosphates, acid phosphates, acetates, maleates, fumarates, succinates, lactates, tartrates, benzoates, citrates, gluconates, glucanates, methanesulfonates, p-toluenesulfonates and naphthalenesulfonates or their hydrates, and quaternary ammonium (or amine) salts or their hydrates.

The composition of this invention may be formulated into tablets, capsules, powders, granules, troches, cachet wafer capsules, elixirs, emulsions, solutions, syrups, suspensions, aerosols, ointments, aseptic injectables, molded cataplasmas, tapes, soft and hard gelatin capsules, suppositories, and aseptic packed powders. Examples of the pharmaceutically acceptable carrier include lactose, glucose, sucrose, sorbitol, mannitol, corn starch, crystalline cellulose, gum arabic, calcium phosphate, alginates, calcium silicate, microcrystalline cellulose, polyvinyl pyrrolidone, tragacanth gum, gelatin, syrup, methyl cellulose, carboxymethyl cellulose, methylhydroxybenzoic acid esters, propylhydroxybenzoic acid esters, talc, magnesium stearates, inert polymers, water and mineral oils.

Both solid and liquid compositions may contain the aforesaid fillers, binders, lubricants, wetting agents, disintegrants, emulsifying agents, suspending agents, preservatives, sweetening agents and flavoring agents. The composition of this invention may be formulated such that after administration to a patient, the active compound is released rapidly, continuously or slowly.

In the case of oral administration, the compound of formula (1), (2) or (3) is mixed with a carrier or diluent and formed into tablets, capsules, etc. In the case of parenteral administration, the active ingredient is dissolved in a 10% aqueous solution of glucose, isotonic salt water, sterilized water or a like liquid, and enclosed in vials or ampoules for intravenous instillation or injection or intramuscular injection. Advantageously, a dissolution aid, a local anesthetic agent, a preservative and a buffer may also be included into the medium. To increase stability, it is possible to lyophilize the present composition after introduction into a vial or ampoule. Another example of parenteral administration is the administration of the pharmaceutical composition through the skin as an ointment or a cataplasm. In this case, a molded cataplasm or a tape is advantageous.

The composition of this invention contains 0.1 to 2000 mg, more generally 0.5 to 1000 mg, of the active component for each unit dosage form.

The compound of formula (1), (2) or (3) is effective over a wide dosage range. For example, the amount of the compound administered for one day usually falls within the range of 0.03 mg/kg to 100 mg/kg. The amount of the compound to be actually administered is determined by a physician depending, for example, upon the type of the compound administered, and the age, body weight, reaction condition, etc. of the patient and the administration route.

The above dosage range, therefore, does not limit the scope of the invention. The suitable number of administrations is 1 to 6, usually 1 to 4, daily.

The compound of formula (1), (2) or (3) by itself is an effective therapeutic agent for disorders of the peripheral nervous system and the central nervous system. If required, it may be administered in combination with at least one other equally effective drug. Examples of such an additional drug are gangliosides, mecobalamin and isaxonine.

The formulations of the compounds (1), (2) and (3) in accordance with this invention and their biological activities will be illustrated in detail by a series of Examples B and Examples given below. It should be understood however that they do not limit the scope of the invention. Each of the following examples showing the composition of the invention uses one of the compounds described hereinabove or one of other pharmaceutically active compounds encompassed within general formula (1), (2) and (3).

REFERENTIAL EXAMPLE 1

4-Methylamino-2-(4-Phenylpiperidino)Pyrimidine (Compound No. 1024)

To a solution of 17.0 g (0.11 mole) of 2,4-dichloropyrimidine in 150 ml of dichloromethane was added methylamine (0.25 mole, 20 ml of 40% methanol solution) at such a rate that the temperature of the solution was maintained at 5° C. After the addition, the solution was stirred at room temperature for 12 hours. The reaction mixture was concentrated under reduced pressure, and extracted with dichloromethane. The dichloromethane layer was dried over an anhydrous sodium sulfate, and concentrated under reduced pressure to give 14.0 g (purity 80%) of 2-chloro-4-methylaminopyrimidine.

Two hundred milliliters of n-butanol was added to 3.0 g (0.02 mole) of 2-chloro-4-methylaminopyrimidine and 8.4 g (0.05 mole) of 4-phenylpiperidine, and the mixture was heated at 130° C. for 1 hour. The reaction mixture was concentrated under reduced pressure, and extracted with dichloromethane. The dichloromethane layer was dried over anhydrous sodium sulfate, and concentrated under reduced pressure. The residue was purified by silica gel column chromatography to give 4.0 g (yield 71%) of the desired compound as an oil.

$^1$H-NMR spectrum (deuterochloroform, δ ppm): 1.4–2.0(5H, m), 2.93(3H, d, J=5.2 Hz), 2.6–3.1(2H, m), 4.60(1H, m), 4.92(2H, br. d, J=12.6 Hz), 5.67(1H, d, J=7.2 Hz), 7.28(5H, s), 7.93(1H, d, J=7.2 Hz).

In a similar manner, the following compounds were produced.

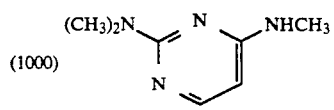
(1000)

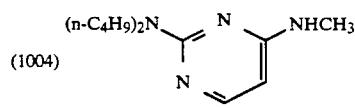
(1004)

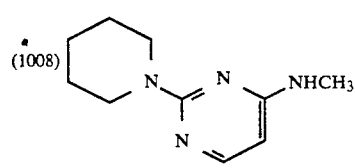
(1008)

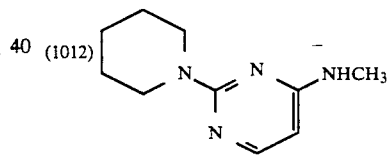
(1012)

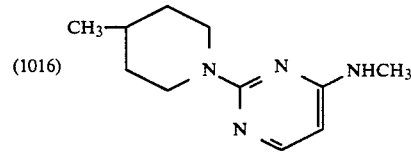
(1016)

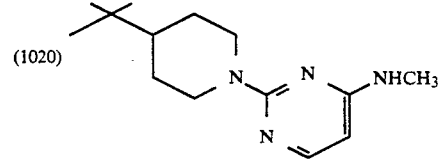
(1020)

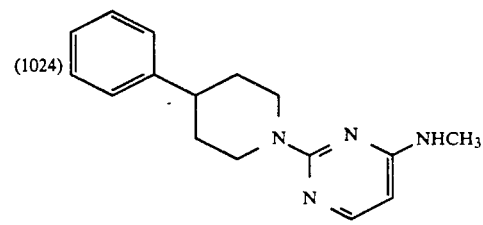
(1024)

(1028) 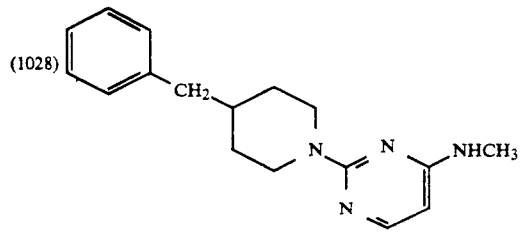
(1032) 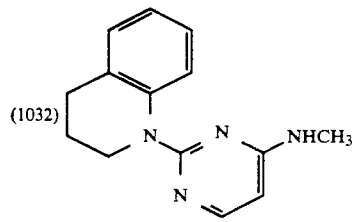
(1036) 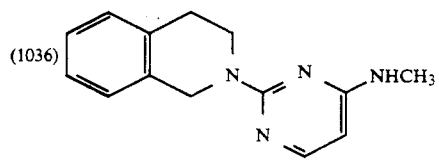
(1040) 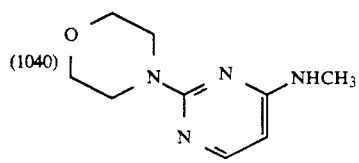
(1044) 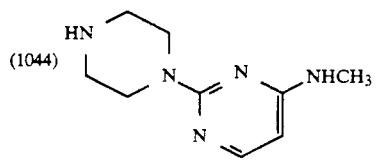
(1048) 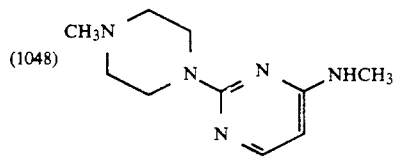
(1052) 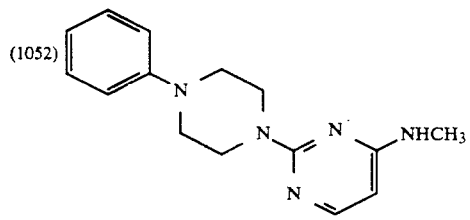
(1056) 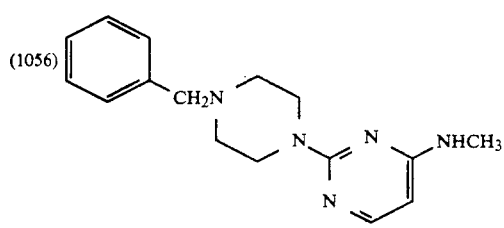
(1060) 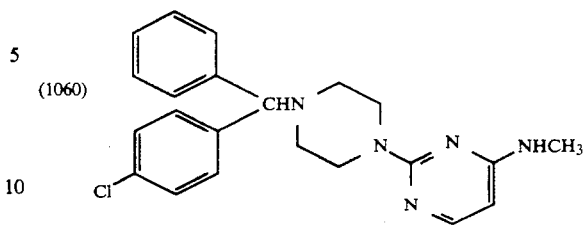
(1064) 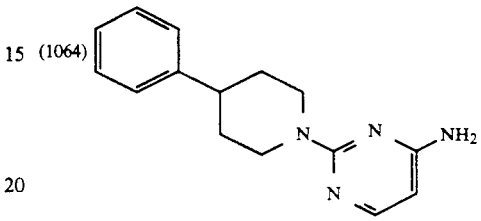
(1068) 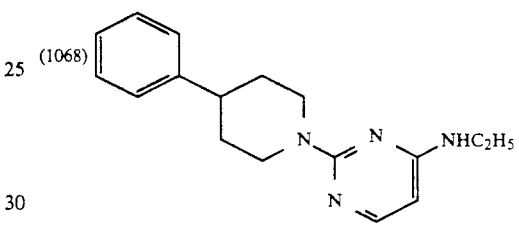
(1072) 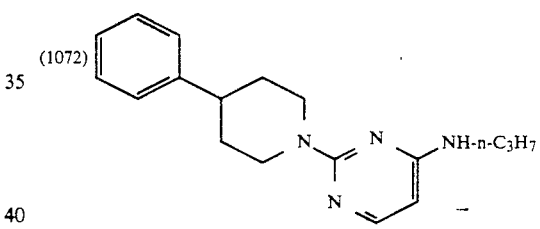
(1076) 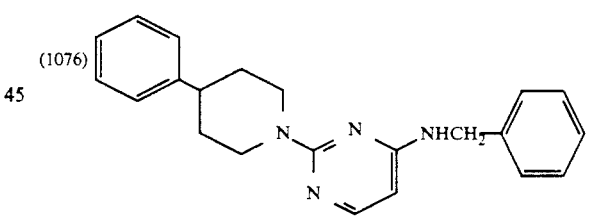
(1080) 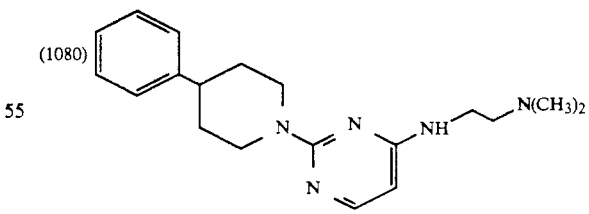
(1084) 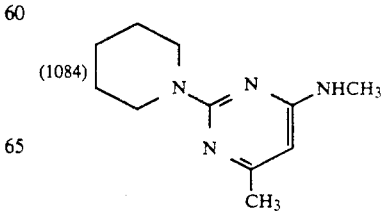

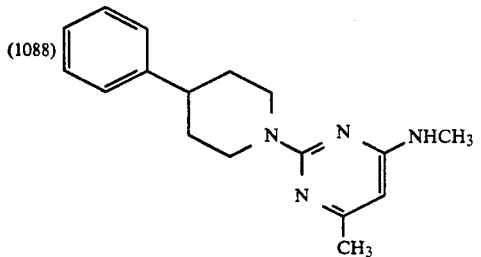
(1088)
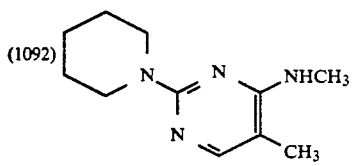
(1092)
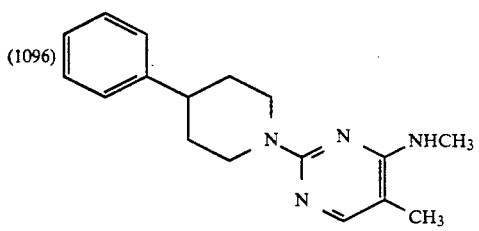
(1096)
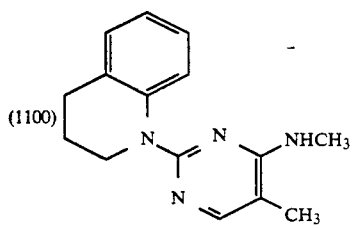
(1100)
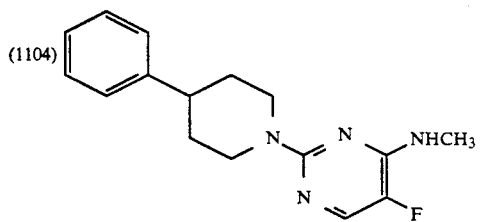
(1104)
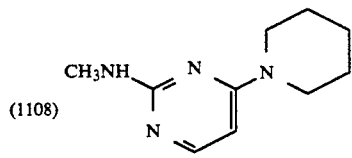
(1108)
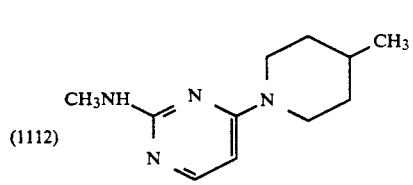
(1112)
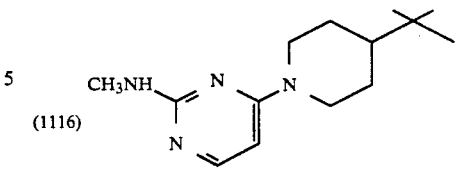
(1116)
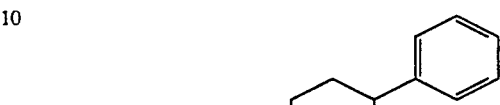
(1120)
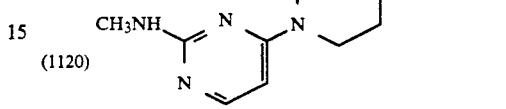
(1124)
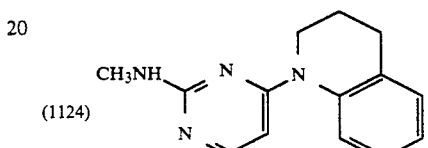
(1128)
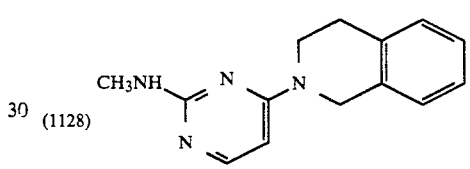
(1132)
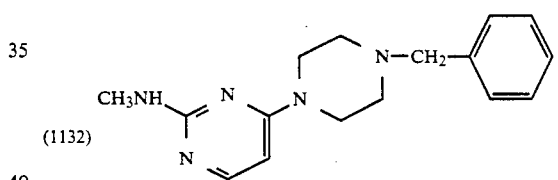
(1136)
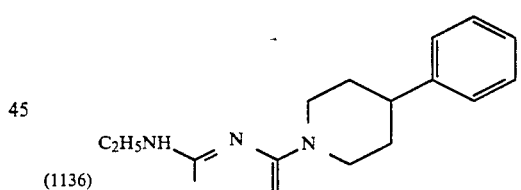
(1140)
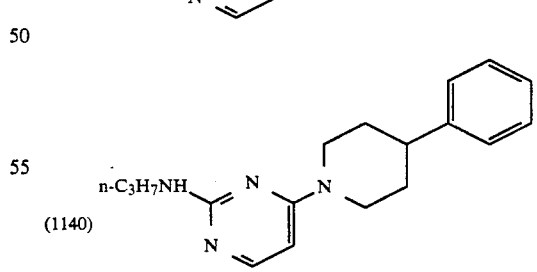
(1144)

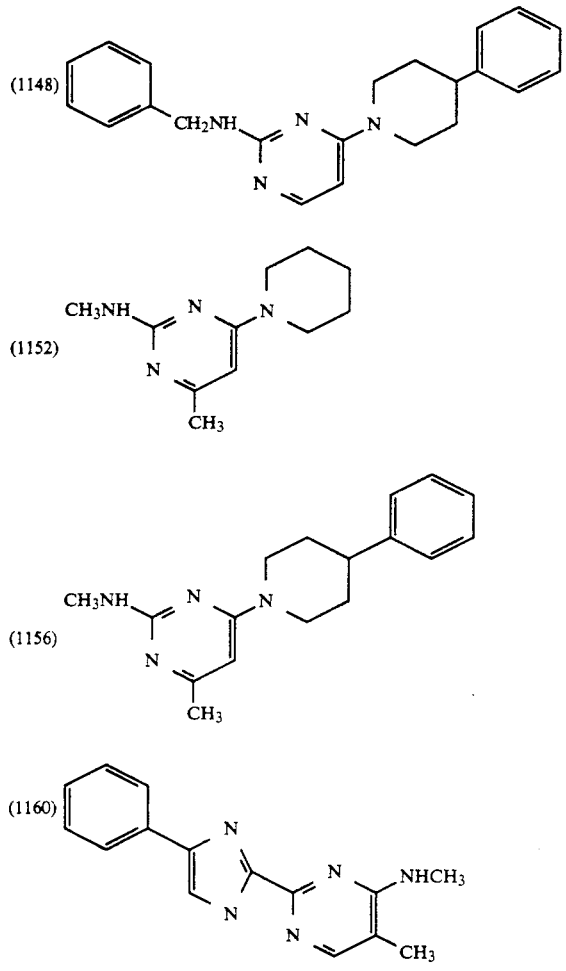

The properties of the compounds (intermediate) are shown in Table 1 below.

TABLE 1

| Compound No. | Yield (%) | Melting point (°C.) | 1H-NMR spectrum (CDCl3 solution, δ ppm) |
|---|---|---|---|
| 1000 | 51 | Oil | 2.90(3H, d, J=5.2Hz), 3.13(6H, s), 4.66(1H, m), 5.63(1H, d, J=5.2Hz), 7.88(1H, d, J=5.2Hz) |
| 1004 | 29 | Oil | 0.92(6H, m), 1.0–1.8(8H, m), 2.88(3H, d, J=5.2Hz), 3.51(4H, m), 4.55(1H, m), 5.56(1H, d, J=5.2Hz), 7.84(1H, d, J=5.2Hz) |
| 1008 | 68 | Oil | 1.92(4H, m), 2.88(3H, d, J=5.2Hz), 3.52(4H, m), 4.76(1H, m), 5.63(1H, d, J=5.2Hz), 7.88(1H, d, J=5.2Hz), |
| 1012 | 95 | Oil | 1.62(6H, br. s), 2.92(3H, d, J=5.4Hz), 3.72(4H, br. s), 4.60(1H, m), 5.64(1H, d, J=6.0Hz), 7.90(1H, d, J=6.0Hz) |
| 1016 | 72 | Oil | 0.95(3H, d, J=5.2Hz), 0.9–1.8(5H, m), 2.6–3.0(2H, m), 2.90(3H, d, J=5.2Hz), 4.69(2H, br. d, J=12.6Hz), 4.70(1H, m), 5.64(1H, d, J=5.2Hz), 7.89(1H, d, J=5.2Hz) |
| 1020 | 62 | Oil | 0.9(9H, s), 1.0–1.9(5H, m), 2.5–3.0(2H, m), 2.90(3H, d, J=5.2Hz), 4.6(1H, m), 4.80(2H, br. d, J=12.6Hz), 5.64(1H, d, J=5.2Hz), 7.9(1H, d, J=5.2Hz) |
| 1028 | 63 | Oil | 1.0–2.0(5H, m), 2.54(2H, d, J=5.2Hz), 2.4–3.0(2H, m), 2.87(3H, d, J=5.2Hz), 4.65(2H, m), 4.72(2H, br. d, J=12.6Hz), 5.62(1H, d, J=5.2Hz), 7.0–7.4(5H, m), 7.88(1H, d, J=5.2Hz) |
| 1032 | 66 | 96–98 | 1.7–2.2(2H, m), 2.8(2H, t, J=7.2Hz) 2.89(3H, d, J=5.2Hz), 4.02(2H, t, J=7.2Hz), 4.70(1H, m), 5.82(1H, d, J=5.2Hz), 6.8–7.3(3H, m), 7.82(1H, d, J=7.2Hz), 7.99(1H, d, J=5.2Hz) |
| 1036 | 77 | Oil | 2.92(5H, m), 4.02(2H, t, J=5.2Hz), 4.7(1H, m), 4.89(2H, s), 5.67(1H, d, J=7.2Hz), 7.18(4H, m), 7.94(1H, d, J=7.2Hz) |
| 1040 | 60 | Oil | 2.89(3H, d, J=5.2Hz), 3.73(8H, s), 4.70(1H, m), 5.69(1H, d, J=5.2Hz), 7.88(1H, d, J=5.2Hz) |
| 1048 | 56 | Oil | 2.32(3H, s), 2.43(4H, m), 2.88(3H, d, J=5.2Hz), 3.78(4H, m), 4.72(1H, m), 5.65(1H, d, J=5.2Hz), 7.86(1H, d, J=5.2Hz) |
| 1052 | 56 | 120–122 | 2.91(3H, d, J=4Hz), 3.24(4H, m), 3.95(4H, m), 4.60(1H, m), 5.70(1H, d, J=5.4Hz), 6.8–7.4(5H, m), 7.92(1H, d, J=5.4Hz) |
| 1056 | 68 | Oil | 2.48(4H, m), 2.87(3H, d, J=5.2Hz), 3.53(2H, s), 3.77(4H, m), 4.60(1H, m), 5.64(1H, d, J=5.2Hz), 7.32(5H, m), 7.87(1H, d, J=5.2Hz) |
| 1060 | 80 | Oil | 2.42(4H, m), 2.85(3H, d, J=5.6Hz), 3.76(4H, m), 4.24(1H, s), 4.56(1H, m), 5.65(1H, d, J=5.6Hz), 7.0–7.5(9H, m), 7.88(1H, d, J=5.6Hz) |
| 1064 | 61 | Oil | 1.4–2.2(4H, m), 2.5–3.1(3H, m), 4.62(2H, br. s), 4.88(2H, br. d, J=12.6Hz), 5.72(1H, d, J=5.2Hz), 7.25(5H, m), 7.94(1H, d, J=5.2Hz) |
| 1068 | 58 | Oil | 1.24(3H, t, J=7.2Hz), 1.4–2.0(4H, m), 2.5–3.1(3H, m), 3.1–3.5(2H, m), 4.58(1H, m), 4.90(2H, br. d, J=12.6Hz), 5.65(1H, d, J=5.2Hz), 7.0–7.5(5H, m), 7.92(1H, d, J=5.2Hz) |
| 1072 | 75 | Oil | 0.97(3H, t, J=7.2Hz), 1.4–2.1(6H, m), 2.5–3.1(3H, m), 3.24(2H, q, J=7.2Hz), 4.68(1H, br. s), 4.88(2H, br. d, J=12.6Hz), 5.65(1H, d, J=5.2Hz), 7.27(5H, m), 7.90(1H, d, J=5.2Hz) |
| 1076 | 57 | Oil | 1.4–2.0(4H, m), 2.5–3.1(3H, m), 4.52(2H, d, J=5.2Hz), 4.90(2H, br. d, J=12.6Hz), 4.91(1H, m), 5.68(1H, d, J=5.2Hz), 7.0–7.5(10H, m), 7.92(1H, d, J=5.2Hz) |
| 1080 | 36 | Oil | 1.4–2.0(4H, m), 2.27(6H, s), 2.50(2H, m), 2.5–3.2(3H, m), 3.36(2H, m), 3.46(2H, s), 4.90(2H, br. d, J=12.6Hz), 5.24(1H, m), 5.67(1H, d, J=5.2Hz), 7.27(5H, m), 7.88(1H, d, J=5.2Hz) |
| 1084 | 50 | 91–93 | 1.60(6H, br. s), 2.23(3H, s), 2.88(3H, d, J=5.2Hz), 3.75(4H, br. s), 4.50(1H, m), 5.54(1H, s) |
| 1088 | 57 | Oil | 1.5–2.0(4H, m), 2.23(3H, s), 2.6–3.0(3H, m), |

TABLE 1-continued

| Compound No. | Yield (%) | Melting point (°C.) | ¹H-NMR spectrum (CDCl₃ solution, δ ppm) |
|---|---|---|---|
| 1092 | 21 | Oil | 2.90(3H, d, J=5.2Hz), 4.51(1H, m), 4.96(2H, br. d, J=12.6Hz), 5.57(1H, s), 7.28(5H, s) 1.60(6H, br. s), 1.88(3H, s), 3.0(3H, d, J=5.2Hz), 3.75(4H, br. s), 4.2(1H, br. s), 7.65(1H, s) |
| 1096 | 75 | Oil | 1.4-2.0(4H, m), 1.92(3H, s), 2.5-3.1(3H, m), 3.02(3H, d, J=5.2Hz), 4.40(1H, m), 4.90(2H, br. d, J=12.6Hz), 7.28(5H, m), 7.68(1H, s) |
| 1100 | 81 | Oil | 1.8-2.1(5H, m), 2.79(2H, t, J=7.2Hz), 2.99(3H, d, J=5.2Hz), 4.03(2H, t, J=7.2Hz), 4.42(1H, m), 6.8-7.2(3H, m), 7.7-8.0(2H, m) |
| 1104 | 48 | 121-124 | 1.4-2.1(4H, m), 2.5-3.1(3H, m), 3.02(3H, d, J=4.0Hz), 4.85(1H, m), 4.88(2H, br. d, J=12.6Hz), 7.28(5H, m), 7.75(1H, d, J=4.0Hz) |
| 1112 | 24 | 117-118 | 0.96(3H, d, J=5.2Hz), 0.9-1.8(5H, m), 2.6-3.0(2H, m), 2.96(3H, d, J=5.2Hz), 4.32(2H, br. d, J=12.6Hz), 4.80(1H, m), 5.88(1H, d, J=5.2Hz), 7.87(1H, d, J=5.2Hz) |
| 1116 | 16 | 179-180 | 0.89(9H, s), 1.0-1.9(5H, m), 2.5-3.0(2H, m), 2.95(3H, d, J=5.2Hz), 4.45(2H, br. d, J=12.6Hz), 4.75(1H, m), 5.89(1H, d, J=5.2Hz), 7.88(1H, d, J=5.2Hz) |
| 1120 | 18 | 148-154 | 1.4-2.1(5H, m), 2.97(3H, d, J=5.2Hz), 2.6-3.1(2H, m), 4.53(2H, br. d, J=12.6Hz), 5.95(1H, d, J=7.2Hz), 7.28(5H, s), 7.88(1H, d, J=7.2Hz) |
| 1124 | 20 | 175-176 | 1.8-2.1(2H, m), 2.76(2H, t, J=7.2Hz), 2.99(3H, d, J=5.2Hz), 3.96(2H, t, J=7.2Hz), 4.9(1H, m), 6.32(1H, d, J=5.2Hz), 6.9-7.5(4H, m), 7.88(1H, d, J=5.2Hz) |
| 1128 | 19 | 123-126 | 2.90(5H, m), 3.83(2H, t, J=5.2Hz), 4.72(2H, s), 4.90(1H, m), 5.92(1H, d, J=7.2Hz), 7.19(4H, s), 7.92(1H, d, J=7.2Hz) |
| 1132 | 17 | — | 2.47(4H, m), 2.92(3H, d, J=5.2Hz), 3.52(2H, s), 3.59(4H, m), 4.75(1H, m), 5.84(1H, d, J=5.2Hz), 7.31(5H, m), 7.85(1H, d, J=5.2Hz) |
| 1136 | 17 | 158-160 | 1.24(3H, t, J=7.2Hz), 1.5-2.1(4H, m), 2.5-3.2(3H, m), 3.2-3.6(2H, m), 4.52(2H, br. d, J=12.6Hz), 4.70(1H, m), 5.92(1H, d, J=5.2Hz), 7.0-7.5(5H, m), 7.89(1H, d, J=5.2Hz) |
| 1140 | 18 | 134-136 | 0.98(3H, t, J=7.2Hz), 1.4-2.1(6H, m), 2.6-3.1(3H, m), 3.35(2H, q, J=7.2Hz), 4.53(2H, br. d, J=12.6Hz), 4.80(1H, br. s), 5.93(1H, d, J=5.2Hz), 7.29(5H, m), 7.90(1H, d, J=5.2Hz) |
| 1144 | 13 | 158-160 | 1.2(3H, s), 1.27(3H, s), 1.4-2.0(4H, m), 2.2-3.1(3H, m), 3.9-4.3(1H, m), 4.52(2H, br. d, J=12.6Hz), 4.65(1H, m), 5.9(1H, d, J=5.2Hz), 7.0-7.5(5H, m), 7.89(1H, d, J=5.2Hz) |
| 1148 | 21 | 148-149 | 1.3-2.05(4H, m), 2.5-3.1(3H, m), 4.50(2H, br. d, J=12.6Hz), 4.60(2H, br. d, J=5.2Hz), 5.35(1H, m), 5.95(1H, d, J=5.2Hz), 7.0-7.5(10H, m), 7.88(1H, d, J=5.2Hz) |
| 1152 | 31 | 148-149 | 1.65(6H, br. s), 2.22(3H, s), 2.95(3H, d, J=5.2Hz), 3.57(4H, br. s), 4.75(1H, m), 5.77(1H, s) |
| 1156 | 10 | 198-199 | 1.5-2.0(4H, m), 2.23(3H, s), 2.6-3.1(3H, m), 2.96(3H, d, J=5.2Hz), 4.4-4.8(3H, m), 5.83(1H, s), 7.26(5H, m) |
| 1160 | 83 | 162-165 | 2.03(3H, s), 3.12(3H, d, J=5.2Hz), 4.90(1H, m), 7.2-7.5(3H, m), 7.85(3H, m), 8.12(1H, s), 8.6(1H, s) |

REFERENTIAL EXAMPLE 2

4-Methylamino-2-(4-Phenylpiperidino)Pyrimidine Maleate (Compound No. 1026)

A solution of 0.43 g (3.73 mmoles) of maleic acid in 10 ml of methanol was added to a solution of 1.0 g (3.73 mmoles) of 4-methylamino-2-(4-phenylpiperidino)-pyrimidine in 10 ml of methanol, and the mixture was stirred at room temperature for 1 hour. The mixed solution was concentrated under reduced pressure and washed with ether to give 1.25 g (yield 87%) of the desired product.

Melting point: 163°-166° C.

¹H-NMR spectrum (CDCl₃ solution, δ ppm): 1.6-2.2 (4H. m). 2.6-3.3(5H, m), 3.04(3H. d. J=5.2 Hz), 4.74(1H, br. d, J=12.6 Hz), 6.30(1H, d, J=7.2 Hz), 7.30(5H, m), 7.71(1H, d, J=7.2 Hz), 8.40(1H, m).

Similarly, the folllowing compounds were produced.

(1014): maleate of (1012)
(1026): maleate of (1024)
(1034): maleate of (1032)
(1038): maleate of (1036)
(1086): maleate of (1084)
(1090): maleate of (1088)
(1094): maleate of (1092)
(1098): maleate of (1096)
(1102): maleate of (1100)
(1110): maleate of (1108)
(1122): maleate of (1120)
(1130): maleate of (1128)
(1158): maleate of (1156)
(1162): maleate of (1160)

The data of these compounds are given in Table 2 below.

TABLE 2

| Compound No. | Yield (%) | Melting point (°C.) | 1H-NMR spectrum (CDCl3 solution, δ ppm) |
|---|---|---|---|
| 1014 | 89 | 164-165 | 1.70(6H, br. s), 3.02(3H, d, J=3.8Hz), 3.76(4H, br. s), 6.35(2H, s), 7.65(1H, m), 8.32(1H, m), |
| 1034 | 94 | 42-46 | 1.9-2.3(2H, m), 2.79(2H, t, J=7.2Hz), 3.01(3H, d, J=5.2Hz), 4.0(2H, t, J=7.2Hz), 6.22(2H, s), 6.46(1H, d, J=5.2Hz), 7.20(3H, m), 7.50(1H, m), 7.76(1H, d, J=5.2Hz), 8.80(1H, m) |
| 1038 | 77 | 149-151 | 2.9-3.2(5H, m), 4.0(2H, t, J=7.2Hz), 4.92(2H, s), |

TABLE 2-continued

| Compound No. | Yield (%) | Melting point (°C.) | 1H-NMR spectrum (CDCl3 solution, δ ppm) |
|---|---|---|---|
| | | | 6.32(1H, d, J=7.2Hz), 6.36(2H, s), 7.25(4H, s), 7.75(1H, d, J=7.2Hz), 8.40(1H, m) |
| 1086 | 99 | 155–157 | 1.68(6H, br. s), 2.28(3H, s), 3.0(3H, d, J=5.2Hz), 3.80(4H, br. s), 6.0(1H, s), 6.33(2H, s), 8.15(1H, m), 11.7(1H, m) |
| 1090 | 91 | 151–154 | 1.5–2.2(4H, m), 2.29(3H, s), 2.6–3.3(6H, m), 4.81(2H, br. d, J=12.6Hz), 6.02(1H, s), 6.32(2H, s), 7.28(5H, br. s), 8.15(1H, m), 12.2(1H, m) |
| 1094 | 91 | 150–152 | 1.70(6H, br. s), 2.04(3H, s), 3.08(3H, d, J=5.2Hz), 3.76(4H, br. s), 6.33(2H, s), 7.15(1H, m), 7.59(1H, s) |
| 1098 | 92 | 163–165 | 1.6–2.2(4H, m), 2.03(3H, s), 2.6–3.3(3H, m), 3.09(3H, d, J=5.2Hz), 4.71(2H, br. d, J=12.6Hz), 6.33(2H, s), 7.0–7.4(5H, m), 7.60(1H, s) |
| 1102 | 81 | 145–150 | 1.8–2.3(5H, m), 2.80(2H, t, J=5.2Hz), 3.08(3H, d, J=5.2Hz), 4.0(2H, t, J=5.2Hz), 6.25(2H, s), 7.1–7.6(4H, m), 7.70(1H, s) |
| 1110 | 91 | 187–188 | 1.74(6H, br. s), 2.32(3H, s), 2.96(3H, d, J=5.2Hz), 3.5(2H, br. s), 3.95(2H, br, s), 5.83(1H, s), 6.33(2H, s), 9.10(1H, m), 13.8(1H, m) |
| 1122 | 92 | 155–158 | 1.6–2.2(4H, m), 3.0(3H, d, J=5.2Hz) 2.7–3.5(3H, m), 4.10(1H, br. d, J=12.6Hz), 5.25(1H, br. d, J=12.6Hz), 6.12(1H, d, J=7.2Hz), 6.33(2H, s), 7.30(5H, m), 7.50(1H, d, J=7.2Hz), 9.0(1H, br. s) |
| 1130 | 87 | 158–159 | 2.9–3.2(5H, d, J=5.2Hz), 3.79(1H, t, J=5.2Hz), 4.16(1H, t, J=5.2Hz), 4.70(1H, s), 5.20(1H, s), 6.15(1H, br. d, J=7.2Hz), 6.30(2H, s), 7.27(4H, s), 7.52(1H, d, J=7.2Hz), 9.1(1H, m) |
| 1158 | 95 | 173–175 | 1.6–2.2(4H, m), 2.32(3H, s), 2.6–3.5(6H, m), 4.1(1H, m), 5.2(1H, m), 5.88(1H, s), 6.34(2H, s), 7.30(5H, br. s), 9.20(1H, m), 13.9(1H, m) |
| 1162 | 74 | 179–180 | 2.11(3H, s), 3.11(3H, d, J=7.2Hz), 6.32(2H, s), 6.50(1H, m), 7.2–8.0(6H, m), 8.20(1H, s), 8.84(1H, s) |

REFERENTIAL EXAMPLE 3

1-Diphenylmethylpiperazine 11.2 g (98 mmoles) of 1-formylpiperazine was added to 10 g (49 mmoles) of chlorodiphenylmethnae, and the solution was stirred at room temperature for 48 hours, and the mixture was extracted with water and methylene chloride. The organic layer was dried over anhydrous magnesium sulfate, and the solvent was evaporated under reduced pressure. The residue was purified by silica gel column chromatography, and 8.9 g (31.9 mmoles) of the resulting formyl compound was dissolved in 100 ml of ethanol, and 6.5 g (64 mmoles) of conc. hydrochloric acid was added, and the solution was refluxed for 1 hour. Then, the solvent was evaporated under reduced pressure, and the residue was extracted with $K_2CO_3$/water/$CH_2Cl_2$. The organic layer was dried over anhydrous magnesium sulfate, and the solvent was evaporated under reduced pressure to give 6.8 g (yield 55%) of the desired product.

Melting point: 93°–95° C.

1H-NMR spectrum ($CDCl_3$ solution, δ ppm): 2.33(4H, m), 2.87(4H, m), 4.19(1H, s), 7.1–7.5 (10H, m).

EXAMPLE 1

4-(N-Methylbenzamino)-2-(4-Phenylpiperidino)Pyrimidine (Compound No. 164)

A solution of 5.2 g (0.037 mole) of benzoyl chloride in 50 ml of tetrahydrofuran was added at room temperature over 30 minutes to a solution of 9.0 g (0.034 mole) of 4-methylamino-2-(4-phenylpiperidino)pyrimidine in 90 ml of tetrahydrofuran and 5 ml of triethylamine. TWo hours after the end of the addition, 1 ml of pyridine was added. The mixture was then stirred for 2 days. The reaction mixture was extracted with dichloromethane. The dicloromethane layer was dried over anhydrous sodium sulfate, and concentrated under reduced pressure. The residue was purified by silica gel column chromatography to give 8.8 g (yield 70%) of the desired compound as an oil.

1H-NMR spectrum (deuterochloroform, δ ppm): 1.4–2.0(4H, m), 2.5–3.0(3H, m), 3.55(3H, s), 4.62(2H, br. d, J=12.6 Hz), 6.14(1H, d, J=7.2 Hz), 7.1–7.6(10H, m), 8.06(1H, d, J=7.2 Hz).

Data of compounds produced in the same way as above are shown in Table 3 below.

TABLE 3

| Compound No. | Yield (%) | Melting point (°C.) | 1H-NMR spectrum (CDCl3 solution, δ ppm) |
|---|---|---|---|
| 100 | 48 | Oil | 3.0(6H, s), 3.52(3H, s), 6.04(1H, d, J=5.2Hz), 7.1–7.5(5H, m), 7.98(1H, d, J=5.2Hz) |
| 108 | 30 | Oil | 0.93(6H, m), 1.0–1.7(8H, m), 3.2–3.65(4H, m), 3.50(3H, s), 6.04(1H, d, J=5.2Hz), 7.1–7.6(5H, m), 7.96(1H, d, J=5.2Hz) |
| 116 | 41 | Oil | 1.92(4H, m), 3.38(4H, m), 3.53(3H, m), 6.0(1H, d, J=5.2Hz), 7.2–7.5(5H, m), 7.96(1H, d, J=5.2Hz) |
| 124 | 63 | Oil | 1.67(6H, br. s), 2.35(3H, s), 3.38(3H, s), 3.78(4H, m), 6.52(1H, d, J=6.0Hz), 8.25(1H, d, J=6.0Hz) |
| 132 | 55 | Oil | 1.55(6H, m), 3.53(3H, s), 3.56(4H, m), 6.08(1H, d, J=5.2Hz), 7.40(5H, m), 8.04(1H, d, J=5.2Hz) |
| 140 | 71 | Oil | 1.92(3H, d, J=5.2Hz), 0.8–1.8(5H, m), 2.7(2H, m), 3.52(3H, s), 4.44(2H, br. d, J=12.6Hz), 6.08(1H, d, J=5.2Hz), 7.40(5H, m), 8.04(1H, d, J=5.2Hz) |
| 148 | 34 | Oil | 0.88(9H, s), 1.0–1.8(5H, m), 2.63(2H, m), 3.53(3H, s), 4.55(2H, br. d, J=12.6Hz), 6.08(1H, d, J=5.2Hz), 7.2–7.7(5H, m), 8.05(1H, d, J=5.2Hz) |
| 156 | 71 | Oil | 1.4–2.0(4H, m), 2.5–3.2(3H, m), 4.91(2H, br. d, J=12.6Hz), 7.0–7.7(7H, m), 7.90(2H, m), 8.32(2H, m) |
| 172 | 20 | Oil | 1.33(3H, t, J=7.2Hz), 1.4–2.0(4H, m), 2.5–3.0(3H, m), |

TABLE 3-continued

| Compound No. | Yield (%) | Melting point (°C.) | $^1$H-NMR spectrum (CDCl$_3$ solution, δ ppm) |
|---|---|---|---|
| | | | 4.13(2H, q, J=7.2Hz), 4.64(2H, br. d, J=12.6Hz), 6.01(1H, d, J=5.2Hz), 7.0–7.7(10H, m,), 8.04(1H, d, J=5.2Hz) |
| 180 | 37 | Oil | 0.98(3H, t, J=7.2Hz), 1.3–2.0(6H, m), 2.5–3.01(3H, m), 4.03(2H, t, J=7.2Hz), 4.63(2H, br. d, J=12.6Hz), 6.0(1H, d, J=5.2Hz), 7.1–7.6(10H, m), 8.04(1H, d, J=5.2Hz) |
| 188 | 59 | Oil | 1.2–2.0(4H, m), 2.5–3.0(3H, m), 4.60(2H, br. d, J=12.6Hz), 5.28(2H, s), 5.95(1H, d, J=5.2Hz), 7.0–7.70(15H, m), 7.96(1H, d, J=5.2Hz) |
| 196 | 60 | Oil | 1.2–2.0(4H, m), 2.56(6H, s), 2.5–3.10(5H, m), 4.36(2H, t, J=8Hz), 4.67(2H, br. d, J=12.6Hz), 6.0(1H, d, J=5.6Hz), 7.0–7.6(10H, m), 8.0(1H, d, J=5.6Hz) |
| 204 | 28 | Oil | 1.5–2.1(4H, m), 2.35(3H, s), 2.6–3.2(3H, m), 3.40(3H, s), 4.90(2H, br. d, J=12.6Hz), 6.60(1H, d, J=12.6Hz), 7.28(5H, m), 8.28(1H, d, J=7.2Hz) |
| 212 | 34 | 88–94 | 1.16(6H, d, J=7.2Hz), 1.4–2.1(4H, m), 2.6–3.3(4H, m), 3.36(3H, s), 4.88(2H, br. d, J=12.6Hz), 6.51(1H, d, J=5.2Hz), 7.24(5H, m), 8.24(1H, d, J=5.2Hz) |
| 220 | 45 | Oil | 1.25(9H, s), 1.5–2.0(4H, m), 2.6–3.2(3H, m), 3.29(3H, s), 4.91(2H, br. d, J=12.6Hz), 6.50(1H, d, J=5.2Hz), 7.26(5H, m), 8.26(1H, d, J=5.2Hz) |
| 228 | 35 | Oil | 1.0–2.1(14H, m), 2.6–3.2(4H, m), 3.36(3H, s), 4.90(2H, br. d, J=12.6Hz), 6.50(1H, d, J=5.2Hz), 7.25(5H, m), 8.25(1H, d, J=5.2Hz) |
| 236 | 66 | 101–104 | 1.3–2.0(4H, m), 2.5–3.0(3H, m), 3.52(3H, s), 4.60(2H, br. d, J=12.6Hz), 6.11(1H, d, J=5.2Hz), 7.1–7.5(9H, m), 8.10(1H, d, J=5.2Hz) |
| 244 | 33 | Oil | 1.2–2.0(4H, m), 2.5–3.0(3H, m), 3.51(3H, s), 4.56(2H, br. d, J=12.6Hz), 6.15(1H, d, J=5.2Hz), 7.0–7.5(9H, m), 8.10(1H, d, J=5.2Hz) |
| 260 | 41 | Oil | 1.2–1.9(4H, m), 2.4–2.9(3H, m), 3.56(3H, s), 4.49(2H, br. d, J=12.6Hz), 6.16(1H, d, J=3.6Hz), 7.0–7.5(5H, m), 7.6(2H, d, J=9.5Hz), 8.16(1H, d, J=3.6Hz), 8.20(2H, d, J=9.5Hz) |
| 268 | 27 | Oil | 1.4–2.0(4H, m), 2.5–3.0(3H, m), 3.55(3H, s), 3.79(3H, s), 4.72(2H, br. d, J=12.6Hz), 6.07(1H, d, J=5.2Hz), 6.81(2H, m), 7.1–7.6(7H, m), 8.05(1H, d, J=5.2Hz) |
| 276 | 57 | Oil | 1.4–2.0(4H, m), 2.5–3.1(3H, m), 3.53(3H, s), 3.79(6H, s), 3.84(3H, s), 4.70(2H, br. d, J=12.6Hz), 6.13(1H, d, J=5.2Hz), 6.70(2H, s), 7.22(5H, m), 8.05(1H, d, J=5.2Hz) |
| 292 | 44 | Oil | 1.5–2.0(4H, m), 2.6–3.1(3H, m), 3.55(3H, s), 4.77(2H, br. d, J=12.6Hz), 6.24(1H, d, J=5.2Hz), 6.44(1H, dd, J=3.2, 2.0Hz), 7.0(1H, dd, J=3.0, 1.0Hz), 7.1–7 5(6H, m), 8.16(1H, d, J=5.2Hz) |
| 300 | 84 | Oil | 0.5–2.0(5H, m), 2.2–2.6(4H, m), 3.59(3H, s), 3.76(2H, br. d, J=12.6Hz), 6.06(1H, d, J=5.2Hz), 7.0–7.6(10H, m), 8.0(1H, d, J=5.2Hz) |
| 308 | 35 | Oil | 2.37(3H, s), 2.95(2H, t, J=5.2Hz), 3.41(3H, s), 4.05(2H, t, J=5.2Hz), 4.92(2H, s), 6.64(1H, d, J=5.2Hz), 7.22(4H, s), 8.32(1H, d, J=5.2Hz) |
| 316 | 96 | Oil | 1.85–2.20(2H, m), 2.33(3H, s), 2.80(2H, t, J=5.2Hz), 3.40(3H, s), 4.04(2H, t, J=5.2Hz), 6.93(1H, d, J=5.2Hz), 6.95–7.30(3H, m), 7.72(1H, dd, J=7.2, 2.0Hz), 8.34(1H, d, J=5.2Hz) |
| 324 | 79 | Oil | 1.6–2.1(2H, m), 2.76(2H, t, J=5.2Hz), 3.52(3H, s), 3.80(2H, t, J=5.2Hz), 6.39(1H, d, J=5.2Hz), 6.9–7.7(9H, m), 8.15(1H, d, J=5.2Hz) |
| 332 | 42 | Oil | 3.52(3H, s), 3.59(8H, m), 6.18(1H, d, J=5.2Hz), 7.36(5H, m), 8.04(1H, d, J=5.2Hz) |
| 340 | 33 | Oil | 2.18(1H, m), 2.79(4H, m), 3.51(3H, s), 3.56(4H, m), 6.12(1H, d, J=5.2Hz), 7.35(5H, m), 8.02(1H, d, J=5.2Hz) |
| 348 | 19 | Oil | 2.31(3H, s), 2.36(4H, m), 3.52(3H, s), 3.60(4H, m), 6.12(1H, d, J=5.2Hz), 7.1–7.5(5H, m), 8.01(1H, d, J=5.2Hz) |
| 356 | 72 | Oil | 3.10(4H, m), 3.56(3H, s), 3.76(4H, m), 6.20(1H, d, J=5.4Hz), 6.90(3H, m), 7.1–7.6(7H, m), 8.09(1H, d, J=5.4Hz) |
| 364 | 52 | Oil | 2.36(4H, m), 3.4–3.8(9H, m), 6.11(1H, d, J=5.2Hz), 7.1–7.6(10H, m), 8.01(1H, d, J=5.2Hz) |
| 372 | 50 | 58–62 | 2.32(4H, m), 3.49(3H, s), 3.62(4H, m), 4.23(1H, s), 6.13(1H, d, J=5.2Hz), 7.0–7.6(14H, m), 8.02(1H, d, J=5.2Hz) |
| 380 | 63 | Oil | 1.65(6H, br. s), 2.29(3H, s), 2.35(3H, s), 3.34(3H, s), 3.77(4H, m), 6.32(1H, s) |
| 388 | 64 | Oil | 1.5–2.11(4H, m), 2.32(3H, s), 2.37(3H, s), 2.6–3.1(3H, m), 3.36(3H, s), 4.92(2H, br. d, J=12.6Hz), 6.40(1H, s), 7.28(5H, br. s) |
| 396 | 52 | Oil | 1.3–2.0(4H, m), 2.22(3H, s), 2.5–3.0(3H, m), 3.53(3H, s), 4.64(2H, br. d, J=12.6Hz), 6.05(1H, s), 7.1–7.6(10H, m) |
| 404 | 49 | Oil | 1.3–1.8(6H, m), 1.89(3H, s), 3.40(3H, s), 3.63(4H, m), 7.1–7.5(5H, m), 8.0(1H, s) |
| 412 | 28 | Oil | 1.5–2.1(4H, m), 2.0(3H, s), 2.08(3H, s), 2.6–3.2(3H, m), 3.20(3H, s), 4.85(2H, br. d, J=12.6Hz), 7.27(5H, m), 8.26(1H, s) |

TABLE 3-continued

| Compound No. | Yield (%) | Melting point (°C.) | ¹H-NMR spectrum (CDCl₃ solution, δ ppm) |
|---|---|---|---|
| 420 | 54 | Oil | 1.4–1.9(4H, m), 1.94(3H, s), 2.5–3.05(3H, m), 3.42(3H, s), 4.71(2H, br. d, J=12.6Hz), 7.0–7.6(10H, m), 8.05(1H, s) |
| 428 | 55 | Oil | 1.3–2.1(4H, m), 2.5–3.0(3H, m), 3.51(3H, d, J=0.5Hz), 4.60(1H, br. d, J=12.6Hz), 7.0–7.6(10H, m), 8.0(1H, d, J=2Hz) |
| 600 | 67 | Oil | 1.2–1.7(6H, m), 3.12(4H, m), 3.61(3H, s), 6.09(1H, d, J=7.2Hz), 7.1–7.5(5H, m), 8.0(1H, d, J=7.2Hz) |
| 608 | 57 | Oil | 0.5–1.0(2H, m), 0.87(3H, d, J=5.2Hz), 1.3–1.7(3H, m), 2.3–2.7(2H, m), 3.61(3H, s), 3.5–3.9(2H, br. d, J=12.6Hz), 6.10(1H, d, J=7.2Hz), 7.1–7.5(5H, m), 8.0(1H, d, J=7.2Hz) |
| 616 | 55 | 143–145 | 0.84(9H, s), 0.9–1.6(5H, m), 2.44(2H, m), 3.61(3H, s), 3.87(2H, br. d, J=12.6Hz). 6.10(1H, d, J=5.2Hz), 7.2–7.5(5H, m), 8.0(1H, d, J=5.2Hz) |
| 624 | 67 | Oil | 1.0–1.9(4H, m), 2.4–2.9(3H, m), 3.64(3H, s), 3.95(2H, br. d, J=12.6Hz), 6.16(1H, d, J=5.2Hz), 7.0–7.55(10H, m), 8.07(1H, d, J=5.2Hz) |
| 632 | 67 | Oil | 1.35(3H, t, J=7.2Hz), 1.0–1.9(4H, m), 2.4–2.9(3H, m), 3.97(2H, br. d, J=12.6Hz), 4.22(2H, q, J=7.2Hz), 6.15(1H, d, J=7.2Hz), 7.0–7.6(10H, m), 8.05(1H, d, J=7.2Hz) |
| 640 | 52 | Oil | 0.99(3H, t, J=7.2Hz), 1.0–2.0(6H, m), 2.4–2.9(3H, m), 3.99(2H, br. d, J=12.9Hz), 4.0–4.3(2H, m), 6.15(1H, d, J=7.2Hz), 7.0–7.6(10H, m), 8.04(1H, d, J=7.2Hz) |
| 648 | 63 | Oil | 1.0–2.0(4H, m), 1.46(3H, s), 1.54(3H, s), 2.5–3.0(3H, m), 4.15(2H, br. d, J=12.6Hz), 5.13(1H, m), 6.19(1H, d, J=7.2Hz), 7.0–7.6(10H, m), 8.04(1H, d, J=7.2Hz) |
| 658 | 88 | Oil | 1.0–1.85(4H, m), 2.4–2.80(3H, m), 3.95(2H, br. d, J=12.6Hz), 5.38(2H, s), 6.10(1H, d, J=5.2Hz), 7.0–7.60(15H, m), 7.98(1H, d, J=5.2Hz) |
| 664 | 71 | 160–162 | 1.0–2.0(4H, m), 2.4–2.9(3H, m), 3.62(3H, s), 3.99(2H, br. d, J=12.6Hz), 6.16(1H, d, J=5.2Hz), 7.0–7.5(9H, m), 8.05(1H, d, J=5.2Hz) |
| 672 | 60 | 153–154 | 1.0–2.0(4H, m), 2.5 2.9(3H, m), 3.65(3H, s), 4.0(2H, br. d, J=12.6Hz), 6.20(1H, d, J=7.2Hz), 7.0–7.5(5H, m), 7.56(2H, d, J=10.8Hz), 8.01(1H, d, J=7.2Hz), 8.14(2H, d, J=10.8Hz) |
| 680 | 59 | Oil | 1.4–2.0(4H, m), 2.5–3.0(3H, m), 3.56(3H, s), 4.22(2H, br. d, J=12.6Hz), 6.25(1H, d, J=5.2Hz), 6.36(1H, dd, J=4.0, 1.0Hz), 6.88(1H, d, J=4.0Hz), 7.0–7.5(6H, m), 8.08(1H, d, J=5.2Hz) |
| 688 | 41 | Oil | 0.8–1.8(5H, m), 2.3–2.8(4H, m), 3.51(3H, s), 4.45(2H, br. d, J=12.6Hz), 6.07(1H, d, J=5.2Hz), 7.0–7.6(10H, m), 8.02(1H, d, J=5.2Hz) |
| 696 | 69 | 99–101 | 2.0(2H, m), 2.48(3H, s), 2.79(2H, t, J=5.2Hz), 3.48(3H, s), 3.97(2H, t, J=5.2Hz), 6.80(1H, d, J=5.2Hz), 7.0–7.5(4H, m), 8.13(1H, d, J=5.2Hz) |
| 252 | 38 | Oil | 1.3–2.0(4H, m), 2.4–3.0(3H, m), 3.47(3H, s), 4.59(2H, br. d, J=12.6Hz), 6.47(1H, d, J=5.2Hz), 7.0–7.6(9H, m), 8.13(1H, d, J=5.2Hz) |
| 284 | 38 | 136–138 | 1.2–2.0(4H, m), 2.4–3.0(3H, m), 3.53(3H, s), 4.59(2H, br. d, J=12.6Hz), 6.15(1H, d, J=5.2Hz), 6.95–7.60(14H, m), 8.05(2H, d, J=5.2Hz) |
| 137 | 95 | Oil | 0.88(3H, d, J=7Hz), 1.1–2.8(7H, m), 3.50(3H, s), 4.28(2H, m), 6.03(1H, d, J=5Hz), 7.34(5H, m), 7.99(1H, d, J=5Hz) |
| 145 | 38 | Oil | 0.7–2.8(12H, m), 3.49(3H, s), 4.40(2H, m), 6.02(1H, d, J=5Hz), 7.32(5H, m), 7.96(1H, d, J=5Hz) |
| 147 | 96 | Oil | 0.88(6H, d, J=7Hz), 1.0–2.9(8H, m), 3.50(3H, s), 4.47(2H, m), 6.04(1H, d, J=5Hz), 7.34(5H, m), 8.00(1H, d, J=5Hz) |
| 153 | 38 | Oil | 1.04(3H, d, J=7Hz), 1.54(6H, m), 2.76(1H, m), 3.49(3H, s), 4.28(1H, m), 4.70(1H, m), 6.02(1H, d, J=5Hz), 7.32(5H, m), 7.98(1H, d, J=5Hz) |
| 171-2 | 56 | 126–129 | 1.2–2.0(4H, m), 2.32(3H, s), 2.5–3.0(3H, m), 3.52(3H, s), 4.65(2H, br. d, J=12.6Hz), 6.08(1H, d, J=5.2Hz), 6.98–7.42(9H, m), 8.01(1H, d, J=5.2Hz) |
| 2000 | 95 | Oil | 0.87(6H, d, J=7Hz), 1.1–3.4(6H, m), 3.50(3H, s), 4.36(2H, m), 6.06(1H, d, J=5Hz), 7.36(5H, m), 8.02(1H, d, J=5Hz) |
| 2008 | 50 | Oil | 1.4–2.0(4H, m), 2.38(3H, s), 2.5–3.1(3H, m), 3.44(3H, s), 4.75(2H, br. d, J=12.6Hz), 6.80(1H, d, J=5.2Hz), 7.0–7.4(7H, m), 7.66(2H, d, J=7.2Hz), 8.09(1H, d, J=5.2Hz) |
| 2048 | 37 | Oil | 8.00(1H, d, J=5Hz), 7.2–7.5(5H, m), 6.12(1H, d, J=5Hz), 4.4–4.7(2H, m), 3.50(3H, s), 1.1–3.0(17H, m) |
| 2056 | 89 | Oil | 8.00(1H, d, J=5Hz), 7.2–7.5(5H, m), 6.08(1H, d, J=5Hz), 3.7–4.3(4H, m), 3.50(3H, s), 2.9–3.3(2H, m), 1.0–2.0(4H, m) |
| 2064 | 47 | Oil | 8.00(1H, d, J=5Hz), 7.2–7.6(5H, m), 6.18(1H, d, J=5Hz), 4.2–4.5(2H, m), 3.60(3H, s), 1.0–4.0(12H, m) |
| 2074 | 35 | Oil | 8.12(2H, d, J=7Hz), |

TABLE 3-continued

| Compound No. | Yield (%) | Melting point (°C.) | $^1$H-NMR spectrum (CDCl$_3$ solution, δ ppm) |
|---|---|---|---|
| | | | 7.88(1H, d, J=5Hz), 7.35(1H, d, J=7Hz), 6.22(1H, d, J=5Hz), 7.2-7.6(5H, m), 4.8-5.0(2H, m), 3.64(3H, s), 2.7-3.1(2H, m), 1.1-2.0(5H, m) |
| 2080 | 16 | Oil | 8.02(1H, d, J=7Hz), 7.2-7.6(5H, m), 6.29(1H, d, J=7Hz), 4.0-4.6(2H, m), 2.49(3H, s), 0.8-3.2(14H, m) |
| 2088 | 38 | Oil | 8.03(1H, d, J=7Hz), 7.2-7.5(5H, m), 6.28(1H, d, J=7Hz), 3.47(3H, s), 3.08(3H, s), 1.6-3.8(10H, m) |
| 2096 | 36 | Oil | 8.03(1H, d, J=5Hz), 7.2-7.6(5H, m), 6.58(1H, d, J=5Hz), 4.5-4.8(2H, m), 4.18(2H, q, J=7Hz), 1.50(3H, s), 1.5-3.0(7H, m), 1.30(3H, t, J=2Hz) |
| 2112 | 95 | Oil | 0.96(6H, s), 1.26(4H, m), 3.48(3H, s), 3.50(4H, m), 6.02(1H, d, J=5Hz), 7.32(5H, m), 7.98(1H, d, J=5Hz) |
| 2120 | 44 | Oil | 0.85(3H, t, J=7Hz), 1.47(4H, m), 2.79(2H, m), 3.1-3.7(6H, m), 6.08(1H, d, J=5Hz), 7.30(10H, m), 8.04(1H, d, J=5Hz) |
| 2128 | 28 | Oil | 1.4-2.1(4H, m), 2.5-3.1(3H, m), 3.54(3H, s), 4.73(2H, br. d, J=12.6Hz), 6.24(1H, d, J=5.4Hz), 6.92(1H, dd, J=5.4, 3.6Hz), 7.0-7.5(7H, m), 8.08(1H, d, J=5.4Hz) |
| 2136 | 93 | Oil | 1.3-2.0(4H, m), 2.45-3.0(3H, m), 3.52(3H, s), 4.48(2H, br. d, J=12.6Hz), 6.13(1H, d, J=5.4Hz), 7.0-7.4(6H, m), 7.75(1H, m), 8.10(1H, d, J=5.4Hz), 8.54(2H, m) |
| 2144 | 53 | Oil | 8.00(1H, d, J=7Hz), 7.2-7.5(5H, m), 6.13(1H, d, J=7Hz), 4.3-4.5(2H, m), 2.0-3.8(7H, m), 3.10(6H, s), 3.36(3H, s) |
| 2152 | 40 | Oil | 8.00(1H, d, J=7Hz), 7.2-7.5(5H, m), 6.38(1H, d, J=7Hz), 3.38(3H, s), 4.0-4.8(2H, m), 0.8-2.04(14H, m) |
| 2160 | 45 | Oil | 8.00(1H, d, J=5Hz), 7.2-7.6(5H, m), 6.10(1H, d, J=5Hz), 4.1-4.4(2H, m), 3.58(3H, s), 1.0-3.5(10H, m) |
| 2170 | 42 | Oil | 1.2-3.1(7H, m), 3.51(3H, s), 3.89(1H, m), 4.40(2H, m), 6.19(1H, d, J=5Hz), 7.2-7.9(10H, m), 8.01(1H, d, J=5Hz) |
| 2178 | 85 | Oil | 1.5-3.1(6H, m), 3.51(3H, s), 3.90(1H, m), 4.74(2H, m), 6.02(1H, d, J=5Hz), 6.50(2H, d, J=8Hz), 7.24(7H, m), 7.96(1H, d, J=8Hz) |
| 2184 | 56 | Oil | (CDCl$_3$—CD$_3$OD) 1.2-3.3(7H, m), 3.50(3H, s), 4.46(2H, m), 6.20(1H, d, J=5Hz), 7.36(5H, m), 8.01(1H, d, J=5Hz) |
| 2192 | 50 | Oil | 1.4-3.3(6H, m), 3.56(3H, s), 4.2-4.7(3H, m), 6.60(1H, d, J=7Hz), 7.1-7.9(14H, m), 7.96(1H, d, J=7Hz) |
| 2198 | 42 | Oil | (CDCl$_3$—CD$_3$OD) 1.4-3.3(7H, m), 3.53(3H, s), 4.42(2H, m), 6.72(1H, d, J=7Hz), 7.3-7.9(10H, m), 7.98(1H, d, J=7Hz) |
| 2206 | 45 | Oil | 1.61(6H, br. s), 1.4-2.1(4H, m), 2.55-3.15(3H, m), 3.22(3H, s), 3.40(4H, br. s), 4.87(2H, br. d, J=12.6Hz), 5.97(1H, d, J=5.2Hz), 7.24(5H, m), 8.0(1H, d, J=5.2Hz) |
| 2214 | 26 | 131-132 | 1.5-2.2(4H, m), 2.5-3.3(3H, m), 3.40(3H, s), 4.80(2H, br. d, J=12.6Hz), 6.16(1H, d, J=5.2Hz), 6.89-7.65(10H, m), 8.20(1H, d, J=5.2Hz), 12.23(1H, br, s) |
| 2222 | 60 | 46-49 | 7.9-8.1(3H, m), 7.2-7.6(8H, m), 6.10(1H, d, J=5Hz), 5.0-5.2(1H, m), 3.8-4.1(2H, m), 3.50(3H, s), 1.8-2.0(6H, m) |
| 2230 | 97 | Oil | 1.26-2.10(4H, m), 2.30(3H, s), 2.39(4H, m), 2.5-3.20(3H, m), 3.21(3H, s), 3.47(4H, m), 4.85(2H, br. d, J=12.6Hz), 5.96(1H, d, J=5.2Hz), 7.20(5H, m), 8.0(1H, d, J=5.2Hz) |
| 2238 | 69 | Oil | 1.35(3H, t, J=7.2Hz), 1.4-2.15(4H, m), 2.55-3.20(3H, m), 3.44(3H, s), 4.25(2H, q, J=7.2Hz), 4.86(2H, br. d, J=12.6Hz), 7.23(6H, m), 8.12(1H, d, J=5.2Hz) |
| 2246 | 13 | Oil | 1.2-3.4(7H, m), 3.56(3H, s), 3.92(2H, s), 4.74(2H, m), 6.50(1H, d, J=7Hz), 7.18(10H, m), 8.18(1H, d, J=7Hz) |
| 2254 | 45 | Oil | 0.94(3H, t, J=7Hz), 1.52(6H, m), 2.02(2H, m), 2.79(4H, m), 3.50(3H, s), 4.50(2H, m), 5.04(2H, m), 6.09(1H, d, J=7Hz), 7.36(5H, m), 7.98(1H, d, J=7Hz) |
| 2264 | 90 | Oil | 1.1-1.6(4H, m), 2.4-2.9(3H, m), 3.46(3H, s), 4.50(2H, m), 6.06(1H, d, J=5Hz), 7.28(15H, m), 7.94(1H, d, J=5Hz) |
| 2274 | 62 | 112-115 | 1.35-2.10(4H, m), 2.50-3.10(3H, m), 3.0(3H, s), 4.74(2H, s), 4.88(2H, br. d, J=12.6Hz), 5.79(1H, d, J=5.2Hz), 7.22(10H, m), 7.90(1H, d, J=5.2Hz) |
| 2282 | 67 | Oil | 1.45-2.15(4H, m), 2.55-3.20(3H, m), 3.40(3H, s), 4.82(2H, br. d, J=12.6Hz), 5.05(2H, s), 6.37(1H, d, J=5.2Hz), 6.70-7.10(3H, m), 7.10-7.45(7H, m), 8.25(1H, d, J=5.2Hz) |
| 2290 | 42 | Oil | 1.4-2.1(4H, m), 2.96(6H, s), 2.58-3.20(3H, m), 3.20(3H, s), 4.85(2H, br. d, J=12.6Hz), 5.92(1H, d, J=5.2Hz), 7.22(5H, m), 8.02(1H, d, J=5.2Hz) |
| 2298 | 56 | Oil | 1.15(6H, m), 1.4-2.1(4H, m), 2.5-3.2(3H, m), 3.18(3H, s), 3.35(4H, m), 4.88(2H, br. d, J=12.6Hz), 5.90(1H, d, J=5.2Hz), 7.22(5H, m), 7.98(1H, d, J=5.2Hz) |
| 2306 | 75 | Oil | 1.76(4H, m), 2.92(2H, m), 3.36(1H, m), 3.51(3H, s), 4.52(2H, m), 6.52(1H, d, J=7Hz), |

TABLE 3-continued

| Compound No. | Yield (%) | Melting point (°C.) | ¹H-NMR spectrum (CDCl₃ solution, δ ppm) |
|---|---|---|---|
| 2314 | 26 | Oil | 7.39(7H, m), 7.86(2H, d, J=7Hz), 8.02(1H, d, J=7Hz), 1.2–2.0(4H, m), 2.1–2.9(3H, m), 3.90(3H, s), 4.32(2H, m), 6.70(1H, d, J=7Hz), 7.0–7.7(10H, m), 8.23(1H, d, J=7Hz) |
| 2322 | 77 | Oil | 1.4–2.1(4H, m), 2.5–3.4(3H, m), 3.24(3H, s), 3.57(8H, m), 4.88(2H, br. d, J=12.6Hz), 6.0(1H, d, J=5.4Hz), 7.23(5H, m), 8.04(1H, d, J=5.4Hz) |
| 2330 | 59 | 119–121 | 1.4–2.1(4H, m), 2.6–3.2(3H, m), 3.61(3H, s), 4.89(2H, br. d, J=12.6Hz), 7.0–7.5(11H), 8.16(1H, d, J=5.4Hz) |
| 2338 | 23 | Oil | 8.02(1H, d, J=7Hz), 7.2–7.6(5H, m), 6.38(1H, d, J=7Hz), 3.36(3H, s), 1.0–3.5(13H, m) |
| 2346 | 54 | Oil | 8.00(1H, d, J=7Hz), 7.2–7.9(10H, m), 6.48(1H, d, J=7Hz), 4.2–4.5(2H, m), 3.38(3H, s), 1.4–3.8(7H, m) |
| 2016 | 50 | Oil | 1.4–2.0(4H, m), 2.5–3.0(3H, m), 3.53(3H, s), 4.21(2H, br. d, J=12.6Hz), 6.12(1H, d, J=7.2Hz), 6.35(1H, d, J=7.2Hz), 7.0–7.5(11H, m) |
| 2024 | 36 | Oil | 1.4–2.0(4H, m), 2.5–3.1(3H, m), 3.54(3H, s), 4.25(2H, br. d, J=12.6Hz), 7.0–7.6(10H, m), 7.41(1H, s), 7.79(1H, s) |
| 2032 | 69 | 76–82 | 1.2–2.0(8H, m), 2.4–3.9(6H, m), 3.56(3H, s), 4.50(4H, m), 7.0–7.52(15H, m) |
| 2040 | 28 | Oil | 1.4–2.1(4H, m), 2.5–3.2(3H, m), 3.50(3H, s), 4.38(2H, br. d, J=12.6Hz), 6.32(1H, dd, J=3.6, 2.0Hz), 6.71(1H, dd, J=3.0, 1.0Hz), 7.24(6H, m), 7.58(1H, s), 7.93(1H, s) |
| 154-1 | 61 | Oil | 1.4–2.2(4H, m), 2.6–3.2(3H, m), 3.36(3H, s), 3.43(3H, s), 4.43(2H, s), 4.84(2H, br. d, J=12.6Hz), 6.44(1H, d, J=5.2Hz), 7.22(5H, m), 8.22(1H, d, J=5.2Hz) |
| 171-4 | 64 | Oil | 1.37(3H, t, J=7.2Hz), 1.4–2.1(4H, m), 2.5–3.05(3H, m), 3.52(3H, s), 3.98(2H, q, J=7.2Hz), 4.69(2H, br. d, J=12.6Hz), 6.03(1H, d, J=5.2Hz), 6.76(2H, m), 7.0–7.6(7H, m), 8.0(1H, d, J=5.2Hz) |
| 297 | 60 | Oil | 1.80(4H, m), 2.90(3H, m), 4.92(2H, m), 6.64(1H, d, J=5Hz), 7.20(5H, m), 7.80(4H, m), 8.39(1H, d, J=5Hz) |
| 305 | 90 | Oil | 1.76(4H, m), 2.90(2H, m), 3.40(1H, m), 3.51(3H, s), 4.49(2H, m), 6.11(1H, d, J=5Hz), 7.40(8H, m), 7.92(2H, m), 8.01(1H, d, J=5Hz) |
| 307 | 19 | Oil | 8.01(1H, d, J=7Hz), 7.2–7.6(5H, m), 6.10(1H, d, J=7Hz), 4.2–4.4(2H, m), 1.2–3.8(10H, m), 3.35(3H, s) |
| 241 | 69 | Oil | 1.1–2.1(4H, m), 2.5–3.0(3H, m), 3.50(3H, s), 4.60(2H, br. d, J=12.6Hz), |
| 2022 | 84 | Oil | 6.04(1H, d, J=5.2Hz), 6.8–7.7(9H, m), 8.04(1H, d, J=5.2Hz) 1.4–2.0(4H, m), 2.45–3.0(3H, m), 3.52(3H, s), 4.20(2H, br. d, J=12.6Hz), 6.10(1H, d, J=7.2Hz), 6.35(1H, d, J=7.2Hz), 7.0–7.4(10H, m) |
| 2023 | 85 | 112–114 | 1.3–2.1(4H, m), 2.5–3.2(3H, m), 3.47(3H, s), 4.35(2H, br. d, J=12.6Hz), 6.31(1H, d, J=7.2Hz), 6.50(1H, d, J=7.2Hz), 6.65–7.6(9H, m, J=7.2Hz) |
| 149 | 87 | 103–105 | 0.5–1.8(5H, m), 0.88(3H, d, J=5.2Hz), 2.3–2.8(2H, m), 4.15(2H, br. d, J=12.6Hz), 6.06(1H, d, J=5.2Hz), 7.1–7.8(10H, m), 8.08(1H, d, J=5.2Hz) |
| 171-8 | 79 | Oil | 1.2–2.0(4H, m), 2.4–3.0(3H, m), 3.52(3H, s), 4.51(2H, br. d, J=12.6Hz), 6.32(1H, d, J=5.2Hz), 6.76–7.65(9H, m), 8.1(1H, d, J=5.2Hz) |
| 171-10 | 62 | Oil | 1.2–2.1(4H, m), 2.5–3.0(3H, m), 3.49(3H, s), 4.53(2H, br. d, J=12.6Hz), 6.36(1H, d, J=5.2Hz), 7.0–7.5(8H, m), 8.12(1H, d, J=5.2Hz) |
| 171-1 | 26 | Oil | 1.3–2.1(4H, m), 2.5–3.0(3H, m), 3.47(3H, s), 4.85(2H, d, J=12.6Hz), 6.35(1H, d, J=5.2Hz), 6.90(1H, d, J=15.4Hz), 7.0–7.6(10H, m), 7.65(1H, d, J=15.4Hz), 8.20(1H, d, J=5.2Hz) |
| 171-6 | 41 | Oil | 1.4–2.0(4H, m), 2.34(3H, s), 2.5–3.0(3H, m), 3.46(3H, s), 4.64(2H, br. d, J=12.6Hz), 6.32(1H, d, J=5.2Hz), 7.0–7.4(9H, m), 8.04(1H, d, J=5.2Hz) |
| 171-12 | 71 | 113–116 | 1.1–2.1(4H, m), 2.4–3.0(3H, m), 3.49(3H, s), 4.51(2H, br. d, J=12.6Hz), 6.1(1H, d, J=5.2Hz), 7.0–7.7(8H, m), 8.1(1H, d, J=5.2Hz) |

EXAMPLE 2

4-(N-Methylbenzamino)-2-(4Phenylpiperidino)Pyrimidine P-Toluenesulfonate (Compound No. 168)

A solution of 3.0 g (0.022 mole) of p-toluenesulfonic acid monohydrate in 300 ml of ethyl acetate was slowly added at room temperature to a solution of 6.0 g (0.022 mole) of 4-(N-methylbenzamino)-2-(4-phenylpiperidino)pyrimidine in 100 ml of ethyl acetate. As soon as the addition was effected, a suspension was formed. After the end of the addition, the suspension was stirred for 10 minutes. The resulting solid was separated by filtration, washed with ethyl acetate and ether, and dried to give 6.8 g (yield 83%) of the desired compound.

Melting point: 180°–182° C.

¹H-NMR spectrum (deuterochloroform, δ ppm): 1.4–2.1(4H, m), 2.35(3H, s), 2.6–3.3(3H, m), 3.56(3H, s), 4.55(2H, br. d, J=12.6 Hz), 6.60(1H, d, J=7.2 Hz), 7.0–7.9(14H, m), 8.36(1H, d, J=7.2 Hz).

In the same way as above, the following compounds were produced and thier data are shown in Table 4.

TABLE 4

| Compound No. | Yield (%) | Melting point (°C.) | ¹H-NMR spectrum (CDCl₃ solution, δppm) |
|---|---|---|---|
| 104 | 100 | 54–58 | 2.33(3H, s), 2.8–3.5(6H, m), 3.50(3H, s), 6.64(1H, d, J=7.2Hz) 7.13(2H, d, J=7.2Hz), 7.50(5H, m,), 7.75(2H, d, J=7.2Hz) 8.24(1H, d, J=7.2Hz) |
| 112 | 100 | Oil | 0.90(6H, m), 1.0–1.8(8H, m), 2.35(3H, s), 3.2–3.7(4H, m), 3.5(3H, s), 6.58(1H, d, J=7.2Hz), 7.13(2H, d, J=7.2Hz), 7.3–7.7(5H, m), 7.76(2H, d, J=7.2Hz) 8.36(1H, d, J=7.2Hz) |
| 120 | 82 | 125–126 | 2.0(4H, m), 2.35(3H, s), 3.44(2H, m), 3.52(3H, s), 3.72(2H, m), 6.56(1H, d, J=7.2Hz), 7.15(2H, d, J=7.2Hz), 7.2–7.7(5H, m), 7.78(2H, d, J=7.2Hz), 8.22(1H, d, J=7.2Hz) |
| 128 | 90 | 149–150 | 1.72(6H, br. s), 2.37(3H, s), 2.48(3H, s), 3.50(3H, s), 3.84(4H, br. s), 7.18(2H, d, J=7.5Hz), 7.44(1H, d, J=7.2Hz), 7.81(2H, d, J=7.5Hz), 8.38(1H, d, J=7.2Hz) |
| 136 | 79 | 48–52 | 1.63(6H, br. s), 2.36(3H, s), 3.52(3H, s), 3.64(4H, br, s), 6.56(1H, d, J=7.2Hz), 7.16(2H, d, J=7.2Hz), 7.55(5H, m), 7.79(2H, d, J=7.2Hz), 8.30(1H, d, J=7.2Hz) |
| 144 | 90 | 49–51 | 0.94(3H, d, J=5.2Hz), 0.8–1.90(5H, m), 2.36(3H, s), 2.8–3.2(2H, m), 3.52(3H, s), 4.32(2H, br. d, J=12.6Hz), 6.6(1H, d, J=7.2Hz), 7.16(2H, d, J=7.2Hz), 7.3–7.7(5H, m), 7.8(2H, d, J=7.2Hz), 8.3(1H, d, J=7.2Hz) |
| 152 | 72 | 52–56 | 0.85(9H, s), 1.0–2.0(5H, m), 2.36(3H, s), 2.5–3.2(2H, m), 3.52(3H, s), 4.44(2H, br. d, J=12.6Hz), 6.58(1H, d, J=7.2Hz), 7.16(2H, d, J=7.2Hz), 7.3–7.7(5H, m), 7.8(2H, d, J=7.2Hz) 8.28(1H, d, J=7.2Hz) |
| 160 | 80 | 206–207 | 1.3–2.1(4H, m), 2.32(3H, s), 2.5–3.3(3H, m), 4.76(2H, br. d, J=12.6Hz), 7.0–8.4(16H, m) |
| 176 | 75 | 68–72 | 1.36(3H, t, J=7.2Hz), 1.4–2.1(4H, m), 2.33(3H, s), 2.5–3.3(3H, m), 4.12(2H, q, J=7.2Hz), 4.42(2H, br. d, J=12.6Hz), 6.34(1H, d, J=7.2Hz), 7.0–7.9(12H, m), 8.32(1H, d, J=7.2Hz) |
| 184 | 85 | 53–57 | 1.0(3H, t, J=7.2Hz), 1.4–2.1(6H, m) 2.35(3H, s), 2.5–3.3(3H, m), 4.04(2H, m), 4.42(2H, br. d, J=12.6Hz), 6.28(1H, d, J=7.2Hz), 7.0–7.7(14H, m), 8.35(1H, d, J=7.2Hz) |
| 192 | 80 | 59–62 | 1.2–2.0(4H, m), 2.31(3H, s), 2.5–3.2(3H, m), 4.34(2H, m), 5.28(2H, s), 6.33(1H, d, J=7.2Hz), 7.0–7.8(19H, m), 8.25(1H, d, J=7.2Hz) |
| 200 | 79 | 98–105 | 1.4–2.0(4H, m), 2.32(6H, s), 2.5–3.2(3H, m), 2.92(3H, s), 2.98(3H, s), 2.98(3H, s), 3.50(2H, m), 4.40(2H, br. d, J=12.6Hz), 4.60(2H, m), 6.40(1H, d, J=5.2Hz), 7.0–7.8(18H, m), 8.10(1H, d, J=5.2Hz), 10.80(1H, m) |
| 208 | 90 | 172–174 | 1.6–2.2(4H, m), 2.35(3H, s), 2.48(3H, s), 2.6–3.5(3H, m), 3.52(3H, s), 4.77(2H, br. d, J=12.6Hz), 7.1–7 9(10H, m), 8.42(1H, d, J=7.2Hz) |
| 216 | 86 | 154–156 | 1.24(6H, d, J=7.0Hz), 1.4–2.2(4H, m), 2.32(3H, s), 2.6–3.4(4H, m), 3.51(3H, s), 4.75(2H, br. d, J=12.6Hz), 7.12(2H, d, J=7.2Hz), 7.20(5H, m), 7.36(1H, d, J=7.2Hz), 7.76(2H, d, J=7.2Hz), 8.34(1H, d, J=7.2Hz) |
| 224 | 86 | 158–160 | 1.40(9H, s), 1.5–2.2(4H, m), 2.34(3H, s), 2.6–3.3(3H, m), 3.38(3H, s), 4.76(2H, br. d, J=12.6Hz), 6.56(1H, d, J=7.2Hz), 7.0–7.4(7H, m), 7.82(2H, d, J=7.2Hz) 8.30(1H, d, J=7.2Hz) |
| 232 | 100 | 49–52 | 1.0–2.3(14H, m), 2.33(3H, s), 2.6–3.5(4H, m), 3.48(3H, s), 4.75(2H, br. d, J=12.6Hz), 7.12(2H, d, J=7.2Hz), 7.0–7.5(6H, m), 7.76(2H, d, J=7.2Hz), 8.32(1H, d, J=7.2Hz) |
| 240 | 77 | 132–134 | 1.4–2.1(4H, m), 2.36(3H, s), 2.6–3.3(3H, m), 3.55(3H, s), 4.52(2H, br. d, J=12.6Hz), 6.67(1H, d, J=7.2Hz), 7.16(2H, d, J=7.2Hz), 7.0–7.7(9H, m), 7.81(2H, d, J=7.2Hz), 8.44(1H, d, J=7.2Hz) |
| 248 | 84 | 168–170 | 1.2–2.1(4H, m), 2.32(3H, s), 2.5–3.4(3H, m), 3.51(3H, s), 4.48(2H, br. d, J=12.6Hz), 6.69(1H, d, J=7.2Hz), 7.12(2H, d, J=7.2Hz), 7.0–7.65(9H, m), 7.76(2H, d, J=7.2Hz), 8.40(1H, d, J=7.2Hz) |
| 264 | 95 | 189–190 | 1.2–2.0(4H, m), 2.34(3H, s), 2.5–3.3(3H, m), 3.55(3H, s), 4.40(2H, br. d, J=12.6Hz), 6.85(1H, d, J=7.2Hz), 7.0–7.5(7H, m), 7.77(4H, d, J=7.2Hz), 8.31(2H, d, J=7.2Hz), 8.52(1H, d, J=7.2Hz) |
| 272 | 84 | 56–60 | 1.4–2.0(4H, m), 2.33(3H, s), 2.6–3.25(3H, m), 3.54(3H, s), 3.84(3H, s), 6.38(1H, d, J=7.2Hz), 6.92(2H, d, J=8.5Hz), 7.23(7H, m), 7.59(2H, d, J=8.5Hz), 7.80(2H, d, J=7.2Hz), 8.22(1H, d, J=7.2Hz) |
| 280 | 91 | 174–76 | 1.4–2.2(4H, m), 2.32(3H, s), 2.5–3.4(3H, m), 3.51(3H, s), 3.86(6H, s), 3.91(3H, s), 4.65(2H, br. d, J=12.6Hz), 6.69(1H, d, J=7.2Hz), 6.85(2H, s), 7.0–7.4(7H, m), 7.76(2H, d, J=7.2Hz), 8.30(1H, d, J=7.2Hz) |
| 296 | 91 | 174–78 | 1.4–2.2(4H, m), 2.35(3H, s), 2.6–3.3(3H, m), 3.58(3H, s), 4.69(2H, br. d, J=12.6Hz), 6.55(1H, d, J=7.2Hz), 6.60(1H, m), |

TABLE 4-continued

| Compound No. | Yield (%) | Melting point (°C.) | $^1$H-NMR spectrum (CDCl$_3$ solution, δppm) |
|---|---|---|---|
| 304 | 100 | 54-58 | 7.0-7.5(8H, m), 7.56(1H, m), 7.8(2H, d, J=7.2Hz), 8.36(1H, d, J=7.2Hz) 0.8-2.0(5H, m), 2.33(3H, s), 2.51(2H, d, J=7.2Hz), 2.6-3.2(2H, m), 3.49(3H, s), 4.35(2H, br. d, J=12.6Hz), 6.57(1H, d, J=7.2Hz), 7.0-7.9(14H, m), 8.28(1H, d, J=7.2Hz), |
| 312 | 78 | 182-184 | 2.37(3H, s), 2.51(3H, s), 3.01(2H, t, J=5.2Hz), 3.57(3H, s), 4.04(2H, t, J=5.2Hz), 4.95(2H, s), 7.20(2H, d, J=7.2Hz), 7.25(4H, s), 7.54(1H, d, J=7.2Hz), 7.94(2H, d, J=7.2Hz), 8.40(1H, d, J=7.2Hz) |
| 320 | 81 | 49-51 | 1.9-2.3(2H, m), 2.36(3H, s), 2.40(3H, s), 2.72(2H, t, J=5.2Hz), 3.38(3H, s), 4.04(2H, t, J=5.2Hz), 7.20(5H, m), 7.50(1H, m), 7.76(3H, m), 8.53(1H, d, J=5.2Hz) |
| 328 | 75 | 136-138 | 2.04(2H, q, J=5.2Hz), 2.38(3H, s), 2.73(2H, t, J=5.2Hz), 3.43(3H, s), 3.99(2H, t, J=5.2Hz), 6.88(1H, d, J=7.2Hz), 7.20(5H, m), 7.50(6H, m), 7.80(2H, d, J=7.2Hz), 8.50(1H, d, J=7.2Hz) |
| 336 | 100 | 58-62 | 2.36(3H, s), 3.52(3H, s), 3.68(8H, br. s), 6.69(1H, d, J=7.0Hz) 7.15(2H, d, J=7.2Hz), 7.52(5H, m), 7.75(2H, d, J=7.2Hz), 8.28(1H, d, J=7.0Hz) |
| 344 | 100 | 164-168 | 2.39(3H, s), 3.10(4H, m), 3.48(3H, s), 3.83(4H, m), 6.28(1H, d, J=5.2Hz), 7.20(2H, d, J=7.2Hz), 7.35(5H, m), 7.73(2H, d, J=7.2Hz), 8.05(1H, d, J=5.2Hz), |
| 352 | 100 | 58-60 | 2.36(3H, s), 2.83(3H, s), 2.98(4H, m), 3.49(3H, s), 3.90(4H, m), 6.33(1H, d, J=5.2Hz), 7.15(2H, d, J=7.2Hz), 7.0-7.5(5H, m), 7.75(2H, d, J=7.2Hz), 8.06(1H, d, J=5.2Hz) |
| 360 | 100 | 52-56 | 2.34(3H, s), 3.32(4H, br. s), 3.49(3H, s), 4.0(4H, br. s), 6.68(1H, d, J=7.2Hz), 7.0-7.8(14H, m), 8.22(1H, d, J=7.2Hz) |
| 368 | 82 | 66-72 | 2.38(3H, s), 3.05(4H, m), 3.46(3H, s), 4.0(4H, m), 4.25(2H, s), 6.32(1H, d, J=5.2Hz), 7.17(2H, d, J=7.2Hz), 7.40(10H, m), 7.79(2H, d, J=7.2Hz), 8.05(1H, d, J=5.2Hz) |
| 376 | 91 | 120-125 | 2.36(3H, s), 2.94(4H, m), 3.44(3H, s), 4.0(4H, m), 5.0(1H, m) 6.40(1H, d, J=5.2Hz), 7.0-7.9(18H, m), 8.05(1H, d, J=5.2Hz) |
| 384 | 80 | 157-158 | 1.67(6H, br. s), 2.31(3H, s), 2.46(3H, s), 2.71(3H, s), 3.48(3H, s), 3.76(4H, m), 6.33(1H, s), 7.14(2H, d, J=7.2Hz), 7.80(2H, d, J=7.2Hz) |
| 392 | 85 | 159-161 | 1.6-2.2(4H, m), 2.34(3H, s), 2.48(3H, s), 2.71(3H, s), 2.7-3.4(3H, m), 3.50(3H, s), 4.87(2H, br. d, J=12.6Hz), 7 14(2H, d, J=7.2Hz), 7.30(6H, m), 7.80(2H, d, J=7.2Hz) |
| 400 | 94 | 60-65 | 1.4-2.1(4H, m), 2.32(3H, s), 2.64(3H, s), 2.6-3.3(3H, m), 3.52(3H, s), 4.64(2H, br. d, J=12.6Hz), 6.51(1H, s), 7.15(2H, d, J=7.2Hz), |
| 408 | 83 | 50-55 | 7.0-7.7(10H, m), 7.80(2H, d, J=7.2Hz) 1.64(6H, br. s), 2.04(3H, d, J=1.0Hz), 2.39(3H, s), 3.48(3H, s), 3.70(4H, br. s), 7.20(2H, d, J=7.2Hz), 7.52(5H, m), 7.80(2H, d, J=7.2Hz), 8.33(1H, s) |
| 416 | 80 | 58-62 | 1.6-2.2(4H, m), 2.09(3H, m), 2.29(3H, s), 2.35(3H, s), 2.6-3.5(3H, m), 3.36(3H, s), 4.79(2H, br. d, J=12.6Hz), 7.18(2H, d, J=7.2Hz), 7.30(5H, m), 7.84(2H, d, J=7.2Hz), 8.46(1H, s), |
| 424 | 94 | 68-72 | 1.4-2.2(4H, m), 2.06(3H, m), 2.35(3H, s), 2.6-3.4(3H, m), 3.49(3H, s), 4.62(2H, br. d, J=12.6Hz), 7.0-7.7(12H, m), 7.81(2H, d, J=8.5Hz), 8.37(1H, s) |
| 432 | 80 | 146-148 | 1.3-2.2(4H, m), 2.36(3H, s), 2.5-3.4(3H, m), 3.58(3H, d, J=1.0Hz), 4.56(2H, br. d, J=12.6Hz), 7.0-7.9(14H, m), 8.44(1H, d, J=5.2Hz) |
| 604 | 100 | 44-48 | 1.2-1.8(6H, m), 2.36(3H, s), 3.28(4H, m), 3.64(3H, s), 6.50(1H, dd. J=7.2, 1.5Hz), 7.20(2H, d, J=7.2Hz), 7.2-7.6(5H, m), 7.85(2H, d, J=7.2Hz) 8.39(1H, d, J=7.2Hz) |
| 612 | 100 | 44-48 | 0.5-1.1(2H, m), 0.89(3H, d, J=5.2Hz), 1.4-1.8(3H, m), 2.36(3H, s), 2.3-2.9(2H, m), 3.64(3H, s), 3.85(2H, br. d, J=12.6Hz), 6.53(1H, d, J=7.2Hz), 7.19(2H, d, J=7.2Hz), 7.2-7.6(5H, m), 7.84(2H, d, J=7.2Hz), 8.36(1H, d, J=7.2Hz) |
| 620 | 84 | 106-110 | 0.82(9H, s), 0.9-1.8(5H, m), 2.0-3.0(2H, m), 2.36(3H, s), 3.61(3H, s), 4.0(2H, br. d, J=12.6Hz), 6.72(1H, d, J=7.2Hz), 7.18(2H, d, J=7.2Hz), 7.2-7.6(5H, m), 7.84(2H, d, J=7.2Hz), 8.42(1H, d, J=7.2Hz) |
| 628 | 84 | 160-161 | 1.0-2.0(4H, m), 2.35(3H, s), 2.4-3.2(3H, m), 3.64(3H, s), 4.05(2H, br. d, J=12.6Hz), 6.72(1H, d, J=7.2Hz), 7.0-7.6(12H, m), 7.84(2H, d, J=7.2Hz), 8.49(1H, d, J=7.2Hz) |
| 636 | 83 | 143-147 | 1.30(3H, t, J=7.2Hz), 1.0-2.0(4H, m), 2.35(3H, s), 2.4-3.3(3H, m), 4.10(2H, br. d, J=12.6Hz), 4.17(2H, q, J=7.2Hz), 6.80(1H, d, J=7.2Hz) 7.0-7 6(12H, m), 7.84(2H, d, J=7.2Hz), 8.48(1H, d, J=7.2Hz) |
| 644 | 96 | 178-180 | 0.95(3H, t, J=7.2Hz), 1.4-2.1(6H, m), 2.37(3H, s), 2.5-3.3(3H, m), 3.9-4.3(4H, m), 6.67(1H, d, J=7.2Hz), 7.0-8.0(14H, m), 8.55(1H, d, J=7.2Hz) |
| 652 | 87 | 66-68 | 1.0-2.0(4H, m), 1.44(3H, s), 1.52(3H, s), 2.36(3H, s), 2.5-3.3(3H, m), 3.9-4.5(2H, m), 4.76(1H, m), 6.78(1H, d, J=7.2Hz), 7.0-7.7(12H, m), 7.83(2H, d, J=7.2Hz), |

TABLE 4-continued

| Compound No. | Yield (%) | Melting point (°C.) | $^1$H-NMR spectrum (CDCl$_3$ solution, δppm) |
|---|---|---|---|
| 660 | 91 | 116–120 | 8.39(1H, d, J=7.2Hz) 1.2–2.0(4H, m), 2.33(3H, s), 2.4–3.2(3H, m), 4.04(2H, br. d, J=12.6Hz), 5.36(2H, s), 6.56(1H, d, J=7.2Hz), 6.9–7.9(19H, m), 8.38(1H, d, J=7.2Hz) |
| 668 | 82 | 173–175 | 0.9–2.0(4H, m), 2.35(3H, s), 2.4–3.3(3H, m), 3.6(3H, s), 4.12(2H, br. d, J=12.6Hz), 6.82(1H, d, J=7.2Hz) 7.0–7.9(13H, m), 8.45(1H, d, J=7.2Hz) |
| 676 | 79 | 199–200 | 1.0–2.0(4H, m), 2.36(3H, s), 2.5–3.2(3H, m), 3.64(3H, s), 4.14(2H, br. d, J=12.6Hz), 6.80(1H, d, J=7.2Hz) 6.95–7.50(7H, m), 7.76(4H, m), 8.20(2H, d, J=7.2Hz), 8.46(1H, d, J=7.2Hz) |
| 684 | 86 | 60–66 | 1.3–2.1(4H, m), 2.33(3H, s), 2.5–3.3(3H, m), 3.60(3H, s), 4.30(2H, br. d, J=12.6Hz), 6.48(1H, dd, J=4.0, 1.0Hz), 6.87(1H, d, J=7.2Hz) 7.0–7.5(9H, m), 7.82(2H, d, J=7.2Hz), 8.52(1H, d, J=7.2Hz) |
| 692 | 100 | 56–60 | 0.3–1.9(5H, m), 2.33(3H, s), 2.44(2H, d, J=7.2Hz), 2.2–3.1(2H, m), 3.57(3H, s), 3.89(2H, br. d, J=12.6Hz), 6.64(1H, d, J=7.2Hz), 6.9–7.9(14H, m), 8.40(1H, d, J=7.2Hz) |
| 700 | 96 | 136–138 | 2.5(2H, q, J=5.2Hz), 2.32(3H, s), 2.51(3H, s), 2.79(2H, t, J=5.2Hz), 3.58(3H, s), 4.04(2H, t, J=5.2Hz), 6.95(1H, d, J=7.2Hz), 7.11(2H, d, J=7.0Hz), 7.30(4H, s), 7.78(2H, d, J=7.2Hz), 8.58(1H, d, J=7.2Hz) |
| 256 | 100 | 65–70 | 1.2–2.2(4H, m), 2.34(3H, s), 2.5–3.4(3H, m), 3.46(3H, s), 4.5(2H, br. d, J=12.6Hz), 6.9–7.6(12H, m), 7.78(2H, d, J=7.2Hz), 8.40(1H, d, J=7.2Hz) |
| 288 | 100 | 80–85 | 1.2–2.0(4H, m), 2.32(3H, s), 2.5–3.3(3H, m), 3.55(3H, s), 4.47(2H, br. d, J=12.6Hz), 6.62(1H, d, J=7.2Hz) 6.9–7.9(18H, m), 8.33(1H, d, J=7.2Hz) |
| 138 | 66 | 121–123 | 0.88(3H, d, J=7Hz), 1.1–3.1(10H, m) 3.49(3H, s), 4.20(2H, m), 6.54(1H, d, J=7Hz), 7.12(2H, d, J=7Hz), 7.48(5H, m), 7.74(2H, d, J=7Hz), 8.26(1H, d, J=7Hz) |
| 146 | 93 | 98–102 | 0.85(3H, t, J=7Hz), 1.0–3.2(15H, m) 3.47(3H, s), 4.26(2H, m), 6.58(1H, d, J=7Hz), 7.10(2H, d, J=7Hz), 7.48(5H, m), 7.72(2H, d, J=7Hz), 8.18(1H, d, J=7Hz) |
| 147-1 | 44 | 98–100 | 0.85(6H, d, J=7Hz), 1.0–3.2(11H, m) 3.48(3H, s), 4.37(2H, m), 6.50(1H, d, J=7Hz), 7.10(2H, d, J=7Hz), 7.48(5H, m), 7.74(2H, d, J=7Hz), 8.24(1H, d, J=7Hz) |
| 154 | 68 | 52–55 | 1.16(3H, d, J=7Hz), 1.60(5H, m), 2.34(3H, s), 2.5–3.3(2H, m), 3.50(3H, s), 4.18(1H, m), 4.52(1H, m), 6.50(1H, d, J=7Hz), 7.12(2H, d, J=7Hz), 7.48(5H, m), 7.76(2H, d, J=7Hz) 8.28(1H, d, J=7Hz) |
| 171-3 | 81 | 128–129 | 1.3–2.2(4H, m), 2.33(3H, s), 2.40(3H, s), 2.5–3.4(3H, m), 3.52(3H, s), 4.58(2H, br. d, J=12.6Hz), 6.48(1H, d, J=7.2Hz), 7.0–7.9(13H, m), 8.28(1H, d, J=7.2Hz), 13.0–15.0(1H, m) |
| 2004 | 64 | 167–169 | 0.89(6H, d, J=7Hz), 1.3–2.7(9H, m), 3.50(3H, s), 4.26(2H, m), 6.52(1H, d, J=7Hz), 7.12(2H, d, J=7Hz), 7.48(5H, m), 7.76(2H, d, J=7Hz), 8.28(1H, d, J=7Hz) |
| 2012 | 83 | 186–187 | 1.4–2.2(4H, m), 2.33(3H, s), 2.44(3H, s), 2.5–3.4(3H, m), 3.55(3H, s), 4.65(2H, br. d, J=12.6Hz), 8.35(1H, d, J=7.2Hz) |
| 2020 | 100 | 54–60 | 1.7–2.2(4H, m), 2.34(3H, s), 2.5–3.3(3H, m), 3.4–3.7(2H, m), 3.55(3H, s), 6.9–7.9(17H, m), 8.35(1H, m) |
| 2028 | 100 | 60–70 | 2.4–3.1(4H, m), 2.35(3H, s), 2.5–3.2(3H, m), 3.50(3H, s), 4.24(2H, br. d, J=12.6Hz), 7.0–7.5(12H, m), 7.75(2H, m), 8.04(2H, m) |
| 2036 | 100 | 54–58 | 1.4–2.1(8H, m), 2.32(6H, m), 2.2–3.3(6H, m), 3.55(3H, s), 4.50(4H, m), 6.95–7.8(23H, m), 9.1(2H, m) |
| 2044 | 100 | 62–72 | 1.4–2.2(4H, m), 2.35(3H, s), 2.5–3.4(3H, m), 3.59(3H, s), 4.36(2H, br. d, J=12.6Hz), 6.48(1H, dd, J=3.6, 2.0Hz), 7.0–7.6(9H, m), 7.76(2H, d, J=7.2Hz), 7.97(1H, s), 8.15(1H, s), 10.92(1H, m) |
| 2116 | 78 | 138–140 | 0.96(6H, s), 1.36(4H, m), 2.33(3H, s), 3.48(3H, s), 3.60(4H, m), 6.50(1H, d, J=7Hz), 7.12(2H, d, J=7Hz), 7.48(5H, m), 7.74(2H, d, J=7Hz), 8.24(1H, d, J=7Hz) |
| 2124 | 61 | 145–147 | 0.91(3H, t, J=7Hz), 1.60(2H, m), 2.34(3H, s), 2.7–4.0(9H, m), 6.54(1H, d, J=7Hz), 7.0–7.6(12H, m) 7.76(2H, d, J=7Hz), 8.37(1H, d, J=7Hz) |
| 2132 | 61 | 175–178 | 1.4–2.2(4H, m), 2.32(3H, s), 2.6–3.4(3H, m), 3.59(3H, s), 4.68(2H, br. d, J=12.6Hz), 6.63(1H, d, J=7.2Hz) 7.0–7.4(8H, m), 7.45–7.90(4H, m), 8.28(1H, d, J=7.2Hz), 12–14(1H, m) |
| 2140 | 100 | 82–88 | 1.1–2.0(4H, m), 2.31(6H, s), 2.4–3.2(3H, m), 3.5(3H, s), 4.18(2H, br. d, J=12.6Hz), 6.81(1H, d, J=7.2Hz), 6.9–7.4(9H, m), 7.55–8.0(5H, m), 8.2–8 6(2H, m), 8.85(1H, d, J=5.2Hz), 9.10(1H, s), 9.62(2H, m) |
| 2174 | 62 | 94–100 | 1.2–3.3(10H, m), 3.47(3H, s), 4.34(2H, m), 6.55(1H, d, J=7Hz), 6.9–7.9(14H, m), 8.08(1H, d, J=7Hz) |
| 2182 | 78 | >300 | 1.5–2.1(4H, m), 2.32(3H, s), 2.4–3.2(2H, m), 3.48(3H, s), 4.07–4.7(3H, m), 6.46(1H, d, J=7Hz) 6.72(2H, d, J=7Hz), 7.18(7H, m), 7.48(2H, d, J=7Hz), 7.68(2H, d, J=7Hz), 7.88(1H, d, J=7Hz) |
| 2188 | 60 | 151–156 | 1.4–3.2(10H, m), 3.41(3H, s), 4.40(2H, m), 6.50(1H, d, J=7Hz), 7.08(2H, d, J=7Hz), 7.42(5H, m), 7.66(2H, d, J=7Hz), 7.88(1H, d, J=7Hz) |

TABLE 4-continued

| Compound No. | Yield (%) | Melting point (°C.) | $^1$H-NMR spectrum (CDCl$_3$ solution, δppm) |
|---|---|---|---|
| 2194 | 39 | 106–109 | 1.4–3.3(10H, m), 3.45(3H, s), 4.52(2H, m), 6.50(1H, d, J=7Hz), 7.0–8.1(19H, m) |
| 2202 | 52 | 203–207 | 1.5–3.4(10H, m), 3.46(3H, s), 4.44(2H, m), 6.60(1H, d, J=7Hz), 7.10(2H, d, J=7Hz), 7.2–7.9(13H, m) |
| 2210 | 100 | 62–66 | 1.3–2.2(10H, m), 2.31(3H, s), 2.5–3.6(7H, m), 3.25(3H, s), 4.72(2H, br. d, J=12.6Hz), 6.10(1H, d, J=7.2Hz), 7.0–7.4(7H, m), 7.75(2H, d, J=7.2Hz), 8.16(1H, d, J=7.2Hz) |
| 2218 | 89 | 186–187 | 1.4–2.2(4H, m), 2.31(3H, s), 2.6–3.4(3H, m), 3.49(3H, s), 4.63(2H, br. d, J=12.6Hz), 6.76(1H, d, J=7.2Hz), 7.95(1H, d, J=7.2Hz), 10.20(1H, s) |
| 2234 | 94 | 95–102 | 1.45–2.15(4H, m), 2.32(6H, s), 2.5–3.2(3H, m), 2.80(3H, s), 3.23(3H, s), 3.35(4H, m), 3.80(4H, m), 4.60(2H, br. d, J=12.6Hz), 6.62(1H, d, J=7.2Hz), 6.96–7.45(9H, m), 7.76(4H, d, J=7.2Hz), 8.23(1H, d, J=7.2Hz) |
| 2242 | 76 | 116–117 | 1.40(3H, t, J=7.2Hz), 1.4–2.2(4H, m), 2.34(3H, s), 2.6–3.5(3H, m), 3.48(3H, s), 4.35(2H, q, J=7.2Hz), 4.76(2H, br. d, J=12.6Hz), 7.0–7.4(7H, m), 7.6(1H, d, J=7.2Hz), 7.78(2H, d, J=7.2Hz), 8.35(1H, d, J=7.2Hz), 14.0(1H, m) |
| 2250 | 30 | 192–196 | 1.50–3.40(10H, m), 3.50(5H, s), 4.05(2H, s), 4.70(2H, m), 7.10(2H, d, J=7Hz), 7.23(10H, m), 7.48(1H, d, J=7Hz), 7.76(2H, d, J=7Hz), 8.35(1H, d, J=7Hz) |
| 2260 | 45 | 166–173 | 0.85(3H, t, J=7Hz), 1.1–2.2(8H, m), 2.33(3H, s), 2.82(4H, m), 3.46(3H, s), 5.10(1H, m), 6.28(1H, d, J=7Hz), 7.10(2H, d, J=7Hz), 7.36(5H, m), 7.66(2H, d, J=7Hz), 7.96(1H, d, J=7Hz), 8.76(2H, m) |
| 2270 | 50 | 168–169 | 1.52(4H, m), 2.30(3H, s), 2.4–3.2(3H, m), 3.42(3H, s), 4.40(2H, m), 6.46(1H, d, J=7Hz), 7.04(2H, d, J=7Hz), 7.36(15H, m), 7.66(2H, d, J=7Hz), 8.21(1H, d, J=7Hz) |
| 2278 | 86 | 163–164 | 1.4–2.2(4H, m), 2.35(3H, s), 2.5–3.4(6H, m), 4.5–5.0(4H, m), 6.10(1H, d, J=7.2Hz), 7.0–7.5(12H, m), 7.80(2H, d, J=7.2Hz), 8.15(1H, m), 13.15(1H, m) |
| 2286 | 90 | 204–207 (Decomp.) | 1.4–2.15(4H, m), 2.33(3H, s), 2.5–3.3(3H, m), 3.48(3H, s), 4.70(2H, br. d, J=12.6Hz), 5.05(2H, s), 6.7–7.5(13H, m), 7.68(2H, m), 8.35(1H, m) |
| 2294 | 100 | 48–52 | 1.4–2.15(4H, m), 2.32(3H, s), 2.6–3.2(3H, m), 3.0(6H, s), 3.26(3H, s), 4.73(2H, br. d, J=12.6Hz), 6.10(1H, d, J=7.2Hz), 7.0–7.4(7H, m), 7.76(2H, d, J=7.2Hz), 8.18(1H, d, J=7.2Hz) |
| 2302 | 71 | 50–55 | 1.21(6H, t, J=7.2Hz), 1.5–2.2(4H, m), 2.32(3H, s), 2.5–3.7(10H, m), 4.70(2H, br. d, J=12.6Hz), 7.76(2H, d, J=7.2Hz), 8.18(1H, m), 13.33(1H, m) |
| 2310 | 60 | 174–176 | 1.88(4H, m), 2.32(3H, s), 3.40(3H, m), 3.51(3H, s), 4.32(2H, m), 6.60(1H, d, J=7Hz), 7.10(2H, d, J=7Hz), 7.40(2H, d, J=7Hz), 7.50(5H, m), 7.74(2H, d, J=7Hz), 7.84(2H, d, J=7Hz), 8.24(1H, d, J=7Hz) |
| 2318 | 67 | 80–85 | 1.4–2.1(4H, m), 2.6–3.4(3H, m), 3.92(3H, s), 7.0(1H, d, J=7Hz), 7.18(2H, d, J=7Hz), 7.1–7.8(10H, m) 7.78(2H, d, J=7Hz), 8.50(2H, d, J=7Hz) |
| 2322 | 92 | 192–194 | 1.4–2.2(4H, m), 2.32(3H, s), 2.5–3.4(3H, m), 3.29(3H, s), 3.58(8H, m), 4.69(2H, br. d, J=12.6Hz), 6.20(1H, d, J=7.2Hz), 6.95–7.42(7H, m), 7.74(2H, d, J=7.2Hz), 8.23(1H, d, J=7.2Hz) |
| 2330 | 78 | 160–162 | 1.4–2.2(4H, m), 2.32(3H, s), 2.6–3.6(3H, m), 3.69(3H, s), 4.79(2H, br. d, J=12.6Hz), 7.0–7.9(15H, m), 8.40(1H, d, J=7.2Hz) |
| 154-2 | 86 | 191–193 | 1.4–2.2(4H, m), 2.32(3H, s), 2.5–3.4(3H, m), 3.44(3H, s), 3.47(3H, s), 4.4(2H, q), 4.70(2H, br. d, J=12.6Hz), 7.0–7.46(6H, m), 7.75(2H, d, J=7.2Hz), 8.40(1H, d, J=7.2Hz) |
| 171-5 | 74 | 172–173 | 1.41(3H, t, J=7.2Hz), 1.4–2.2(4H, m), 2.32(3H, s), 2.5–3.4(3H, m), 3.52(3H, s), 4.05(2H, q, J=7.2Hz), 4.60(2H, br. d, J=12.6Hz), 6.40(1H, d, J=7.2Hz), 6.89(2H, d, J=7.2Hz), 7.0–7.5(7H, m), 7.56(2H, d, J=7.2Hz), 7.75(2H, d, J=7.2Hz), 8.22(1H, d, J=7.2Hz) |
| 171-5 | 74 | 172–173 | |
| 298 | 70 | 217–218 | 1.6–2.2(4H, m), 2.35(3H, s), 2.7–3.5(3H, m), 4.90(2H, m), 7.22(8H, m), 7.88(6H, m), 8.75(1H, d, J=7Hz) |
| 306 | 70 | 108–110 | 1.88(4H, m), 2.31(3H, s), 3.42(3H, m), 3.51(3H, s), 4.30(2H, m), 6.58(1H, d, J=7Hz), 7.10(2H, d, J=7Hz), 7.50(8H, m), 7.72(2H, d, J=7Hz), 7.88(2H, m), 8.24(1H, d, J=7Hz) |
| 242 | 93 | 119–122 | 1.3–2.2(4H, m), 2.33(3H, s), 2.5–3.4(3H, m), 3.52(3H, s), 4.55(2H, br. d, J=12.6Hz), 6.59(1H, d, J=7.2Hz), 7.0–7.5(9H, m), 7.5–8.0(4H, m), 8.35(1H, d, J=7.2Hz) |
| 2022-1 | 46 | 118–121 | 1.75–2.90(4H, m), 2.35(3H, s), 2.95–3.40(3H, m), 3.55(3H, s), 3.68(2H, br. d, J=12.6Hz), 6.9–8.0(16H, m), 8.70(1H, br. s) |
| 2023-1 | 100 | 57–64 | 1.8–3.0(4H, m), 2.38(3H, s), 3.1–4.0(5H, m), 3,59(3H, s), 6.70–8.0(15H, m) |
| 150 | 100 | 48–58 | 0.5–1.8(5H, m), 0.87(3H, d, J=5.2Hz), 2.35(3H, s), 2.4–3.2(2H, m), 3.4–4.5(2H, m), 6.22(1H, d, J=7.2Hz), 7.0–7.9(14H, m), 8.28(1H, d, J=7.2Hz) |
| 171-9 | 88 | 137–139 | 1.2–2.2(4H, m), 2.32(3H, s), 2,5–3.4(3H, m), 3.51(3H, s), 4.44(2H, br. d, J=12.6Hz), 6.84(1H, d, J=7.2Hz), |

TABLE 4-continued

| Compound No. | Yield (%) | Melting point (°C.) | 1H-NMR spectrum (CDCl3 solution, δppm) |
|---|---|---|---|
| 170-11 | 100 | 75–80 | 6.9–7.9(14H, m), 8.40(1H, d, J=7.2Hz) 1.3–2.2(4H, m), 2.32(3H, s), 2.5–3.5(3H, m), 3.45(3H, s), 4.48(2H, br. d, J=12.6Hz), 6.95–7.5(11H, m), 7.72(2H, d, J=7.2Hz), 8.44(1H, d, J=7.2Hz) |
| 170-2 | 88 | 147–148 | 1.4–2.1(4H, m), 2.33(3H, s), 2.5–3.5(3H, m), 3.55(3H, s), 4.72(2H, br. d, J=12.6Hz), 6.8–8.0(17H, m), 8.40(1H, d, J=7.2Hz) |
| 171-7 | 95 | 70–76 | 1.3–2.1(4H, m), 2.32(3H, s), 2.36(3H, s), 2.5–3.3(3H, m), 3.44(3H, s), 4.56(2H, br. d, J=12.6Hz), 6.80(1H, d, J=7.2Hz), 9.0–9.6(11H, m), 7.73(2H, d, J=7.2Hz), 8.30(1H, d, J=7.2Hz) |
| 171-13 | 97 | 154–158 | 1.2–2.1(4H, m), 2.3(3H, s), 2.5–3.3(3H, m), 3.48(3H, s), 4.4(2H, br. d, J=12.6Hz), 6.7(1H, d, J=7.2Hz), 7.0–7.9(12H, m), 8.39(1H, d, J=7.2Hz) |

EXAMPLE 3

4-(N-Methylbenzamino)-2-(4-Phenylpiperidino)Pyrimidine Hydrochloride (Coompound No. 170)

A solution of 0.27 g (0.0027 mole) of concentrated hydrochloric acid in 2 ml of $CH_3OH$ was slowly added to a solution of 1.0 g (0.0027 mole) of 4-(N-methylbenzamino)-2-(4-phenylpiperidino)pyrimidine in 10 ml of chloroform. After the addition, the mixture was concentrated under reduced pressure to give 1.1 g (yield 100%) of the desired product.

Melting point: 80°–84° C.

1H-NMR spectrum (deuterochloroform, δ ppm) 1.4–22(4H, m), 2.6–3.4(3H, m), 3.56(3H, s), 2.2(2H, m), 6.69(1H, d, J=7.2 Hz), 7.0–7.7(10H, m), 8.1(1H, d, J=7.2 Hz).

In the same way as above, the following compounds were produced, and their data are given in Table 5.

TABLE 5

| Compound No. | Yield (%) | Melting point (°C.) | 1H-NMR spectrum (CDCl3 solution, δppm) |
|---|---|---|---|
| 662 | 46 | 241–243 | 10.9(1H, br), 8.03(1H, d, J=5Hz), 7.2–7.8(10H, m), 6.28(1H, d, J=5Hz), 4.63(2H, s), 3.50(3H, s), 3.0–3.4(1H, m), 1.48(6H, d, J=7Hz) |
| 2052 | 86 | 96–99 | 12.9(2H, br), 8.03(1H, d, J=5Hz), 7.2–7.6(5H, m), 6.36(1H, d, J=5Hz), 4.5–4.8(2H, m), 3.56(3H, s), 1.1–3.3(17H, m) |
| 2060 | 93 | 185–189 | 7.98(1H, d, J=7Hz), 7.3–7.7(5H, m), 6.64(1H, d, J=7Hz), 3.6–4.4(6H, m), 3.62(3H, s), 1.4–2.2(4H, m) |
| 2070 | 93 | 77–80 | 8.03(1H, d, J=5Hz), 7.2–7.6(5H, m), 6.36(1H, d, J=5Hz), 4.0–4.7(2H, m), 3.63(3H, s), 1.0–4.0(12H, m) |
| 2076 | 86 | 237–239 | 12.5(1H, br), 8.53(1H, d, J=5Hz), 8.12(9H, d, J=7Hz), 7.32(2H, d, J=7Hz), 6.43(1H, d, J=5Hz), 7.2–7.7(5H, m), 4.8–5.0(2H, m), 3.53(3H, s), 1.1–3.4(7H, m) |
| 2084 | 90 | 60–63 | 12.3(1H, br), 8.70(1H, d, J=7Hz), 7.2–7.6(5H, m), 6.37(1H, d, J=7Hz), 4.0–4.8(2H, m), 2.63(3H, s), 0.8–3.5(14H, m) |
| 2092 | 86 | 183–186 | 8.06(1H, d, J=7Hz), 7.2–7.6(5H, m), 6.38(1H, d, J=7Hz), 3.60(3H, s), 3.10(3H, s), 1.8–4.0(10H, m) |
| 2100 | 90 | 213–215 | 8.70(1H, d, J=5Hz), 7.3–7.6(5H, m), 6.48(1H, d, J=5Hz), 4.4–4.8(2H, m), 4.20(2H, q, J=7Hz), 3.58(3H, s), 1.32(3H, t, J=7Hz), 1.5–3.4(7H, m) |
| 2108 | 93 | 89–91 | 10.5(1H, br), 8.07(1H, d, J=5Hz), 7.0–7.6(15H, m), 6.18(1H, d, J=5Hz), 4.68(4H, s), 3.44(3H, s) |
| 2148 | 94 | 218–221 | 8.05(1H, d, J=7Hz), 7.2–7.5(5H, m), 6.40(1H, d, J=7Hz), 4.3 4.5(2H, m), 2.3–4.0(7H, m), 3.30(5.6H), 3.58(3H, s) |
| 2156 | 89 | 57–60 | 14.0(1H, br), 8.04(1H, d, J=7Hz), 7.3–7.6(5H, m), 6.56(1H, d, J=7Hz), 3.50(3H, s), 4.0–4.8(2H, m), 1.0–2.4(14H, m) |
| 2164 | 96 | 140–142 | 8.03(1H, d, J=5Hz), 7.2–7.6(5H, m), 6.40(1H, d, J=5Hz), 4.2–4.5(2H, m), 3.63(3H, s), 1.0–3.8(10H, m) |
| 2226 | 86 | 187–189 | 7.9–8.1(3H, m), 7.2–7.7(8H, m), 6.66(1H, d, J=7Hz), 5.1–5.4(1H, m), 3.6–4.3(4H, m), 3.55(3H, s), 1.7–2.2(4H, m) |
| 2342 | 94 | 135–138 | 12.0–12.8(1H, br), 8.03(1H, d, J=7Hz), 7.2–7.6(5H, m), 6.50(1H, d, J=7Hz), 3.53(3H, s), 1.0–3.7(13H, m) |
| 2350 | 88 | 153–157 | 12.8(1H, br), 8.03(1H, d, J=7Hz), 7.2–7.9(10H, m), 6.60(1H, d, J=7Hz), 4.3–4.6(2H, m), 3.50(3H, s), 1.5–4.0(7H, m) |
| 307-1 | 94 | 259–261 | 8.07(1H, d, J=7Hz), 7.2–7.6(5H, m), 6.38(1H, d, J=7Hz), 4.2–4.4(2H, m), 3.50(3H, s), 1.4–4.0(10H, m) |

The following compounds were obtained by the same method as in Example 3 except that sulfuric acid, phosphoric acid, etc. were used instead of hydrochloric acid.

TABLE 6

| Compound No. | Yield (%) | Melting point (°C.) | 1H-NMR spectrum (CDCl3 solution, δppm) |
|---|---|---|---|
| 165 | 84 | 151–154 | 1.0–2.0(4H, m),2.5–3.2(3H, m), 3.45(3H, s), 4.24(2H, br. d, J=12.6Hz), 6.67(1H, d, J=7.2Hz), |

TABLE 6-continued

| Compound No. | Yield (%) | Melting point (°C.) | $^1$H-NMR spectrum (CDCl$_3$ solution, δppm) |
|---|---|---|---|
| 166 | 67 | 108–113 | 6.73(1H, d, J=7.2Hz), 7.0–7.6(10H, m), 8.15(1H, d, J=7.2Hz) 1.2–2.0(4H, m), 2.5–3.0(3H, m), 3.51(3H, s), 4.58(2H, br. d, J=12.6Hz), 6.15(1H, d, J=5.4Hz), 7.0–7.55(10H, m), 8.02(1H, d, J=5.4Hz), 11.0(1H, m) |
| 167 | 37 | 94–96 | 1.3–2.2(4H, m), 2.6–3.2(3H, m), 3.52(3H, s), 4.54(2H, br. d, J=12.6Hz), 6.32(2H, s), 6.49(1H, d, J=7.2Hz), 7.0–7.7(10H, m), 8.15(1H, d, J=7.2Hz), 8.93(2H, br. s) |
| 169 | 32 | 132–136 | 1.3–2.2(4H, m), 2.55–3.3(3H, m), 3.49(3H, s), 4.49(2H, br. d, J=12–6Hz), 6.58(1H, d, J=7.2Hz), 6.8–8.5(19H, m) |
| 171 | 45 | 108–112 | 1.0–1.9(4H, m), 2.4–2.9(6H, m), 3.0–3.6(3H, m), 3.40(3H, s), 4.36(2H, br. d, J=12.6Hz), 6.42(1H, d, J=5.4Hz), 7.0–7.4(5H, m), 7.35(5H, s), 8.15(1H, d, J=5.4Hz), 12–13(2H, m) |
| 171-1 | 49 | 133–135 | 1.0–1.8(4H, m), 2.4–2.9(3H, m), 3.0–3.5(3H, m), 3.40(3H, s), 4.30(2H, s), 4.38(2H, br. d, J=12.6Hz), 6.42(1H, d, J=5.4Hz), 7.0–7.4(5H, m), 7.35(5H, s), 8.15(1H, d, J=5.4Hz), 12–13(1H, m) |
| 171-1-1 | 90 | 124–127 | 1.2–2.0(4H, m), 2.5–3.0(3H, m), 3.48(3H, s), 4.55(2H, br. d, J=12.6Hz), 6.17(1H, d, J=5.4Hz), 6.69(2H, s), 6.9–7.5(10H, m), 8.02(1H, d, J=5.4Hz) |

EXAMPLE 4

Production of 2-Isopropylamino-4-Methyl-5-Methoxycarbonyl-pyrimidine (Compound No. 800)

18.2 g (0.12 mole) of 1-amidinoisopropylamine sulfate was added to a solution of 13.0 g (0.12 mole) of potassium t-butoxide in 200 ml of methanol, and the mixture was stirred at room temperature for 30 minutes. Then, 18.5 g (0.12 mole) of ethyl 2-methoxymethyleneacetoacetate was added at 0° C. over 30 minutes, and the mixture was stirred for 3 hours. The solvent was evaporated, and the residue was extracted with ether and purified by silica gel column chromatography to give 10.6 g (yield 44%) of the desired product as a yellow solid.

Melting point: 118°–119° C.

$^1$H-NMR spectrum (deuterochloroform, δ ppm) 1.26(6H, d, J=7 Hz), 2.66(3H, s), 3.87(3H, a), 4.25(1H, sex, J=7 Hz), 5.40(1H, br. s), 8.80(1H, s).

EXAMLPLE 5

Production of 2-Piperidino-4-Methoxymethyl-5-Methoxycarbonyl-pyrimidine (Compound No. 820)

Sodium hydride (0.19 g; 7.8 mmoles) was added to 50 ml of methanol, and 2.1 g (7.8 mmoles) of 2-piperidino-4-chloromethyl-5-methoxycarbonylpyrimidine was added at room temperature. The mixture was stirred for 3 hours. After the solvent was evaporated, water was added to the residue and the mixture was extracted with ethyl acetate. The ethyl acetate layer was dried over anhydrous sodium sulfate and concentrated under reduced pressure. The residue was purified by silica gel chromatography to give 0.90 g (yield 44%) of the desired product as a white solid.

Melting point: 89°–92° C.

$^1$H-NMR spectrum (deuterochloroform, δ ppm): 1.70(6H, m), 3.54(3H, s), 3.86(3H, s), 3.92(4H, m), 4.83(2H, s), 8.82(1H, s).

In the same way as above, the following compounds were obtained.

TABLE 7

| Compound No. | Yield (%) | Melting point (°C.) | $^1$H-NMR spectrum (CDCl$_3$ solution, δppm) |
|---|---|---|---|
| 808 | 53 | Oil | 1.35(3H, t, J=7Hz), 1.66(6H, m), 2.44(3H, s), 3.90(2H, s), 3.92(4H, m), 4.30(2H, q, J=7Hz), 8.80(1H, s) |
| 816 | 35 | Oil | 1.40(3H, t, J=7Hz), 1.70(6H, m), 2.21(3H, s), 3.92(4H, m), 4.06(2H, s), 4.36(2H, q, J=7Hz), 8.91(1H, s) |
| 824 | 90 | Oil | 1.22(6H, d, J=8Hz), 1.33(3H, t, J=8Hz), 2.36(6H, s), 3.84(2H, s), 5.5(1H, br,s), 8.78(1H, s) |

EXAMPLE 6

Production of 2-Isopropylamino-4-Methyl-5-Methoxycarbonyl-pyrimidine Maleate (Compound No. 804)

2.48 g (11.9 g mmoles) of 2-isopropylamino-4-methyl-5-methoxycarbonylpyrimidine and 1.38 g (11.9 mmoles) of maleic acid were dissolved in a mixture of 20 ml of ethanol and 20 ml of chloroform, and the solution was stirred for 3 hours. The solvents were evaporated, and ether was added for crystallization at 0° C. The desired product was obtained in an amount of 3.21 g (yield 83%) as pale yellow crystals.

Melting point: 75°–79° C.

$^1$H-NMR spectrum (deuterochloroform, δ ppm): 1.33(6H, d, J=7 Hz), 2.85(3H, s), 3.95(3H, s), 4.36(1H, sex, J=7 Hz), 6.40(2H, s), 9.08(1H, br, s).

In the same way as above, the following compounds were produced.

TABLE 8

| Compound No. | Yield (%) | Melting point (°C.) | $^1$H-NMR spectrum (CDCl$_3$ solution, δppm) |
|---|---|---|---|
| 812 | 74 | 115.5–118.5 | 1.40(3H, t, J=7Hz), 1.68(6H, m), 3.08(3H, s), 3.92(4H, m), 4.34(2H, q, J=7Hz), 4.72(2H, s), 6.32(2H, s), 8.90(1H, s) |
| 828 | 67 | 111–121 | 1.30(6H, d, J=8Hz), 1.40(3H, t, J=8Hz), 3.07(6H, s), 4.34(2H, q, J=8Hz), 4.66(2H, s), 6.32(2H, s), 8.92(1H, s) |

EXAMPLE 7

Production of 2-(4-Diphenylmethylpiperazino)-5,6-Dihydro-7-Methyl-6-Oxo(7H)Pyrrolo[2,3-d]Pyrimidine (Compound No. 3124)

1.9 g (7.5 mmoles) of 1-diphenylmethylpiperazine and 1.7 g (7.5 mmoles) of ethyl (2-methylthio-4-hydroxypyrimidin-5-yl)acetate were added to 60 ml of n-amyl alcohol, and the mixture was stirred at 170° C. for 20 hours. The solvent was then evaporated under reduced pressure. Ten milliliters of phosphorus oxychloride was added to the residue, and reacted at 100° C. for 2 hours. After the reaction, the mixture was gradually added to an aqueous solution of potassium carbonate, and extracted with methylene chloride. The organic layer was dried over anhydrous magnesium sulfate, and the solvent was evaporated under reduced pressure. The residue, 15 ml of ethanol and a 40% methanol solution of methylamine was put in a pressure vessel, and reacted at 140° C. for 10 hours. Then, the solvent was evaporated, and the residue was purified by silica gel column chromatography to give 0.9 g (yield 30%) of the desired product.

Melting point: 75°–80° C.

$^1$H-NMR spectrum (CDCl$_3$ solution, δ ppm): 2.43(4H, m), 3.13(3H, s), 3.37(2H, s), 3.80(4H, m), 4.23(1H, s), 7.08–7.52(10H, m), 7.82(1H, s).

The following compounds were produced in the same way as above, and their data are shown in Table 9.

TABLE 9

| Compound No. | Yield (%) | Melting point (°C.) | $^1$H-NMR spectrum (CDCl$_3$ solution, δppm) |
|---|---|---|---|
| 3100 | 78 | 210–213 | 2.47(4H, m), 3.17(3H, s), 3.39(2H, s), 3.50(2H, s), 3.82(4H, m), 7.28(4H, m), 7.88(1H, s) |
| 3108 | 56 | 82–86 | 0.74(3H, d, J=7Hz), 1.02(3H, d, J=7Hz), 2.38(4H, m), 3.13(3H, s), 3.35(2H, s), 3.74(4H, m), 4.10(1H, m), 7.20(5H, m), 7.80(1H, s) |
| 3132 | 38 | 80–85 | 2.42(4H, m), 3.15(3H, s), 3.38(2H, s), 3.81(4H, m), 4.24(1H, s), 6.8–7.5(9H, m), 7.85(1H, s) |
| 3140 | 54 | 105–110 | 2.43(4H, m), 3.15(3H, s), 3.39(2H, s), 3.82(4H, m), 4.24(1H, s), 7.32(9H, m), 7.88(1H, s) |
| 3148 | 35 | — | 2.29(3H, s), 2.43(4H, m), 3.14(3H, s), 3.38(2H, s), 3.80(4H, m), 4.21(1H, s), 6.9–7.5(9H, m), 7.84(1H, s) |
| 3172 | 26 | — | 2.41(4H, m), 3.14(3H, s), 3.36(2H, s), 3.80(4H, m), 4.22(1H, s), 7.28(8H, m), 7.84(1H, s) |
| 3180 | 12 | 91–94 | 2.40(4H, m), 3.14(3H, s), 3.37(2H, s), 3.80(4H, m), 4.23(1H, s), 6.8–7.4(8H, m), 7.83(1H, s) |
| 3188 | 44 | 170–175 | 2.50(4H, m), 3.16(3H, s), 3.40(2H, s), 3.84(4H, m), 4.44(1H, s), 7.1–7.6(8H, m), 7.84(1H, s), 8.49(1H, m) |
| 3196 | 51 | 179–181 | 2.66(4H, m), 3.12(3H, s), 3.36(2H, s), 3.76(4H, m), 4.88(1H, s), 7.28(4H, m), 7.70(4H, m), 7.84(1H, s) |
| 3300 | 49 | 263–267 (decomp.) | 2.36(4H, m), 3.13(3H, s), 3.36(2H, s), 3.92(4H, m), |
| 3400 | 40 | | 7.1–7.6(15H, m), 7.82(1H, s), 2.78(3H, s), 3.18(3H, s), 3.26(4H, m), 3.40(2H, s), 3.94(4H, m), 7.87(1H, s) |
| 3408 | 68 | | 1.1–2.0(12H, m), 3.18(3H, s), 3.32(4H, m), 4.20(2H, m), 7.84(1H, s) |
| 3416 | 61 | | 1.2–2.4(12H, m), 3.18(3H, s), 3.3–3.8(4H, m), 7.86(1H, s) |

EXAMPLE 8

Production of 2-(4-Diphenylmethylpiperazino)-5,6-Dihydro-7-Methyl-6-Oxo(7H)Pyrrolo[2,3-d]Pyrimidine Hydrochloride (Compound No. 3128)

Concentrated hydrochloric acid (0.23 g; 2.2 mmoles) was added to an ethanol/methylene chloride solution of 2-(4-diphenylmethylpiperazino)-5,6-dihydro-7-methyl-6-oxo(7H)pyrrolo[2,3-d]pyrimidine, and the solution was stirred at room temperature for 1 hour. The solvent was then evaporated under reduced pressure. The residue was washed with ether to give 0.88 g (yield 90%).

Melting point: 217°–222° C.

$^1$H-NMR spectrum (CDCl$_3$, δ ppm): 3.18(3H, s), 3.20(4H, m), 3.52(2H, s), 4.40(4H, m), 5.20(1H, s), 7.2–7.9 (1H, m).

In the same way as above, the following compounds were produced, and their data are shown in Table 10.

TABLE 10

| Compound No. | Yield (%) | Melting point (°C.) | $^1$H-NMR spectrum (CDCl$_3$ solution, δppm) |
|---|---|---|---|
| 3104 | 82 | >300 | (CDCl$_3$—CD$_3$OD) 3.20(3H, s), 3.30(4H, m), 3.48(2H, s), 4.32(2H, s), 4.54(4H, m), 7.52(4H, m), 7.93(1H, s) |
| 3136 | 80 | 238–243 (decomp.) | (CDCl$_3$—CD$_3$OD) 3.20(3H, s), 3.24(4H, m), 3.50(2H, s), 3.8–4.6(4H, m), 5.10(1H, s), 7.0–8.0(10H, m) |
| 3144 | 93 | 238–245 (decomp.) | 3.20(3H, s), 3.29(4H, m), 3.57(2H, s), 4.58(4H, m), 5.26(1H, s), 7.40(5H, m), 7.90(5H, m) |
| 3200 | 73 | 244–245 (decomp.) | 3.12(3H, s), 3.14(4H, m), 3.40(2H, s), 4.56(4H, m), 5.45(1H, s), 7.17–8.27(9H, m) |
| 3412 | 70 | 250–252 (decomp.) | 1.2–2.2(12H, m), 3.26(3H, s), 3.52(4H, m), 4.50(2H, m), 8.00(1H, s) |
| 3420 | 70 | 256–257 (decomp.) | 1.2–2.5(12H, m), 3.25(3H, s), 3.3–4.2(4H, m), 7.99(1H, s) |

EXAMPLE 9

Production of 2-(4-(α-(4-Methylphenyl)Benzyl)Piperazino)-5,6-Dihydro-7-Methyl-6-Oxo(7H)Pyrrolo-[2,3-d]Pyrimidine P-Toluenesulfonate (Compound No. 3152)

An ethyl acetate/methanol solution of 0.13 g (0.75 mmole) of p-toluenesulfonic acid was added to an ethyl acetate/methanol solution of 0.31 g (0.75 mmole) of 2-(4-(α(4-methylphenyl)benzyl)piperazino)-5,6-dihydro-7-methyl-6-oxo(7H)pyrrolo[2,3-d]pyrimidine, and the mixture was stirred at room temperature for 1 hour.

The solvents were then evaporated under reduced pressure, and the residue was washed with hexane to give 0.36 g (yield 81%) of the desired compound.

Melting point: 150°–155° C.

¹H-NMR spectrum (CDCl₃ solution, δ ppm): 2.28(3H, s), 2.34(3H, s), 3.00(4H, m), 3.11(3H, s), 3.39(2H, s), 4.14(4H, m), 4.73 (1H, s), 7.0–7.8(13H, m), 7.93(1H, s).

In the same way as abvove, the following compounds were produced, and their data are shown in Table 11.

TABLE 11

| Compound No. | Yield (%) | Melting point (°C.) | ¹H-NMR spectrum (CDCl₃ solution, δ ppm) |
|---|---|---|---|
| 3112 | 92 | — | 0.86(3H, d, J=7Hz), 1.16(3H, d, J=7Hz), 2.35(3H, s), 3.12(7H, m), 3.39(2H, s), 4.20(5H, m), 7.14(2H, d, J=7Hz), 7.35(5H, m), 7.76(2H, d, J=7Hz), 7.87(1H, s) |
| 3176 | 90 | 145–150 | 2.34(3H, s), 2.83(4H, m), 3.13(3H, s), 3.43(2H, s), 4.06(4H, m), 4.72(1H, s), 7.0–7.5(10H, m), 7.66(2H, d, J=7Hz), 8.03(1H, s) |
| 3184 | 91 | 124–130 | 2.34(3H, s), 2.74(4H, m), 3.14(3H, s), 3.43(2H, s), 4.04(4H, m), 4.56(1H, s), 6.8–7.8(12H, m), 8.01(1H, s) |
| 3192 | 100 | 135–140 | 2.35(3H, s), 3.0–3.4(4H, m), 3.16(3H, s), 3.44(2H, s), 4.18(4H, m), 5.34(1H, s), 7.0–7.8(8H, m), 7.11(2H, d, J=7Hz), 7.74(2H, d, J=7Hz), 7.96(1H, s), 8.60(1H, m) |
| 3404 | 70 | 220–223 (decomp.) | (CDCl₃–CD₃OD) 2.38(3H, s), 2.86(3H, s), 3.27(3H, s), 3.38(4H, m), 3.60(2H, s), 4.03(4H, m), 7.16(2H, d, J=7Hz), 7.64(2H, d, J=7Hz), 8.02(1H, s) |

EXAMPLE 1B

Tablets each containing 10 mg of an active ingredient were prepared by the following procedure.

|  | Per tablet |
|---|---|
| Active ingredient | 10 mg |
| Corn starch | 55 mg |
| Crystalline cellulose | 35 mg |
| Polyvinyl pyrrolidone (as 10% aqueous solution) | 5 mg |
| Carboxymethyl cellulose calcium | 10 mg |
| Magnesium stearate | 4 mg |
| Talc | 1 mg |
| Total | 120 mg |

The active ingredient, corn starch and crystalline cellulose were passed through an 80-mesh sieve and thoroughly mixed. The mixed powder was granulated together with the polyvinyl pyrrolidone solution, and passed through an 18-mesh sieve. The resulting granules were dried at 50° to 60° C. and again passed through an 18-mesh sieve to adjust their sizes. The carboxymethyl cellulose calcium, magnesium stearate and talc, which had been passed through an 80-mesh sieve, were added to the granules. They were mixed and tableted by a tableting machine to produce tablets each having a weight of 120 mg.

EXAMPLE 2B

Tablets each containing 200 mg of an active ingredient were produced by the following procedure.

|  | Per tablet |
|---|---|
| Active ingredient | 200 mg |
| Corn starch | 50 mg |
| Crystalline cellulose | 42 mg |
| Silicic anhydride | 7 mg |
| Magnesium stearate | 1 mg |
| Total | 300 mg |

The above components were passed through an 80-mesh sieve and thoroughly mixed. The resulting mixed powder was compression-molded to produce tablets each having a weight of 300 mg.

EXAMPLE 3B

Capsules each containing 100 mg of an active ingredient were produced by the following procedure.

|  | Per capsule |
|---|---|
| Active ingredient | 100 mg |
| Corn starch | 40 mg |
| Lactose | 5 mg |
| Magnesium stearate | 5 mg |
| Total | 150 mg |

The above components were mixed, passed through an 80-mesh sieve, and thoroughly mixed. The resulting mixed powder was filled into capsules in an amount of 150 mg for each.

EXAMPLE 4B

Injectable preparations in vials each containing 5 mg of an active ingredient were produced by the following procedure.

|  | Per vial |
|---|---|
| Active ingredient | 5 mg |
| Mannitol | 50 mg |

Just prior to use, these compounds were dissolved in 1 ml of distilled water for injection, and administered.

EXAMPLE 5B

Injectable preparations in ampoules each containing 50 mg of an active ingredients were produced in accordance with the following recipe.

|  | Per ampoule |
|---|---|
| Active ingredient | 50 mg |
| Sodium chloride | 18 mg |
| Distilled water for injection | proper amount |
| Total | 2 ml |

EXAMPLE 6B

An adhesive patch containing 17.5 mg of an active ingredient was produced by the following procedure.

Ten parts of poly(ammonium acrylate) was dissolved in 60 parts of water. Two parts of glycerin diglycidyl ether was dissolved under heat in 10 parts of water. Furthermore, 10 parts of polyethylene glycol (grade 400), 10 parts of water and 1 part of an active ingredient were stirred to form a solution. While the aqueous solution of poly(ammonium acrylate) was stirred, the aqueous solution of glycerin diglycidiyl ether and the solution containing the active ingredient, polyethylene glycol and water were added and mixed. The resulting solution for hydrogel was coated on a pliable plastic film so that the rate of the active ingredient was 0.5 mg per cm$^2$. The surface was covered with releasing paper and cut to a size of 35 cm$^2$ to form an adhesive patch.

EXAMPLE 7B

An adhesive patch containing 10 mg of an active ingredient was produced by the following procedure.

An aqueous sol is prepared from 100 parts of poly(-sodium acrylate), 100 parts of glycerin, 150 parts of water, 0.2 part of triepoxypropyl isocyanurate, 100 parts of ethanol, 25 parts of isopropyl myristate, 25 parts of propylene glycol and 15 parts of the active ingredient. The sol was then coated to a thickness of 100 micrometers on the non-woven fabric surface of a composite film composed of a rayon non-woven fabric and a polyethylene film to form an adhesive layer containing the drug. The amount of the release aids (isopropyl myristate and propylene glycol) contained in this layer was about 30% by weight. The adhesive layer was then crosslinked at 25° C. for 24 hours, and a releasing film was bonded to the adhesive layer surface. The entire film was then cut into pieces each having an area of 35 cm$^2$.

The biological activities in vitro of the compounds of formula (1), (2) or (3) on cells of the nervous system were tested. The cells tested were mouse neuroblastoma cell line neuro-2a (Dainippon Pharmaceutical Co., Ltd.), NS-20Y, etc. which have been established as the cells of the nervous system. The above nerve cells were grown in an incubator at 37° C. in the presence of 5% carbon dioxide gas exponentially, and then cultivated for a certain period of time together with the compounds of the invention. The results demonstrate that the compounds of the invention have nerve cell growth promoting activity and neurite formation and sprouting promoting activity which are markedly higher with a significance than a control, and are equal to, or higher than, isaxonine as a control drug (the compound described in Japanese Patent Publication No. 28548/1984).

The biological activities of the compounds of the invention on rat PC-12 pheochromocytoma cell line were also tested. When NGF is added to PC-12 cells, the neurites sprout. It was shown that when the compound of this invention is added at this time, the binding of NGF to the PC-12 cells and the up-take of NGF into the cells increased, and that the sprouting of the neurites also increased.

When the effect of the compounds of this invention on the binding of NGF to rabbit superior cervical ganglion was examined, they were found to promote the NGF binding.

Rats having crushed sciatic nerves were prepared as a model of peripheral nervous disorder, and the effects of the compounds of this invention on it were tested. It was made clear that the compounds of the present invention have an effect of promoting recovery of the interdigit distance and the weight of the soleus muscle to normal values.

Rat and mouse models of central nervous disorders were prepared, and the pharmacological effects of the compounds of this invention were tested. Specifically, nigral dopamine cells of the rat brain were chemically destroyed by injecting a very small amount of 6-hydroxydopamine to induce motor imbalance. Two weeks later, dopamine cells of fetal brain were transplanted into the lesioned side of the caudate nucleus of the rat brain and an attempt was made to improve the motor trouble. Specifically, beginning on the day of transplantation, the compound of the invention was intraperitoneally administered every day over 2 weeks, and the activity of the compounds of the invention on the improvement of the motor imbalance and the growth of the transplanted cells were examined. It was found that the compounds of the invention have a promoting effect on the improvement of the motor trouble.

Rats and mice having a nerve trouble by mercury poisoning were prepared and the activity of the compounds of the invention was tested. The compounds of the invention were found to have a promoting effect on the improvement of the condition and recovery to a normal condition, a curative effect on chemical-induced disorders and an effect of improving and recovering learning and memory.

Thus, it has been made clear that the compounds of this invention are useful as agents for improving or curing various neurological diseases of mammals, such as troubles in peripheral and central nerves, and also as agents for improving learning and memory.

Various types of neuropathy including, for example, various peripheral nerve disorders accompanied by motorgenic, seonsory or objective flex retardation, and alcohol-induced or drug-induced, diabetic and metabolic, or idiopathic peripheral nerve disorders, including traumatic, inflammatory or immunological nerve root lesions may be cited as such neurological diseases. More specific examples include facial palsy, sciatic nerve paralysis, spinal muscular atrophy, muscular dystrophy, myasthenia gravis, multiple sclerosis, amyotrophic lateral sclerosis, acute disseminated cerebromyelitis, Guillan-Barre syndrome, postvaccinal encephalomyelitis, SMON disease, dementia, Alzheimer syndrome, a condition after cranial injury, cerebral spinal injury, neural injury disorders which occur in cerebral ischemia, sequela of cerebral infarction or cerebral hemorrhage, and rheumatism. These examples are not limitative.

By a toxicity test, the compounds of this invention were found to have only weak toxicity and side effects, and be used as safe and useful medicines.

EXPERIMENTAL EXAMPLE 1

The effects of the compounds of this invention on neuroblastoma cells were examined by the following method.

Mouse neuro 2a cells in the logarithmic growth period in the Dulbecco's modified Eagle's medium DMEM, containing 100 units/ml of penicillin G sodium and 100 micrograms/ml of streptomycin sulfate) containing 10% of FCS were seeded in a 48-well plate so that the number of cells was 1,000 cells/well, and cultured for one day in 0.25 ml of the culture fluid in each well in an incubator containing 5% of carbon dioxide gas in air at 37° C. Then, a 4% aqueous glutaraldehyde solution in the same amount as a medium (0.25 ml) was added, and the culture fluid was left to stand at room temperature for 2 hours to fix the cells. After washing with water, a 0.05% aqueous solution of methylene blue was added to stain the cells. Under a microscope, the number of cells containing outgrown neurites (cells having at least one neurite with a length of at least two times as large as the long diameter of the cell) was counted visually, and the proportion of these cells in the entire cells was calculated. The well was observed over 5 or more visual fields (at least 2% of the entire surface area of the well) continuous to the left and right from a mark put at the center of the well, and more than 200 cells was counted. One drug compound was used in 6 different concentrations at most, and three runs were conducted for each concentrations. The results were expressed as a mean ±S.D., and the results are shown in Table 12.

Mouse neuroblastoma cells NS-20Y were similarly cultured in a dish coated with polyornithine, and the effects of the compounds were examined. The results obtained after 24 hours and 48 hours from the start of culturing are shown in Table 13.

TABLE 12

| Run No. | Compound | Action on neuro - 2a — Number of cells having neurites with a length at least two times the diameter of each cell/total number of cells, % (concentration of the compound) |
|---|---|---|
| 1 | 1034 | 3.9±2.8(0.03mM), 7.6±2.1(0.1mM), 11.3±1.6(0.3mM) |
|  | 312 | 4.5±0.4(0.03mM), 9.7±0.9(0.1mM) |
|  | isaxonine | 26.7±7.7(10mM) |
|  | control | 1.8±0.8 |
| 2 | 128 | 9.9±0.6(0.3mM), 9.1±0.7(0.5mM), 19.8±2.8(1mM), 14.3±2.4(2mM) |
|  | 208 | 7.2±2.3(0.5mM), 10.6±1.5(1mM), 11.1±1.2(2mM), 8.0+4.0(3mM) |
|  | 168 | 23.8±2(0.05mM), 35.7±0.8(0.1mM), 24.4±6.9(0.2mM), 14.6±4.3(0.3mM) |
|  | isaxonine | 28.5±5.4(10mM) |
|  | control | 1.4±0.2 |
| 3 | 384 | 10.4±2.5(0.3mM), 10.8±7.2(1mM) |
|  | 392 | 14.6±6.0(0.1mM), 30.9±5.7(0.3mM), 23.8±4.2(1mM), 11.1±9.7(3mM) |
|  | 700 | 5.9±1.4(0.1mM), 6.4±1.4(0.3mM) |
|  | isaxonine | 30.8±2.9(10mM) |
|  | control | 3.2±1.6 |
| 4 | 416 | 13.2±1.3(0.1mM), 10.8±1.5(0.3mM) |
|  | 320 | 7.2±0.2(0.1mMO, 8.5±1.1(0.3mM) |
|  | 328 | 6.6±0.5(0.01mM), 10.2±8.2(0.03mM), 28.0±6.8(0.1mM), 10.6±3.4(0.3mM) |
|  | 400 | 11.4±4.3(0.3mM), 16.0±2.7(1mM) |
|  | isaxonine | 30.7±5.9(10mM) |
|  | control | 2.9±1.9 |
| 5 | 136 | 11.6±6.3(0.1mM), 12.1±2.9(0.3mM) |
|  | 628 | 10.2±1.3(0.03mM), 13.4±3.2(0.1mM), 12.6±3.2(0.3mM), 10.0±3.9(1mM) |
|  | 144 | 13.7±7.8(0.1mM), 33.8±8.6(0.3mM) |
|  | 408 | 9.1±1.8(0.1mM), 9.6±3.9(0.3mM) |
|  | isaxonine | 23.8±4.0(10mM) |
|  | control | 1.8±0.8 |
| 6 | 264 | 5.2±3.1(0.1mM), 8.7±1.6(0.3mM), 15.2±3.2(1mM), 7.2±1.8(3mM) |
|  | 424 | 4.5±1.4(0.03mM), 7.6±1.3(0.1mM) |
|  | isaxonine | 27.3±4.4(10mM) |
|  | control | 2.1±0.5 |
| 7 | 360 | 6.5±0.7(0.03mM), 10.0±0.7(0.1mM) |
|  | 272 | 4.8±1.3(0.03mM), 30.9±2.8(0.1mM), 15.9±0.5(0.3mM), 17.0±4.3(1mM) |
|  | 676 | 4.2±2.1(1.0mM), 6.0±1.1(0.3mM) |
|  | isaxonine | 27.3±4.4(10mM) |
|  | control | 1.8±0.5 |
| 8 | 240 | 19.8±5.7(0.03mM), 38.7±4.5(0.1mM), 33.2±0.9(0.3mM), 30.9±5.9(1mM) |
|  | 296 | 44.4±5.5(0.1mM), 22.4±3.0(0.3mM) |
|  | 170 | 33.5±2.4(0.1mM), 31.0±4.6(0.3mM) |

TABLE 12-continued

| Run No. | Compound | Action on neuro - 2a — Number of cells having neurites with a length at least two times the diameter of each cell/total number of cells, % (concentration of the compound) |
|---|---|---|
|  | 224 | 4.6±1.7(0.03mM), 5.5±1.5(0.1mM) |
|  | 432 | 2.9±1.0(0.1mM), 3.6±1.7(0.3mM) |
|  | 604 | 18.7±4.1(0.1mM), 24.6±2.9(0.3mM) |
|  | 612 | 13.8±1.5(0.01mM), 19.1±3.0(0.03mM), 19.4±3.9(0.1mM), 22.4±2.4(0.3mM) |
|  | isaxonine | 21.1±0.6(10mM) |
|  | control | 1.7±1.3 |
| 9 | 636 | 12.1±3.4(0.03mM), 8.9±5.2(0.1mM) |
|  | 176 | 5.3±1.9(0.03mM), 3.2±3.1(0.1mM) |
|  | 184 | 18.8±4.7(0.1mM), 16.0±2.4(0.3mM) |
|  | 644 | 26.1±7.3(0.03mM), 14.7±7.3(0.1mM) |
|  | 620 | 4.7±0.4(0.01mM), 4.0±1.3(0.03mM) |
|  | 652 | 6.1±0.6(0.03mM), 12.5±2.8(0.1mM) |
|  | 152 | 6.2±2.3(0.03mM), 33.8±4.7(0.1mM) |
|  | isaxonine | 27.5±0.8(10mM) |
|  | control | 1.4±0.7 |
| 10 | 376 | 13.6±1.2(0.03mM), 14.7±1.5(0.1mM), 17.2±1.4(0.3mM), 16.4±3.0(1mM) |
|  | 200 | 4.2±1.6(0.01mM), 7.6±1.6(0.03mM) |
|  | 192 | 12.1±1.5(0.3mM), 14.6±1.0(1mM) |
|  | isaxonine | 27.8±2.5(10mM) |
|  | control | 3.0±0.8 |
| 11 | 660 | 13.5±1.3(0.03mM), 9.1±3.7(0.1mM) |
|  | 304 | 38.1±1.6(0.1mM), 15.3±6.3(0.3mM) |
|  | isaxonine | 30.7±3.8(10mM) |
|  | control | 2.6±0.5 |
| 12 | 692 | 5.8±0.9(0.03mM), 11.1±2.9(0.1mM) |
|  | 160 | 11.3±6.3(0.1mM), 6.7±4.3(.3mM) |
|  | isaxonine | 23.9±1.8(10mM) |
|  | control | 1.5±1.5 |
| 13 | 668 | 5.6±0.8(0.01mM), 4.8±0.4(0.03mM), 5.2±0.7(0.1mM), 4.1±2.5(0.3mM) |
|  | 668 | |
|  | 684 | 3.8±0.5(0.01mM), 5.8±2.0(0.03mM), 16.4±2.8(0.1mM) |
|  | 280 | 4.5±1.2(0.03mM), 17.2±1.3(0.1mM), 13.4±3.5(0.3mM), 17.4±2.6(1mM) |
|  | isaxonine | 15.8±2.2(3mM) |
|  | control | 2.9±1.0 |
| 14 | 368 | 3.5±0.5(0.03mM), 9.0±1.8(0.1mM) |
|  | 344 | 3.6±0.7(0.01mM), 4.0±L7(0.03mM), 4.7±1.8(0.1mM), 4.5±2.1(0.3mM) |
|  | isaxonine | 16.8±3.4(3mM) |
|  | control | 2.6±0.6 |
| 15 | 336 | 5.8±2.4(0.1mM), 6.3±2.8(0.3mM) |
|  | 120 | 4.9±1.0(0.1mM), 7.5±4.1(0.3mM) |
|  | 232 | 3.9±1.8(0.03mM), 18.7±5.2(0.1mM) |
|  | 248 | 4.3±0.4(0.03mM), 25.4±3.0(0.1mM), 21.5±5.7(0.3mM), 17.4±4.5(1mM) |
|  | isaxonine | 19.4±3.1(3mM) |
|  | control | 3.2±1.2 |
| 16 | 812 | 3.5±0.5(0.1mM), 3.4±0.5(0.3mM) |
|  | 816 | 4.7±2.1(0.03mM), 4.0±0.3(0.1mM) |
|  | 820 | 8.4±1.1(1mM), 8.8±2.3(3mM) |
|  | 800 | 11.4±1.2(0.3mM), 25.7±1.9(1mM), 22.30.7(3mM), 16.9±0.8(10mM) |
|  | 828 | 7.3±1.6(0.3mM), 6.1±2.0(1mM) |
|  | isaxonine | 27.0±3.8(10mM) |
|  | control | 2.3±0.4 |
| 17 | 1014 | 4.7±0.7(0.1mM), 7.6±1.5(0.3mM) |
|  | 1122 | 4.2±2.1(0.01mM), 10.2±3.8(0.03mM) |
|  | 1026 | 3.5±0.5(0.03mM), 5.6±2.2(0.1mM) |
|  | 1130 | 1.8±0.5(0.03mM), 2.0±0.3(0.1mM) |
|  | 1038 | 2.2±0.4(0.03mM), 2.9±0.3(0.1mM) |
|  | isaxonine | 27.4±2.4(10mM) |
|  | control | 1.8±1.3 |
| 18 | 112 | 4.8±0.1(0.03mM), 18.6±5.2(0.1mM), 2.6±0.6(0.3mM), 7.6±4.9(1mM) |
|  | 216 | 3.7±0.4(0.01mM), 6.3±2.4(0.03mM), 26.6±5.6(0.1mM) |
|  | isaxonine | 23.3±2.9(10mM) |
|  | control | 2.3±0.6 |
| 19 | 104 | 2.5±0.8(0.03mM), 4.1±1.5(0.1mM), 7.7±3.8(0.3mM), 3.6±1.4(1mM) |
|  | 352 | 3.2±1.9(0.1mM), 9.9±1.6(0.3mM) |
|  | isaxonine | 22.6±0.5(10mM) |

TABLE 12-continued

Action on neuro - 2a

| Run No. | Compound | Number of cells having neurites with a length at least two times the diameter of each cell/total number of cells, % (concentration of the compound) |
|---|---|---|
|  | control | 1.8±1.4 |
| 20 | 288 | 1.4±0.1(0.03mM), 3.3±0.9(0.1mM), 3.8±1.9(0.3mM), 5.1±2.7(1mM) |
|  | 256 | 4.5±0.6(0.03mM), 17.9±6.3(0.1mM), 21.6±4.9(0.3mM), 16.6±2.5(1mM) |
|  | isaxonine | 19.4±3.1(10mM) |
|  | control | 2.2±1.0 |
| 21 | 1086 | 1.9±1.8(0.03mM), 3.1±1.3(0.1mM), 8.7±0.8(0.3mM), 17.4±1.1(1mM) |
|  | 1110 | 3.4±1.1(0.01mM), 4.4±0.3(0.03mM), 6.34.4(0.1mM), 16.5±2.1(0.3mM) |
|  | isaxonine | 30.2±3.5(10mM) |
|  | control | 2.6±1.0 |
| 22 | 1090 | 3.7±1.0(0.01mM), 5.7±0.6(0.03mM), 12.2±2.5(0.1mM), 10.3±0.9(0.3mM) |
|  | 1158 | 9.9±1.4(0.03mM), 18.4±3.0(0.1mM), 22.16.7(0.3mM), 19.1±2.7(1mM) |
|  | isaxonine | 26.7±3.3(10mM) |
|  | control | 2.4±1.6 |
| 23 | 804 | 9.4±1.3(0.3mM), 13.0±2.1(0.5mM), 26.1±6.8(1mM), 18.8±3.1(2mM) |
|  | isaxonine | 28.5±5.4(10mM) |
|  | control | 1.4±0.2 |
| 24 | 1094 | 5.4±1.9(0.1mM), 16.9±1.2(0.3mM), |
|  | 1094 | 10.9±1.1(1mM) |
|  | 1098 | 5.3±1.4(0.01mM), 10.2±0.9(0.03mM), 5.72.0(0.1mM) |
|  | isaxonine | 15.7±4.1(3mM) |
|  | control | 1.2±1.1 |
| 25 | 1162 | 4.7±3.0(0.03mM), 5.9±1.9(0.1mM) |
|  | 1102 | 11.9±0.7(0.1mM), 10.1±3.0(0.3mM) |
|  | isaxonine | 26.7±7.7(10mM) |
|  | control | 1.8±0.8 |
| 26 | 138 | 6.3±1.8(0.03mM), 12.6±4.1(0.1mM) |
|  | 2004 | 6.6±2.2(0.03mM), 30.2±6.4(0.1mM) |
|  | 171-3 | 28.8±3.1(0.1mM), 19.5±7.0(0.3mM) |
|  | 2052 | 4.6±2.1(0.01mM), 3.7±0.4(0.03mM) |
|  | 2060 | 3.6±0.1(0.03mM), 7.6±0.7(1mM) |
|  | 2070-11 | 5.6±3.9(0.1mM), 11.7±3.1(0.3mM) |
|  | 2076 | 4.8±1.4(0.01mM), 1.9±1.3(0.03mM) |
| 26 | isaxonine | 31.4±5.5(10mM) |
|  | control | 2.5±0.2 |
| 27 | 2084 | 11.1±2.2(0.03mM), 17.6±6.6(0.1mM) |
|  | 2092 | 23.9±0.4(0.1mM), 11.0±3.9(1mM) |
|  | 2100 | 4.4±0.8(0.03mM), 4.7±1.4(0.1mM) |
|  | 2108 | 4.8±2.0(0.03mM), 13.5±0.1(1mM) |
|  | 146 | 8.7±2.0(0.03mM), 40.0±6.1(0.1mM) |
|  | 147-1 | 6.6±0.4(0.03mM), 30.5±6.1(0.1mM) |
|  | 2116 | 34.2±3.8(0.1mM), 8.2±3.6(0.3mM) |
|  | 2124 | 12.5±5.3(0.03mM), 31.7±7.0(0.1mM) |
|  | isaxonine | 31.4±5.5(10mM) |
|  | control | 2.5±0.2 |
| 28 | 165 | 41.0±0.7(0.1mM), 12.4±1.8(0.3mM) |
|  | 166 | 36.8±7.1(0.1mM), 13.4±4.0(0.3mM) |
|  | 167 | 22.5±3.4(0.1mM), 9.3±2.3(0.3mM) |
|  | 169 | 34.1±5.7(0.1mM), 16.6±5.2(0.3mM) |
|  | 171 | 37.1±1.9(0.1mM), 8.8±2.6(0.3mM) |
|  | 171-1 | 36.4±7.8(0.1mM), 15.2±3.1(0.3mM) |
|  | 171-11 | 36.8±7.1(0.1mM), 14.3±3.0(0.3mM) |
|  | isaxonine | 21.0±2.3(10mM) |
|  | control | 2.5±0.2 |
| 29 | 2132 | 32.6±4.4(0.1mM), 31.7±5.0(0.3mM) |
|  | 2140 | 5.4±3.9(0.03mM), 17.0±1.2(0.1mM) |
|  | 2148 | 4.5±1.3(0.03mM), 4.2±1.2(0.1mM) |
|  | 2156 | 8.6±1.0(0.03mM), 19.6±5.3(0.1mM) |
|  | 307-1 | 3.6±0.4(0.03mM), 9.0±2.5(0.3mM) |
|  | 2164 | 4.6±1.1(0.1mM), 11.7±0.7(1mM) |
|  | isaxonine | 21.0±2.3(10mM) |
|  | control | 3.1±1.2 |
| 30 | 154 | 5.2±1.5(0.03mM), 16.2±2.1(0.1mM) |
|  | 2174 | 2.5±1.0(0.01mM) |
|  | 2182 | 8.0±3.2(0.03mM), 2.7±0.9(0.1mM) |
|  | 2188 | 2.4±0.9(0.1mM), 3.8±1.1(0.3mM) |
|  | 2194 | 9.5±3.5(0.1mM), 7.6±2.8(0.3mM) |
|  | 2202 | 2.2±2.0(0.1mM) |
|  | 2210 | 9.5±2.0(0.03mM), 9.5±1.9(0.1mM) |
|  | isaxonine | 19.4±2.4(10mM) |
|  | control | 1.7±0.9 |
| 31 | 2218 | 9.7±1.8(0.03mM), 11.4±6.1(0.1mM) |
|  | 662 | 3.1±1.6(0.1mM), 2.6±0.9(0.3mM) |
|  | 2226 | 6.4±3.3(0.03mM), 15.4±3.9(0.1mM) |
|  | 2234 | 5.1±3.2(0.03mM), 5.7±2.8(0.1mM) |
|  | 2242 | 3.3±0.9(0.03mM), 24.8±2.9(0.1mM) |
|  | 2250 | 10.9±3.9(0.1mM), 19.2±1.0(0.3mM) |
|  | isaxonine | 19.4±2.4(10mM) |
|  | control | 1.7±0.9 |
| 32 | 2260 | 2.2±0.3(0.03mM), 2.3±0.5(0.1mM) |
|  | 2270 | 14.7±5.1(0.03mM), 19.9±4.2(0.1mM), 21.3±3.5(0.3mM), 15.2±1.5(1mM) |
|  | 2278 | 13.9±6.3(0.03mM), 12.5±1.3(0.1mM) |
|  | 2286 | 9.7±5.4(0.03mM), 8.4±0.8(0.1mM) |
|  | 2294 | 3.7±0.9(0.03mM), 8.1±1.6(0.1mM) |
|  | 2302 | 8.0±2.7(0.03mM), 8.2±4.7(0.1mM) |
|  | isaxonine | 19.4±2.4(10mM) |
|  | control | 1.7±0.9 |
| 33 | 2012 | 6.6±1.2(0.03mM), 6.6±3.1(0.3mM) |
|  | 2020 | 4.6±1.1(0.03mM), 33.8±9.6(0.1mM), 30.5±9.5(0.3mM), 15.1±5.0(1mM) |
|  | 2028 | 4.0±0.8(0.03mM), 12.5±1.2(0.1mM) |
|  | 2036 | 3.9±0.8(0.03mM), 5.4±1.1(0.1mM) |
|  | 2044 | 3.7±0.7(0.01mM), 10.3±4.7(0.1mM) |
|  | isaxonine | 19.5±3.6(10mM) |
|  | control | 2.7±0.6 |
| 34 | 2310 | 8.3±1.8(0.1mM), 12.1±3.6(0.3mM) |
|  | 2318 | 7.7±1.4(0.03mM), 35.1±1.3(0.1mM), 18.65.2(0.3mM), 8.8±1.3(1mM) |
|  | 2326 | 4.6±1.4(0.03mM), 8.3±2.6(0.1mM) |
|  | 2334 | 13.2±0.2(0.03mM), 16.7±0.8(0.1mM) |
|  | 2342 | 5.9±2.1(0.03mM), 11.4±1.4(0.1mM) |
|  | 2350 | 5.9±1.5(0.3mM), 8.3±2.0(1mM) |
|  | 154-2 | 3.9±0.6(0.03mM), 8.9±2.4(0.1mM) |
|  | 171-5 | 7.2±1.1(0.01mM), 28.4±2.2(0.1mM), 32.7±0.6(0.3mM), 14.0±4.1(1mM) |
|  | isaxonine | 16.1±0.6(10mM) |
|  | control | 3.3±0.6 |
| 35 | 3104 | 2.8±0.8(0.03mM), 4.0±2.2(0.1mM), 7.2±2.8(0.3mM), 6.1±1.6(1mM) |
|  | isaxonine | 16.8±3.4(3mM) |
|  | control | 2.6±0.6 |
| 36 | 3144 | 20.8±4.7(0.03mM), 34.1±3.8(0.1mM), 44.5±9.7(0.3mM), 32.2±1.6(1mM) |
|  | isaxonine | 30.8±2.9(10mM) |
|  | control | 3.2±1.6 |
| 37 | 3200 | 3.6±0.5(0.03mM) |
|  | isaxonine | 23.3±2.9(10mM) |
|  | control | 2.3±0.6 |
|  | 3300 | 6.1±1.2(0.3mM), 7.8±1.0(1mM) |
| 38 | 3200 | 2.7±0.7(0.01mM), 2.5±2.3(0.03mM) |
|  | isaxonine | 19.4±3.1(3mM) |
|  | control | 3.2±1.2 |
| 39 | 3136 | 5.8±0.6(0.01mM), 13.8±4.8(0.03mM), 20.5.3(0.1mM), 7.1±3.0(0.3mM) |
|  | isaxonine | 22.6±0.5(10mM) |
|  | control | 1.8±1.4 |
| 40 | 3128 | 14.2±1.9(0.1mM), 11.9±4.5(0.3mM) |
|  | 3112 | 6.3±0.4(0.03mM), 6.2±3.4(0.1mM) |
|  | 3152 | 11.4±3.1(0.03mM), 6.8±4.2(0.1mM) |
|  | 3176 | 7.3±3.3(0.03mM), 23.1±4.8(0.1mM), 21.4±9(0.3mM), 14.6±5.0(1mM) |
|  | 3184 | 3.7±1.1(0.03mM), 13.9±2.3(0.1mM), 18.±1.9(0.3mM), 17.0±2.1(1mM) |
|  | 3192 | 9.7±1.1(0.1mM), 3.7±3.2(0.3mM) |
|  | isaxonine | 19.4±3.1(10mM) |
|  | control | 2.2±1.0 |
| 41 | 3404 | 3.3±1.3(0.03mM), 3.4±1.4(0.3mM) |
|  | 3412 | 2.9±0.9(0.03mM), 20.6±8.2(0.1mM) |
|  | 3420 | 4.2±1.9(0.03mM), 8.7±2.3(0.1mM) |
|  | isaxonine | 19.4±2.4(10mM) |
|  | control | 1.7±0.9 |
| 42 | 298 | 2.7±1.7(0.1mM), 6.1±5.6(0.3mM) |

TABLE 12-continued

Action on neuro - 2a

| Run No. | Compound | Number of cells having neurites with a length at least two times the diameter of each cell/total number of cells, % (concentration of the compound) |
|---|---|---|
|  | 306 | 7.7±0.5(0.03mM), 2.8±0.8(0.1mM) |
|  | 242 | 17.0±2.3(0.1mM), 12.8±6.3(0.3mM) 9.4±3.9(1mM) |
|  | 150 | 9.3±1.9(0.03mM), 13.6±1.2(0.1mM) 6.6±3.0(0.3mM) |
|  | 171-9 | 24.4±6.6(0.1mM), 7.1±2.9(0.3mM) |
|  | isaxonine | 12.1±1.6(3mM) |
|  | control | 2.4±0.4 |
| 43 | 171-11 | 5.9±0.9(0.03mM), 22.1±2.3(0.1mM) 29.2±1.5(0.3mM), 31.7±5.9(1mM) |
|  | 170-2 | 14.7±1.1(0.1mM), 5.6±2.1(0.3mM) 13.9±3.0(1mM) |
|  | 171-7 | 8.5±1.0(0.03mM), 6.7±3.1(0.1mM) |
|  | 171-12 | 13.3±1.1(0.1mM), 10.7±4.2(0.3mM) 12.70.9(1mM) |
|  | isaxonine | 14.9±1.9(10mM) |
|  | control | 2.5±1.0 |
| 44 | 2022-1 | 23.1±4.8(0.1mM), 18.1±2.8(0.3mM) 19.82.1(1mM) |
|  | 2023-1 | 8.3±2.1(0.1mM), 7.0±0.5(0.3mM) |
|  | isaxonine | 20.1±3.0(10mM) |
|  | control | 3.2±0.9 |

TABLE 13

Activity on NS-20Y cells

| Compound | 24 hours | 48 hours |
|---|---|---|
| | Number of cells in which neurites appeared/total number of cells (concentration of the compound) | |
| 112 | 4/51(0.025mM) | 9/50(0.025mM) 4/49(0.01mM) |
| control | 0/51 | 1/51 |
| 120 | 23/50(0.5mM) | 4/50(0.5mM) |
| control | 1/49 | 0/50 |
| 144 | 37/50(0.1mM) | 31/50(0.1mM) 8/52(0.05mM) |
| control | 0/50 | 1/50 6/50(0.025mM) |
| 152 | 3/50(0.05mM) | 2/50(0.025mM) |
| control | 0/50 | 0/50 |
| 160 | 10/53(0.5mM) | 2/50(0.5mM) |
| control | 0/50 | 0/50 |
| 168 | 26/50(0.1mM) 12/50(0.25mM) | 20/55(0.1mM) |
| control | 3/50 | 2/50 |
| 208 | 27/53(0.1mM) 17/51(0.25mM) | 28/50(0.1mM) |
| control | 1/50 | 0/52 |
| 128 | 23/55(1.0mM) 4/49(0.3mM) | 31/50(0.3mM) 21/50(0.5mM) |
| control | 3/50 | 4/50 |
| 216 | 3/49(0.025mM) | 24/50(0.025mM) 20/50(0.05mM) |
| control | 0/51 | 1/50 |
| 232 | 2/50(0.025mM) | 2/49(0.01mM) |
| control | 0/51 | 0/50 |
| 240 | 4/50(0.2mM) | 3/50(0.2mM) |
| control | 0/50 | 0/50 |
| 248 | 3/49(0.1mM) | 2/50(0.05mM) |
| control | 0/49 | 0/50 |
| 256 | 5/51(0.2mM) | 2/48(0.05mM) |
| control | 0/51 | 0/50 |
| 272 | 33/50(0.1mM) 24/50(0.2mM) | 17/50(0.1mM) |
| control | 0/50 | 0/51 |
| 280 | 3/50(0.2mM) | 8/53(0.1mM) |
| control | 0/50 | 1/53 |
| 288 | 2/52(0.1mM) | 2/50(0.1mM) |
| control | 0/50 | 0/50 |
| 296 | 9/49(0.1mM) | 2/50(0.1mM) |
| control | 0/50 | 0/48 |
| 304 | 40/50(0.1mM) | 3/50(0.01mM) |
| control | 0/51 | 0/51 |
| 328 | 32/50(0.1mM) | 8/50(0.025mM) 12/51(0.1mM) |
| control | 0/51 | 0/50 |
| 336 | 3/54(0.2mM) | 2/50(0.5mM) |
| control | 0/52 | 0/50 |
| 344 | 3/51(0.2mM) | 2/49(0.5mM) |
| control | 0/50 | 0/51 |
| 368 | 14/50(0.1mM) | 8/51(0.05mM) 5/50(0.1mM) |
| control | 0/50 | 0/50 |
| 376 | 2/50(0.2mM) | 2/50(0.1mM) |
| control | 0/50 | 0/50 |
| 392 | 8/50(0.1mM) | 6/51(0.05mM) 3/43(0.1mM) |
| control | 0/52 | 0/50 |
| 612 | 2/50(0.1mM) | 2/50(0.1mM) |
| control | 0/50 | 1/51 |
| 668 | 2/50(0.1mM) | 2/50(0.05mM) |
| control | 0/50 | 0/50 |
| 684 | 2.50(0.1mM) | 2/50(0.05mM) |
| control | 0/53 | 0/50 |
| 1094 | 7/48(0.4mM) | 2/50(0.0mM) 4/54(0.1mM) |
| control | 2/50 | 1/50 |
| 1026 | 31/50(0.1mM) 4/50(0.02mM) | 2/50(0.02mM) |
| control | 2/50 | 1/50 |
| 1086 | 4/50(0.4mM) | 2/50(0.02mM) |
| control | 2/50 | 1/50 |
| 1090 | 21/50(0.1mM) 4/50(0.02mM) | 3/50(0.1mM) |
| control | 1/50 | 1/50 |
| 1014 | 9/50(0.4mM) 3/50(0.1mM) | 6/50(0.4mM) |
| control | 2/50 | 2/50 |
| 384 | 8/50(0.4mM) | 3/50(0.4mM) |
| control | 2/50 | 1/50 |
| 416 | 11/50(0.4mM) 7/50(0.1mM) | 2/50(0.1mM) |
| control | 1/50 | 0/50 |
| 320 | 8/50(0.1mM) | 6/50(0.1mM) |
| control | 2/50 | 1/50 |
| 400 | 30/53(0.4mM) 9/50(0.1mM) | 3/48(0.4mM) 3/50(0.1mM) |
| control | 2/50 | 1/50 |
| 136 | 42/50(0.4mM) 9/50(0.1mM) | 15/50(0.4mM) |
| control | 3/50 | 1/50 |
| 264 | 8/48(0.4mM) | 4/50(0.4mM) |
| control | 2/50 | 1/50 |
| 424 | 16/50(0.4mM) | 3/50(0.4mM) |
| control | 3/52 | 1/50 |
| 360 | 18/50(0.1mM) 8/50(0.02mM) | 4/50(0.1mM) |
| control | 3/50 | 1/50 |
| 224 | 6/50(0.02mM) | 3/50(0.02mM) |
| control | 1/50 | 1/50 |
| 432 | 7/50(0.4mM) 7/50(0.02mM) | 4/50(0.4mM) |
| control | 2/50 | 2/50 |
| 200 | 4/50(0.02mM) | 2/50(0.02mM) |
| control | 2/50 | 1/50 |
| 192 | 23/50(0.4mM) | 4/50(0.4mM) |
| control | 2/50 | 1/50 |
| 176 | 8/50(0.1mM) | 2/50(0.02mM) |
| control | 1/50 | 0/50 |
| 184 | 8/50(0.02mM) 5/48(0.1mM) | 3/50(0.02mM) |
| control | 1/52 | 1/50 |
| 628 | 9/50(0.1mM) | 3/50(0.1mM) |
| control | 3/50 | 1/50 |
| 700 | 6/50(0.4mM) 4/53(0.1mM) | 4/50(0.1mM) |
| control | 2/50 | 1/50 |
| 660 | 5/50(0.1mM) | 4/50(0.1mM) |

TABLE 13-continued

Activity on NS-20Y cells

Number of cells in which neurites appeared/total number of cells (concentration of the compound)

| Compound | 24 hours | 48 hours |
|---|---|---|
| control | 2/50 | 1/50 |
| 604 | 7/50(0.4mM) | 2/50(0.02mM) |
|  | 6/50(0.02mM) |  |
| control | 2/50 | 1/50 |
| 804 | 8/55(0.25mM) | 25/51(0.5mM) |
|  | 7/50(0.5mM) | 8/50(0.25mM) |
| control | 4/50 | 0/50 |
| 168 | 26/50(0.1mM) | 20/55(0.1mM) |
|  | 12/50(0.25mM) |  |
| control | 3/50 | 2/50 |
| 208 | 27/53(0.1mM) | 28/50(0.1mM) |
|  | 17/51(0.25mM) |  |
| control | 1/50 | 0/52 |
| 820 | 5/53(0.5mM) | 5/55(0.25mM) |
|  | 4/50(0.1mM) | 4/50(0.1mM) |
| control | 3/50 | 0/50 |
| 828 | 10/58(0.3mM) | 6/50(0.3mM) |
|  | 5/59(0.5mM) | 5/51(0.5mM) |
| control | 2/50 | 2/51 |
| 812 | 11/50(1.0mM) | 9/50(0.3mM) |
|  | 9/50(0.5mM) | 5/51(0.5mM) |
| control | 2/53 | 2/50 |
| 3192 | 6/50(0.02mM) | 4/50(0.02mM) |
| control | 1/50 | 0/50 |
| 242 | 6/50(0.4mM) | 11/50(0.2mM) |
|  | 4/50(0.2mM) | 6/50(0.1mM) |
| control | 0/50 | 0/50 |
| 2022-1 | 12/50(0.2mM) | 2/50(0.1mM) |
|  | 5/50(0.4mM) |  |
| control | 0/50 | 0/50 |
| 2023-1 | 2/50(0.1mM) | 2/50(0.2mM) |
| control | 0/50 | 0/50 |
| 171-9 | 7/45(0.4mM) | 2/50(0.02mM) |
| control | 0/50 | 0/50 |
| 171-11 | 5/50(0.3mM) | 2/50(0.1mM) |
| control | 0/50 | 9/50 |
| 170-2 | 3/50(0.1mM) | 2/50(0.1mM) |
| control | 0/50 | 0/50 |
| 171-7 | 4/50(0.1mM) | 2/50(0.1mM) |
| control | 0/50 | 0/50 |

EXAMPLE 2

Therapeutic Effect On Rats With Crushed Sciatic Nerves

The therapeutic effect of the compound of the invention was tested on rats having crushed sciatic nerves as a model of peripheral nervous disorder using (1) a change in the action of the hind paw with the crushed sciatic nerves and (2) change in the weight of the muscle as an index of the course of degeneration and regeneration of peripheral nerves.

In the experiment, male Wistar rats (6 weeks old), seven per group, were used. The sciatic nerves were crushed by a method similar to the method of Yamatsu et al. (see Kiyomi Yamatsu, Takenori Kaneko, Akifumi, Kitahara and Isao Ohkawa, Journal of Japanese Pharmacological Society, 72, 259-268 (1976) and the method of Hasegawa et al. (see Kazuo Hasegawa, Naoji Mikuni and Yutaka Sakai, Journal of Japanese Pharmacological Society, 74, 721-734 (1978). Specifically, under anesthesia with pentobarbital (40 mg/kg, i.p.), the left side sciatic nerve was exposed at the femur, and a specific site of the exposed sciatic nerve was crushed for 30 seconds by using a hemostat. After the crushing, the opetation site was immediately sutured. Thereafter, vincristine known to retard the regeneration of the peripheral nerve was intraperitoneally administered in a dose of 100 g/kg once a week.

Compounds of the invention were selected as test drugs, and administered intraperitoneally once a day from the day of crushing to 30th day from then. To a control group, only 0.9% saline was administered.

(1) Functional Change In The Hind Paw With Crushed Nerves

Twitch tension, which is a transient tension incident to contraction of the dominated muscles that occurs by electrical stimulation or the like of motor nerves, as is the case with the interdigit distance to be described, is considered to reflect functional changes of the nerves and muscles.

Thus, 30 days later, under aesthesia with chloral hydrate (400 mg/kg, i.p.), the twitch tension of rats was measured by the method of Kern et al. [J. Neurosci. Methods, 19, 259 (1987)]. Specifically, the hair on the hind paw of rats was shaven, and coated with Cardiocream (a product of Nihon Denko K.K.). Then, to the skin of the hind paw, electrodes with an alligator were attached. The cathode was attached to the rear portion of the trochiter, and the anode, to a site 1 cm rearwardly of the anode electrode and 1 cm toward its back. The rat was fixed on its back, and the hind paw to be measured was fixed perpendicularly. A silk yarn, about 20 cm long, was connected at one end to the third efferent toe joint of the hind paw to be measured and at the other end to a tension transducer. Isotonic contractions of the third muscle digitus flexus were recorded on a polygraph. Electrical stimulation was effected at a voltage of 100 V for a continuous duration of 1 msec. with rectangular waves at a frequency of 2 Hz. The static tension was 15 to 30 g, and 10 stimulations were repeated 3 times with intervals of 15 seconds. The contracting force was expressed as tension (g). From the measured values of both paws, the recovery ratio (%, left/right) of the contracting force of the paw with crushed nerves was calculated. The results are shown in Tables 14 and 15.

TABLE 14

| Compound | Twitch tension Dose (mg/kg) | Number of cases | Twitch tension[1] left/right (%) |
|---|---|---|---|
| Saline | — | 7 | 33.3 ± 7.0 |
| 168 | 10 | 7 | 48.4 ± 11.8[2] |
| 168 | 30 | 8 | 51.2 ± 13.6[3] |
| 296 | 30 | 8 | 48.1 ± 9.4[2] |

[1]mean ± S.D.,
[2]p <0.05,
[3]p <0.01

TABLE 15

| Compound | Dose (mg/kg) | Number of cases | Twitch tension left/right (%) 18th days | Twitch tension left/right (%) 23rd days |
|---|---|---|---|---|
| Physiological saline | — | 7 | 44.2 ± 17.6 | 49.8 ± 14.8 |
| 3144 | 30 | 8 | 54.5 ± 17.1 | 57.9 ± 15.5 |

The test compounds evidently increased the recovery of twitch tension, which is an electrophysiological index, and improved symptom, over the control group.

The distance between digits was measured because this is a good index which functionally shows the degeneration and regeneration of the nerve and its change can be measured with the lapse of time.

By a method similar to the method of Hasegawa [Hasegawa, K., Experientia, 34, 750–751 (1978)], the distance between the first and fifth digits of the hind paw was measured.

The ratio of the measured distance to the interdigit distance in a normal hind paw was calculated and expressed in percentage (%). The interdigit distance of the hind paw with crushed nerves was less than 50% of that in a normal hind paw immediately after the crushing. Recovery of the interdigit distance began 12 to 16 days later, and in drug-administered groups, there was evidently a tendency to accelerated recovery in comparison with the control group from about 17th day to the final day (26th).

One example is shown in Table 16.

TABLE 16

Therapeutic effect on rats having crushed sciatic nerves

| Compound | Dose (mg/kg, i.p.) | Recovery of the interdigit distance | |
|---|---|---|---|
| | | 18th days | 23rd days |
| Physiological saline | 1 ml/kg | 67.6 ± 16.1 | 76.5 ± 20.2 |
| 3144 | 30 | 72.7 ± 14.0 | 83.8 ± 12.2 |

(2) Change In The Weight Of Muscle

It is known that removal of a nerve or its disorder causes atrophy of the muscle which is under its control, and the atrophy is gradually cured by re-control by the nerve. For this reason, a change in the weight of the muscle, which is quantitative, was selected as an index. Thirty days after the operation, the muscles extensor digitorum longus of both hind paws which are muscles under the control of sciatic nerves were extracted under anesthesia, and their weights were measured. The ratio of the weight of the muscle extensor digitorum longus on the crushed side to that of normal side was calculated and expressed in percentage (%). The results are shown in Table 17.

TABLE 17

| Compound | Dose (mg/kg) | Number of cases | Weight of muscle extensor digitorum longus[*1] left/right (%) |
|---|---|---|---|
| Saline | — | 7 | 48.8 ± 6.4 |
| 168 | 10 | 7 | 52.1 ± 5.4 |
| 168 | 30 | 8 | 59.4 ± 11.8[*2] |
| 296 | 30 | 8 | 56.9 ± 9.7[*2] |

[*1] mean ± S.D.,
[*2] $p < 0.05$

The results show that the test compounds, in comparison with the control, evidently increased the weight % of muscle extensor digitorum longus.

Accordingly, these test compounds are useful as improvers and therapeutic agents for peripheral nerve disorders.

EXPERIMENTAL EXAMPLE 3

Promoting Effect On The Improvement Of Motor Imbalance Due To Injury Of The Rat's Brain Cells By Transplantation Of Fetal Cerebral Cells Nigral dopaminergic nerve cells at the left side of the brain of 4-week old female Wistar rats (body weight 100 g) were lesioned by injecting a very small quantity of 6-hydroxydopamine. The rats showed a tendency to rotate spontaneously in a direction opposite to the lesioned side for several days, but no apparent abnormal action was observed after that. Upon administration of methamphetamine (5 mg/kg, i.p.) to the rats having the lesioned nigral dopaminergic nerve cells, they began rotational movement toward the lesioned side.

After two weeks from the destruction by the administration of the drug, portions of the truncus corporis callosi containing dopamine cells (i.e., substantia nigra and the tagmentum at the abdomen side) were cut from the brain of a fetal rat of 14 to 17 days of age, cut finely, and treated with trypsin. Then, the extracted tissues were incubated at 37° C. for 30 minutes, and the tissues were subjected to pipetting to form a suspension. Five microliters of the suspension was transplanted each into two sites of the caudate nucleus of the lesioned side (10 microliters in total, about $10^5$ cells).

Compound No. 168 of the invention was administered in a dose of 156 mg/kg (i.p.) for 4 days from the day of transplantation, then with a suspension of 7 days, for 10 days in a dose of 50 mg/kg (i.p.) from the 11th day. Compound No. 296 was administered in a dose of 153 mg/kg, and then 50 mg/kg, in accordance with the same schedule.

Compound No. 3144 was also administered in accordance with the same schedule in a dose of 135 mg/kg, and then 45 mg/kg.

The rotational movements induced by administration of methamphetamine were examined 2 weeks and 1 week before, and 2 (or 3), 4, 6 and 8 weeks after, the transplantation and the administration of the drug. The number of rotational movements for the first one minute was counted at intervals of 10 minutes after the administration of methamphetamine, and the total number of rotational movements counted six times was averaged to find a mean number of the rotational movements.

The results are shown in Table 18.

The results are shown that the test compounds are useful as improvers and therapeutic agents for cental nerve disorders.

TABLE 18

| Compound | −1 W | 3 W | 4 W | 6 W | 8 W |
|---|---|---|---|---|---|
| 168 | 13.3 ± 7.8 | 9.1 ± 5.6 | 4.5 ± 4.5 | 1.5 ± 3.9 | 0.8 ± 2.1 |
| 296 | 13.2 ± 4.1 | 8.4 ± 5.0 | 3.1 ± 3.4 | 0.9 ± 2.3 | 1.0 ± 1.5 |
| 3144 | 14.1 ± 4.7 | 7.7 ± 4.7 | 4.0 ± 5.6 | 0.2 ± 2.2 | 1.1 ± 4.1 |
| Physiological saline | 16.7 ± 9.1 | 11.2 ± 9.6 | 5.3 ± 8.3 | 2.8 ± 5.4 | 2.2 ± 6.0 |

EXPERIMENTAL EXAMPLE 4

Improvement Of Learning And Memory Of Mice With Nerve Disorder Induced By Mercury Poisoning, And Recovery Effect Male BalbC strain mice, 7 weeks old, were first caused to learn a T-shaped maze three times in a week so that they run straight from a starting point to a safety area. Then, methylmercury chloride (MMC for short) was administered orally in a dose of 6 mg/kg/day for 6 days to male Balb C strain mice (7 weeks old). A group of mice to which saline was administered in a dose of 0.1 ml/10 g/day was used as a control group. Beginning with the day next to the day of administering MMC, compounds of the invention were intraperitoneally administered over 10 days. On the sixth day after administration of the drug (namely, on the 12th day after start of the experiment), learning of the T-shaped maze was resumed, and the running behaviors of the mice were observed. The number of mice which could be experimented in the T-shaped maze on the 10th and 11th days after the resumption (21st and 22nd days after the start of the experiment) was counted and expressed as a denominator. The number of mice which ran to the safety area within 5 seconds at least 8 times out of ten trial runnings was counted and expressed as a numerator. The decrease in the number of the test animals was due to death by MMC poisoning. The time (seconds) required for the animals to run to the safety area was measured, and the mean ± standard error (SE) was calculated.

The results demonstrate the effect of the compounds of the invention to improve learning and momory of the mice and their recovery effect.

EXPERIMENTAL EXAMPLE 5

The acute toxicity of the compounds of the invention was examined by the following method.

Male ddy-strain 5-week old mice, 4–6 per group, were used as experimental animals. Each of the compounds was intraperitoneally (i.p.), and the toxicity of the compound was assessed 24 hours after the administration. The results are shown in Table 19.

TABLE 19

| Acute toxicity on mice | |
| --- | --- |
| Compound | Estimated $LD_{50}$ (mg/kg, i.p) |
| 128 | >1000 |
| 136 | >1000 |
| 144 | >1000 |
| 152 | >1000 |
| 168 | >1000 |
| 208 | >1000 |
| 392 | 500–1000 |
| 328 | >1000 |
| 408 | 500–1000 |
| 240 | >1000 |
| 296 | >1000 |
| 272 | >1000 |
| 170 | >1000 |
| 604 | <500 |
| 644 | >1000 |
| 304 | >1000 |
| 360 | >1000 |
| 376 | 500–1000 |
| 424 | >1000 |
| 248 | >1000 |
| 216 | >1000 |
| 1090 | 500–1000 |
| 1158 | <250 |
| 612 | 500–1000 |
| 184 | >1000 |
| 192 | 500–1000 |
| 280 | 500–1000 |
| 232 | >1000 |
| 112 | >1000 |
| 120 | >1000 |
| 160 | >1000 |
| 176 | >1000 |
| 264 | 500–1000 |
| 312 | >1000 |
| 320 | >1000 |
| 352 | 500–1000 |
| 368 | 500–1000 |
| 400 | 500–1000 |
| 628 | 500–1000 |
| 660 | 500–1000 |
| 684 | 500–1000 |
| 804 | 500–1000 |
| 104 | 500–1000 |
| 138 | >1000 |
| 2004 | >1000 |
| 146 | >1000 |
| 154 | >1000 |
| 147-1 | >1000 |
| 169 | >1000 |
| 2116 | 500–1000 |
| 2124 | >1000 |
| 171-3 | >1000 |
| 256 | >1000 |
| 288 | 500–1000 |
| 2132 | >1000 |
| 2140 | >1000 |
| 2020 | 500–1000 |
| 2028 | 500–1000 |
| 2044 | 500–1000 |
| 2070 | >1000 |
| 2084 | >1000 |
| 2092 | >1000 |
| 2156 | >1000 |
| 2164 | >1000 |
| 2182 | 500–1000 |
| 2210 | 500–1000 |
| 2218 | 500–1000 |
| 2242 | 500–1000 |
| 2250 | 500–1000 |
| 2270 | >1000 |
| 2278 | 500–1000 |
| 2302 | 500–1000 |
| 2318 | 500–1000 |
| 2326 | 500–1000 |
| 2342 | 500–1000 |
| 154.2 | 500–1000 |
| 171-5 | >1000 |
| 2310 | 500–1000 |
| 2350 | 500–1000 |
| 3104 | >1000 |
| 3122, 3144, 3176, 3184, 3192, 3412 and 3420 | 500–1000 |
| 2318 | >1000 |
| 2334 | >1000 |
| 171-9 | 500–1000 |
| 171-11 | >1000 |
| 170-2 | 500–1000 |
| 170-12 | >1000 |
| 2022-1 | >1000 |

The compounds of general formulae (1), (2) and (3) provided by this invention have a promoting effect on the proliferation of nerve cells and the formation and sprouting of neurites and a nerve regenerating effect and a motor function recovering effect in rats and mice having nerve disorders, and can be used suitably for improving and curing neurological diseases such as disorders of peripheral nerves or central nerves and dementia. They are expected to be used also suitably for the recovery, improving and curing of neurological diseases caused by nervous tissues and cells which have to do with perceptive and sensory functions and an autonomic function.

It has been found that the compounds of the invention have biological activities equal to, or higher than, those of isaxonine and mecobalamin as a control as shown in Experimental Examples 1 to 4 and Tables 12 to 19. The toxicity of the compounds of this invention are generally weak as shown in Experimental Example 5. Thus, the compounds of this invention are generally considered to be highly active and highly safe drugs and very useful with weak toxicity.

We claim:

1. A compound of the following formula (3), or a pharmaceutically acceptable salt thereof,

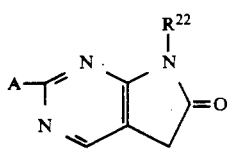
(3)

wherein

A represents a group of the formula

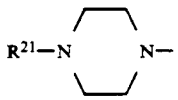

or a group of the formula

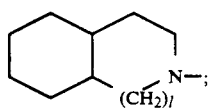

$R^{22}$ represents a lower alkyl group;
$R^{21}$ represents a group of the formula

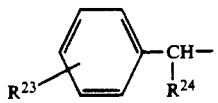

wherein
$R^{23}$ represents a hydrogen atom, a lower alkyl group, a lower alkoxy group or a phenyl group, and
$R^{24}$ represents a hydrogen atom, a lower alkyl group, a cyclohexyl group, a phenyl group, a 4-halogenophenyl group, a p-diphenyl group a 2-pyridyl group or a 2-thiophenyl group,
provided that $R^{23}$ and $R^{24}$ are not hydrogen atoms at the same time, and $R^{24}$ is not a lower alkyl group when $R^{23}$ is a hydrogen atom; and
l is a number of 0 or 1.

2. The compound according to claim 1, wherein A represents a group of the formula

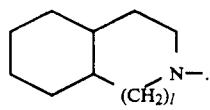

3. The compound according to claim 1, wherein the pharmaceutically acceptable salt is selected from the group consisting of hydrochlorides, hydrobromides, bisulfites, phosphates, acidic phosphates, acetates, maleates, fumarates, succinates, lactates, tartrates, benzoates, citrates, glucanates, methansulfonates, p-toluenesulfonates, naphthalenesulfonates, and quaternary ammonium salts.

4. A pharmaceutical composition for treatment of neurological diseases induced by injury to nerve per se comprising the compound of claim 1 or a pharmaceutically acceptable salt thereof as an active ingredient and a pharmaceutically acceptable carrier.

5. A method for the treatment of neurological diseases induced by injury to nerve per se which comprises administering to a patient in need thereof a pharmacologically effective amount of the compound of claim 1 or a pharmaceutically acceptable salt thereof.

* * * * *

UNITED STATES PATENT AND TRADEMARK OFFICE
CERTIFICATE OF CORRECTION

PATENT NO. : 5,264,435
DATED : November 23, 1993
INVENTOR(S) : Akira Mizuchi, et al.

It is certified that error appears in the above-identified patent and that said Letters Patent is hereby corrected as shown below:

On the title page, at Item 73, Assignee:
    after "Mitsui Petrochemical Industries, Ltd."
    Insert --Mitsui Pharmaceuticals, Inc.--

Signed and Sealed this

Ninth Day of August, 1994

Attest:

BRUCE LEHMAN

Attesting Officer     Commissioner of Patents and Trademarks